(12) United States Patent
Greenfield et al.

(10) Patent No.: US 11,939,398 B2
(45) Date of Patent: Mar. 26, 2024

(54) MODIFIED PEPTIDES FOR USE IN TREATING NEURODEGENERATIVE DISORDERS

(71) Applicant: Neuro-Bio Ltd, Abingdon (GB)

(72) Inventors: Susan Greenfield, Abingdon (GB);
Sara Garcia-Rates, Abingdon (GB);
Jesus Seco Moral, Barcelona (ES);
Roger Prades Cosano, Barcelona (ES)

(73) Assignee: Neuro-Bio Ltd, Abingdon (GB)

( * ) Notice: Subject to any disclaimer, the term of this patent is extended or adjusted under 35 U.S.C. 154(b) by 213 days.

(21) Appl. No.: 16/325,716

(22) PCT Filed: Aug. 16, 2017

(86) PCT No.: PCT/GB2017/052407
§ 371 (c)(1),
(2) Date: Feb. 14, 2019

(87) PCT Pub. No.: WO2018/033724
PCT Pub. Date: Feb. 22, 2018

(65) Prior Publication Data
US 2021/0094983 A1 Apr. 1, 2021

(30) Foreign Application Priority Data

Aug. 16, 2016 (GB) ..................................... 1613999
Jan. 30, 2017 (GB) ..................................... 1701455

(51) Int. Cl.
| | |
|---|---|
| *C07K 5/08* | (2006.01) |
| *A61P 25/28* | (2006.01) |
| *C07K 5/087* | (2006.01) |
| *C07K 5/09* | (2006.01) |
| *C07K 5/097* | (2006.01) |
| *A61K 38/00* | (2006.01) |

(52) U.S. Cl.
CPC ............ *C07K 5/0821* (2013.01); *A61P 25/28* (2018.01); *C07K 5/0812* (2013.01); *C07K 5/0817* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,235,718 B1 * | 5/2001 | Balasubramanium | ....................... A61K 38/05 530/331 |
| 8,697,634 B2 | 4/2014 | Gazit | |
| 2005/0159362 A1 | 7/2005 | Ohno et al. | |
| 2009/0221513 A1 * | 9/2009 | Rose | ....................... A61K 38/06 514/1.1 |
| 2014/0349920 A1 | 11/2014 | Yu et al. | |

FOREIGN PATENT DOCUMENTS

| | | |
|---|---|---|
| JP | 2001-500492 A | 3/1998 |
| JP | 2003-503312 A | 1/2003 |
| JP | 2003-506411 A | 2/2003 |
| JP | 2004 155695 A | 6/2004 |
| JP | 2006-347951 A | 12/2006 |
| JP | 2007-537699 A | 12/2007 |
| JP | 2009-517376 A | 4/2009 |
| JP | 2015-508406 | 7/2013 |
| RU | 2019103805 A | 9/2020 |
| WO | WO 1998/09985 A2 | 3/1998 |
| WO | WO 2000/068263 A2 | 11/2000 |
| WO | WO 2001/010457 A2 | 2/2001 |
| WO | WO 2002/016408 A2 | 2/2002 |
| WO | WO 2002/092566 A1 | 11/2002 |
| WO | WO 2015/004430 A1 | 1/2015 |
| WO | WO 2018/033724 A1 | 2/2018 |

OTHER PUBLICATIONS

Unal et al. ('Vital:Viterbi algorithm for de novo peptide design' Plos one v5 Jun. 2010 pp. e10926 pp. 1-15) (Year: 2010).*
Duraes et al. ('Old drugs as new treatments for neurodegenerative diseases' Pharmaceuticals v11 2018 pp. 1-21) (Year: 2018).*
Chai et al. ('Peptides from hydrolysate of lantern fish (*Benthosema pterotum*) proved neuroprotective in vitro and in vivo' Journal of Functional Foods v24 2016 pp. 438-449) (Year: 2016).*
Musiek et al. ('Sleep, circadian rhythms, and the pathogenesis or Alzheimer Disease' Experimental and Molecular Medicine v47 2015 pp. 1-8) (Year: 2015).*
International Search Report and the Written Opinion of PCT/GB2017/052407 dated Nov. 7, 2017, 12 pages.
Sivertsen et al., "Short Cationic Antimicrobial Peptides Bind To Human Alpha-1 Acid Glycoprotein With No Implications For The In Vitro Bioactivity", J. Mol. Recognit., vol. 26, 2013, pp. 461-469; XP-002774978.
Chaki et al., "Involvement Of The Melanocortin $MC_4$ Receptor In Stress-Related Behavion In Rodents", European Journal Of Pharmacology, vol. 474, 2003, pp. 95-101; XP-002774979.
Japanese Patent Application No. 2019-509482, dated Aug. 17, 2021, with translation, 8 pages.

* cited by examiner

*Primary Examiner* — Ronald T Niebauer
(74) *Attorney, Agent, or Firm* — SQUIRE PATTON BOGGS (US) LLP

(57) ABSTRACT

The invention relates to neurodegenerative disorders, and in particular to novel peptides, peptidomimetics, compositions, therapies and methods for treating such conditions, for example Alzheimer's disease.

7 Claims, 35 Drawing Sheets
Specification includes a Sequence Listing.

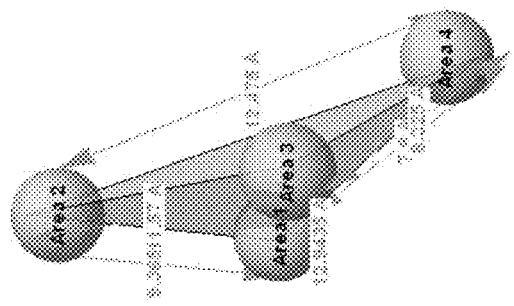
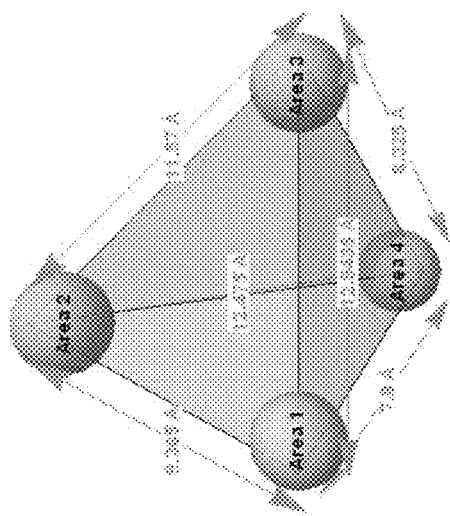
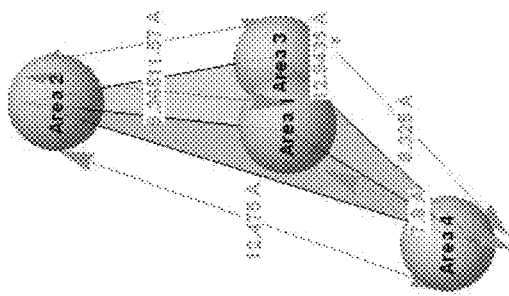
Figure 1a

Figure 7

Area 1  Trp > Arg ~ His ~ Amide > Lys > N-ter ~ Phe
  28%    17%         11%   6%

Area 2  Lys ~ Met > None ~ His ~ Trp > Phe ~ Amide ~ N-ter ~ Arg ~ Ser ~ Tyr
  17%      11%              6%

Area 3  Tyr > Phe > Glu ~ His > Met ~ N-ter ~ Arg ~ Ser ~ Trp
  33%  17%   11%        6%

Area 4  No binding > His ~ Met ~ Trp > Lys ~ Arg
  56%           11%        6%

Figure 8

| | | | | | | | | | | |
|---|---|---|---|---|---|---|---|---|---|---|
| Area 1 | Trp 28% | > | His 22% | > | N-ter 16% | > | Tyr 9% | > | None ~ Lys 6% | > | Ala ~ Glu ~ Arg ~ Amide 3% |

| Area 2 | No binding 34% | > | Trp ~ Lys ~ His 13% | > | Phe ~ Arg 6% | > | Glu ~ Met ~ Amide ~ N-ter ~ Ser 3% |

| Area 3 | Tyr 34% | > | Phe 16% | > | His 13% | > | None ~ C-ter ~ Trp 6% | > | Met ~ Amide ~ N-ter ~ Arg ~ Ser ~ Val 3% |

| Area 4 | None 28% | > | Met 19% | > | His 16% | > | Arg ~ Trp 9% | > | Lys 6% | > | Glu ~ Phe ~ N-ter ~ Val 3% |

Figure 13 (cont)
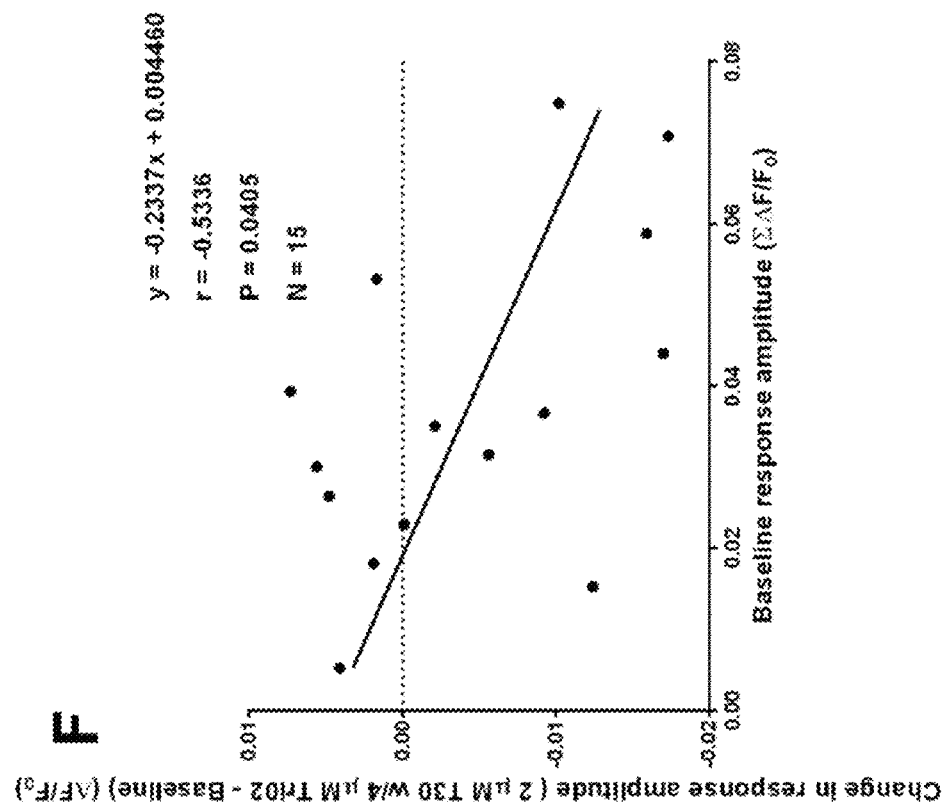
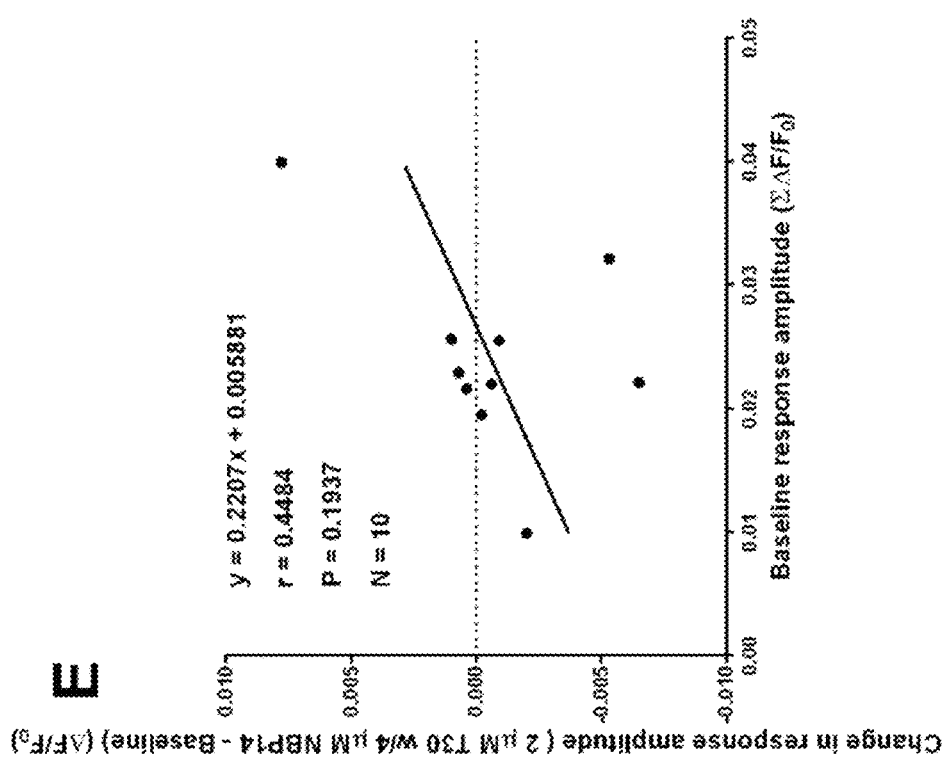

Figure 27A Figure 27B
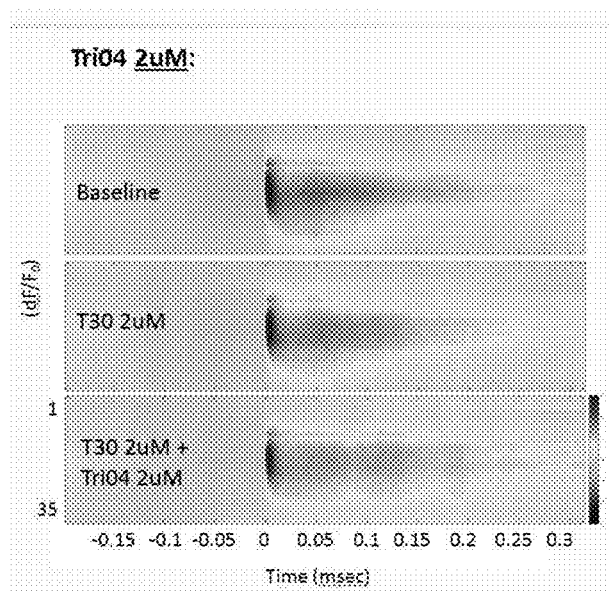
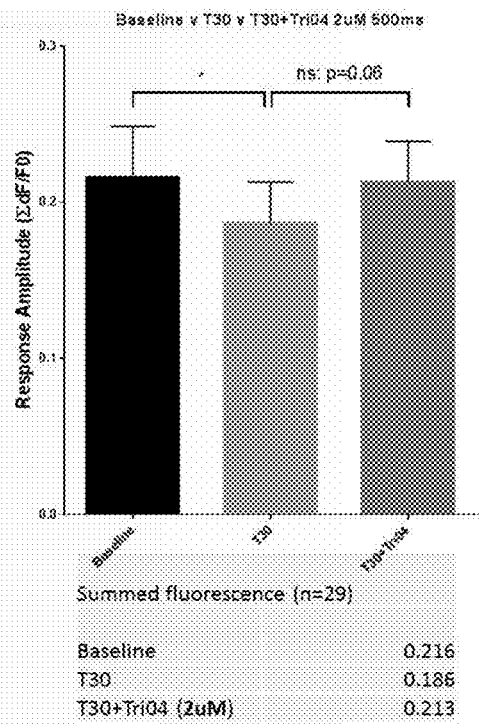
Figure 28
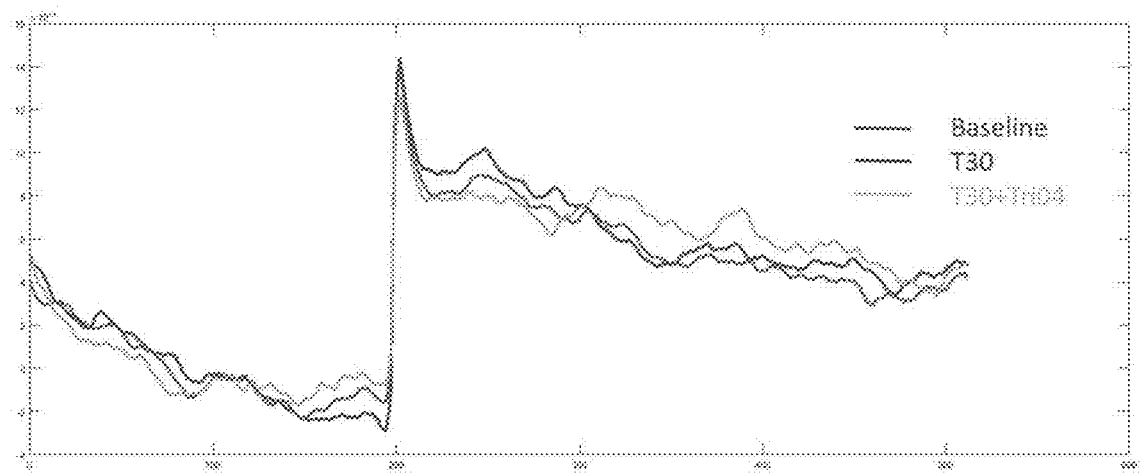

Summed fluorescence
(n=20)

Baseline        0.209

T30             0.171

T30+Tri04
(4uM)           0.193

MODIFIED PEPTIDES FOR USE IN TREATING NEURODEGENERATIVE DISORDERS

The present application is the U.S. National Stage of International Application No. PCT/GB2017/052407, filed Aug. 16, 2016, which claims the benefit of GB application no. 1613999.0, filed Aug. 16, 2016, and the benefit of GB application no. 1701455.6, filed Jan. 30, 2017, the contents of each of which are incorporated by reference herein in their entireties.

The invention relates to neurodegenerative disorders, and in particular to novel peptides, peptidomimetics, compositions, therapies and methods for treating such conditions, for example Alzheimer's disease.

The inventors have previously proposed that the neurodegenerative process is an aberrantly activated process of development. In support of this hypothesis, a hyper-trophy of the brainstem 'hub' neurons has actually been reported in Alzheimer brains (Bowser et al., 1997, Brain Pathol. 7:723-30). If large areas of this hub are damaged, then more than one neurodegenerative disease will present, as occurs in the frequently seen but never as yet explained cases of co-pathology with Alzheimer's and Parkinson's diseases. Interestingly, all the neurons within the vulnerable hub of Global neurons, despite transmitter heterogeneity, all contain the familiar enzyme acetylcholinesterase (AChE). AChE is therefore present in neurons where it would be unable to perform its normal function, since such sub-groups of cells as the noradrenergic locus coeruleus, the dopaminergic substantia nigra, or the serotonergic raphe nuclei, in no cases contain the usual substrate, acetylcholine. A further unexpected deviation from its normal, enzymatic role is that the AChE is actually released from Global neurons, presumably as some kind of inter-cellular messenger in its own right. In general, AChE is now widely and well-established as a signalling molecule that has trophic activity in a diverse variety of situations in both neural and non-neural tissue.

The inventors have previously shown that AChE, operating as a trophic agent independent of its enzymatic action, does indeed trigger calcium entry into neurons. It is possible therefore that within Global neurons, AChE has a dual non-classical action that ranges along a trophic-toxic axis, depending on amount, duration of availability and, most significantly, age. If standard neurons are damaged in adulthood, as in a stroke, others will compensate functionally. In contrast, Global neurons will respond by calling on their trophic resources in an attempt to regenerate. But because the subsequent calcium influx will be lethal in the older, mature cells, the resulting damage will trigger further attempts to compensate in a pernicious cycle that characterises neurodegeneration.

Acetylcholinesterase (AChE) is expressed at different stages of development in various forms, all of which have identical enzymatic activity, but which have very different molecular composition. The 'tailed' (T-AChE) is expressed at synapses and the inventors have previously identified two peptides that could be cleaved from the C-terminus, one referred to as "T14", within the other which is known as "T30", and which both have strong sequence homology to the comparable region of β-amyloid. The AChE C-terminal peptide "T14" has been identified as being the salient part of the AChE molecule responsible for its range of non-hydrolytic actions. The synthetic 14 amino acids peptide analogue (i.e. "T14"), and subsequently the larger, more stable, and more potent amino acid sequence in which it is embedded (i.e. "T30") display actions comparable to those reported for 'non-cholinergic' AChE, where the inert residue within the T30 sequence (i.e. "T15") is without effect.

Acute effects of T14 and T30 are that they:—(i) modulate calcium entry into neurons in brain slices over time scales from milliseconds to hours; (ii) compromise cell viability in PC 12 cells and also in neuronal organotypic cultures in vitro; (iii) modulate 'compensatory' calcium-induced AChE release from neurons and PC 12 cells; (iv) activate calcium currents in oocytes and neurons in brain slices; (v) synergise with amyloid in toxic effects; and (vi) are involved in amyloid precursor protein production and amyloid beta (A13) peptide release. Chronic effects of T14 and T30 are that they:—(i) reduce neuron growth; (ii) induce apoptosis; (iii) increase AChE release; (iv) bind to and modulate α7 nicotinic-receptor (α-7nChR receptor); and (v) enhance expression of the α7 receptor on the cell surface over 24 hours, thereby providing a feedforward mechanism for further toxicity.

Since T14 and T30 are more selective than β-amyloid in inducing toxicity and are also synergistic with amyloid exacerbating toxicity, it has been postulated that any agent which blocks the toxic effects of T14 or T30 would also reduce the less selective and subsequent toxic effect of amyloid. The inventor has previously shown that T30 and T14 peptides bind to an allosteric site on the α7 nicotinic-receptor to induce a spectrum of trophic-toxic effects. This receptor is co-expressed with AChE during critical periods of brain development as well as showing a closely parallel distribution in the adult brain, and is one of the most powerful calcium ionophores in the brain. It can also function independent of cholinergic transmission, since choline (derived from diet) can serve as an alternative primary ligand. Moreover, this receptor has already been implicated in Alzheimer's disease as one of the targets for the current therapy galanthamine (Reminyl®), as well as being linked to the actions of amyloid.

However, the efficacy of galanthamine has proved limited, whilst other α7 nicotinic acetylcholine receptor antagonists are still in clinical trials. Not only does galanthamine have non-specific effects on other receptors, as well as inhibiting AChE, but it has a low affinity for the α7 nicotinic-receptor (i.e. only 10 µM) compared to that of T30 and T14, which have much higher affinities for the α7 nicotinic-receptor (i.e. 5 nM). Hence if, in an Alzheimer's brain, the endogenous equivalent of the T30 peptide is already occupying the respective receptor site, galanthamine would need to be given at non-physiological, high doses with inevitable side effects and most importantly, questionable efficacy.

The inventors have previously shown, in WO 2015/004430, that cyclic polypeptides comprising an amino acid sequence derived from the C-terminus of acetylcholinesterase (AChE) selectively inhibit the non-classical effects of AChE (i.e. the effects of AChE that are independent of its enzymatic activity) and/or its terminal peptide in vitro, and therefore can be used to treat neurodegenerative disorders. For example, the cyclic peptide referred to as "NBP14" (i.e. cyclic T14 peptide), has been shown to be particularly active, as it acts as an allosteric modulator of the .alpha.7 nicotinic-receptor antagonizing the effects of AChE peptides and Amyloid beta. It was shown to protect cells from linear T14, T30 and.beta.-amyloid toxicity, and it blocks compensatory AChE release induced by the toxicity of linear T14 and T30. In addition, they observed that cyclic NBP14 given alone has no significant effects on $Ca^{2+}$concentrations in rat brain slices, but blocks the effects of β-amyloid. However, in spite of the activity exhibited by cyclic NBP14, due to its size, there are some concerns of its ability to cross the blood-brain barrier for use as a therapeutic.

Therefore, there is an ongoing need to provide improved medicaments for the treatment of neurodegenerative disorders, such as Alzheimer's disease and Parkinson's disease.

The inventors continued their previous work described in WO 2015/004430 in which they demonstrated that cyclic NBP-14 protects against the T30 toxic action and beta-amyloid production. They conducted an in silico study in order to design novel peptides and peptidomimetics, which would exhibit affinity for the α-7nChR receptor, and which would therefore block binding to its active site by the endogenous toxic T30 peptide. Following analysis of a vast number of possible candidate compounds, they have now determined the chemical functionalities relevant for the protection against the T30 toxic action and beta-amyloid production by looking at the interaction between the receptor, and cyclic NBP-14. Based on these experiments, the inventors have designed, synthesised and tested several candidate compounds, which have been shown to have surprising therapeutic utility for treating neurodegenerative disorders.

In accordance with a first aspect of the invention, there is provided a compound of Formula (I), (II), (III), (IV), (V) or (VI):

Formula (I)
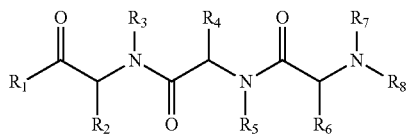

Formula (II)
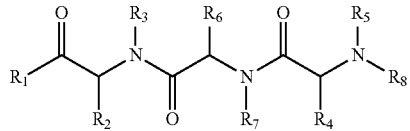

Formula (III)
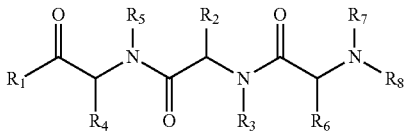

Formula (IV)
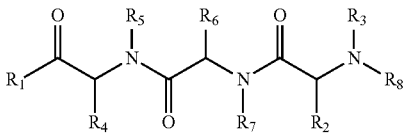

Formula (V)
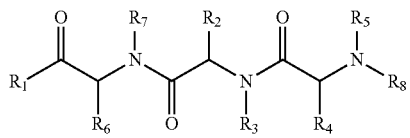

Formula (VI)
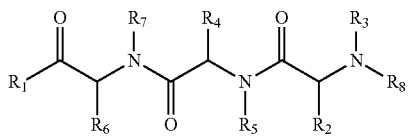

wherein:

$R_1$ is —$NR_9R_{10}$ or —OH;

$R_2$ is

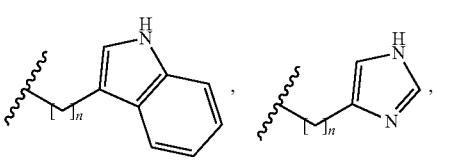

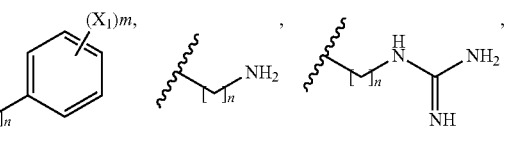

$R_3$ is —H or a $C_{1-5}$ straight or branched alkyl or alkenyl;

$R_4$ is

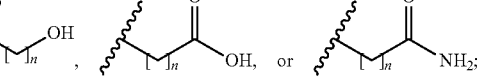

$R_5$ is —H or a $C_{1-5}$ straight or branched alkyl or alkenyl; or $R_4$ and $R_5$ together with the nitrogen and carbon to which they are bonded form a five membered ring substituted by —OH or —$NH_2$;

$R_6$ is

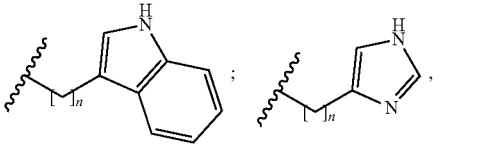

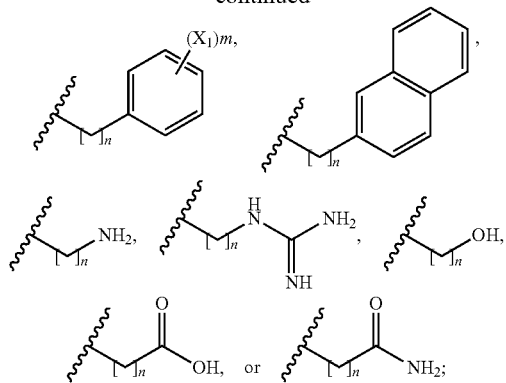

$R_7$ is —H or a $C_{1-5}$ straight or branched alkyl or alkenyl;
$R_8$ is —H; a $C_{1-5}$ straight or branched alkyl or alkenyl or

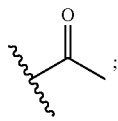

$X_1$ is —$NR_9R_{10}$, —OH or

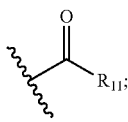

the or each $R_9$ and $R_{10}$ are independently —H or a $C_{1-5}$ straight or branched alkyl or alkenyl;
$R_{11}$ is —$NH_2$, —OH or an aryl group;
the or each m is independently between 0 and 5; and
each n is independently between 0 and 10;
or a pharmaceutically acceptable salt, solvate, tautomeric form, or polymorphic form thereof for use in therapy.

As described in the Examples, and illustrated in FIGS. 9, 10 and 26, compounds according to the invention are preferably configured to protect a subject treated therewith against the toxic effects of the T30 peptide by reducing calcium influx and/or acetylcholinesterase activity. In addition, compounds according to the invention are preferably configured to protect a subject against beta amyloid production. Accordingly, the inventors have also found that compounds of formula (I), (II), (III), (IV), (V) and (VI) are useful in the treatment of neurodegenerative disorders.

Thus, in a second aspect, there is provided a compound of formula (I), (II), (III), (IV), (V) or (VI) or a pharmaceutically acceptable salt, solvate, tautomeric form or polymorphic form thereof, for use in treating, ameliorating, or preventing a neurodegenerative disorder.

Furthermore, in a third aspect, there is provided a method of treating, ameliorating or preventing a neurodegenerative disorder, the method comprising administering, to a subject in need of such treatment, a therapeutically effective amount of a compound of formula (I), (II), (III), (IV), (V) or (VI) or a pharmaceutically acceptable salt, solvate, tautomeric form or polymorphic form thereof.

The neurodegenerative disorder which is treated is preferably one which is characterised by the damage or death of 'Global' neurons. For example, the neurodegenerative disorder may be selected from a group consisting of Alzheimer's disease; Parkinson's disease; Huntington's disease; Motor Neurone disease; Spinocerebellar type 1, type 2, and type 3; Amyotrophic Lateral Sclerosis (ALS); schizophrenia; Lewy-body dementia; and Frontotemporal Dementia.

Preferably, the neurodegenerative disorder, which is treated, is Alzheimer's disease, Parkinson's disease, or Motor Neurone disease. Most preferably, the neurodegenerative disorder, which is treated with the peptide, derivative or analogue thereof according to the first aspect, is Alzheimer's disease.

It may be understood that the term "salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Salts may further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

It may be understood that the term "solvate" refers to a compound provided herein or a salt thereof, that further includes a stoichiometric or non-stoichiometric amount of solvent bound by non-covalent intermolecular forces. Where the solvent is water, the solvate is a hydrate.

It may be appreciated that an aryl group refers to a substituent derived from an aromatic ring. The aryl group may be a C6-C12 aryl group. Preferably, the aryl group is phenyl, biphenyl or naphthyl.

Most preferably, the compound has Formula (Ia), (IIa), (IIIa), (IVa), (Va) or (VIa):

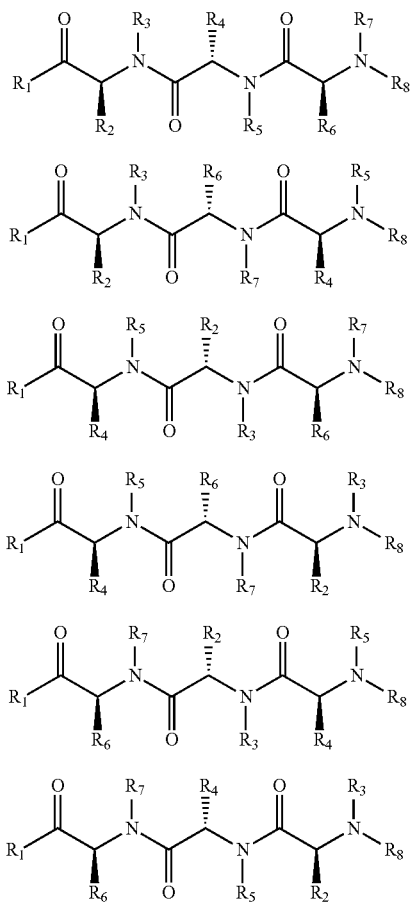

Alternatively, the compound may have Formula (Ib), (IIb), (IIIb), (IVb), (Vb) or (VIb):

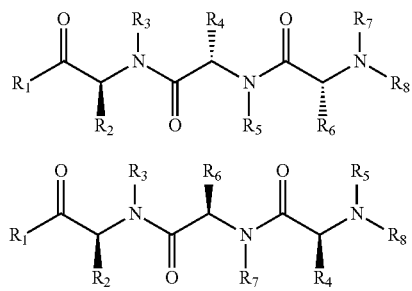
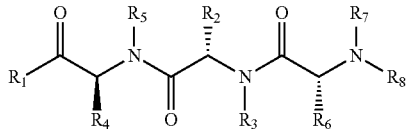
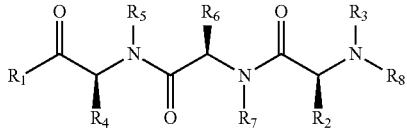
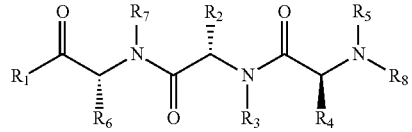
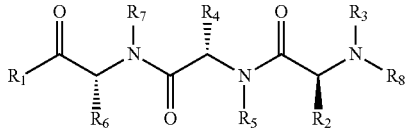

$R_1$ may be —OH. However, preferably, $R_1$ is —$NR_9R_{10}$, more preferably $R_1$ is —$NR_9H$, and most preferably $R_1$ is —$NH_2$.

Preferably, in embodiments where $R_2$ is

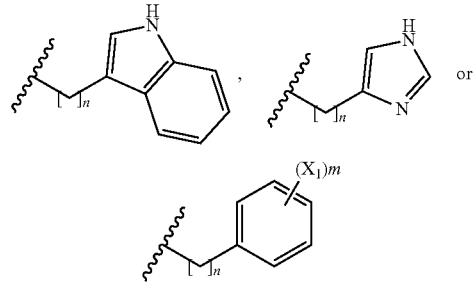

then n is preferably between 1 and 5. Accordingly, n may be 1, 2, 3, 4 or 5, and most preferably n is 1.

Preferably, in embodiments where $R_2$ is

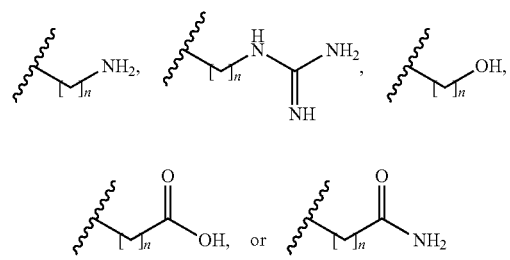

then n is between 1 and 7, and is more preferably between 2 and 6. Accordingly, n may be 2, 3, 4, 5 or 6, and is preferably n is 3 or 4 and is most preferably 4.

Preferably, $R_2$ is

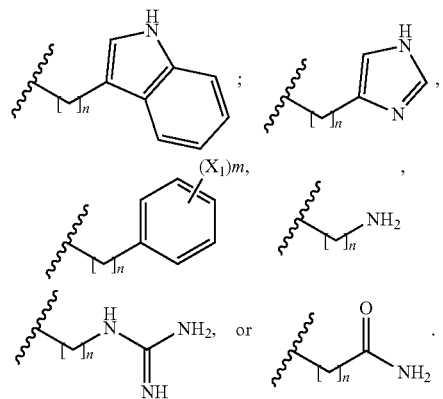

More preferably, $R_2$ is

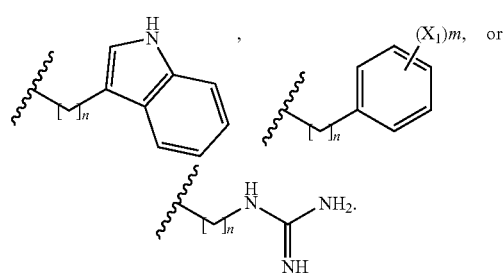

It will be appreciated that in embodiments where $R_2$ is

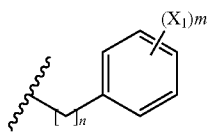

then m may be 0, 1, 2, 3, 4 or 5. Preferably m is 1. Preferably, $X_1$ is in the para position.

In a preferred embodiment $R_2$ is

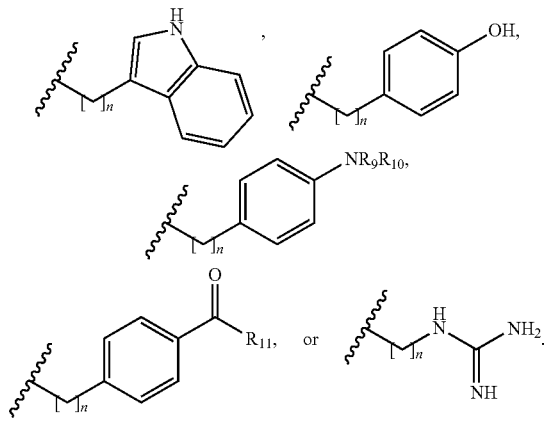

Preferably, in embodiments when $R_2$ is

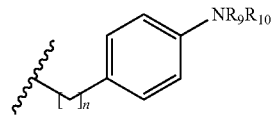

then at least one of $R_9$ or $R_{10}$ is —H, and most preferably $R_9$ or $R_{10}$ are both —H.

Preferably, in embodiments when $R_2$ is then

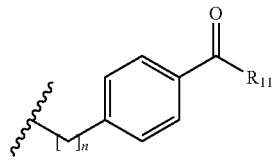

$R_{11}$ is aryl, and most preferably phenyl.

In a preferred embodiment, $R_2$ is

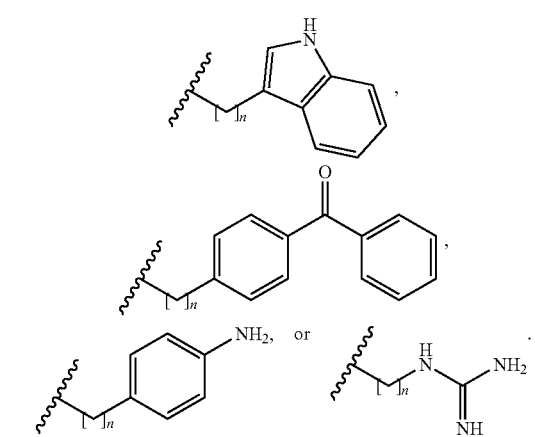

In a most preferred embodiment, $R_2$ is

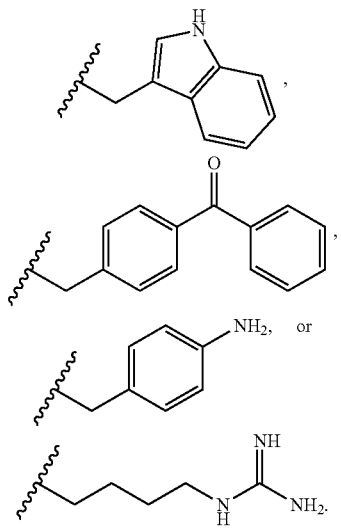

It will be appreciated that $R_3$ may be a methyl, ethyl, propyl, butyl or pentyl group. Preferably, $R_3$ is methyl. However, in a more preferred embodiment, $R_3$ is —H.

In embodiments where $R_4$ is

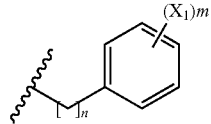

then n is preferably between 1 and 5. Accordingly, n may be 1, 2, 3, 4 or 5, and preferably n is 1.

In embodiments where $R_4$ is

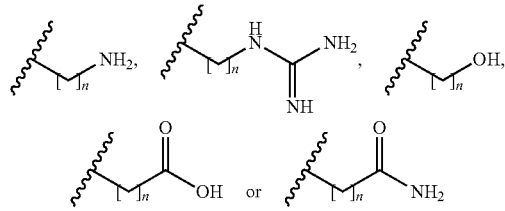

then n is preferably between 1 and 7, and is more preferably between 2 and 6. Accordingly, n may be 2, 3, 4, 5 or 6, and is preferably n is 3 or 4.

In one embodiment, $R_4$ is preferably

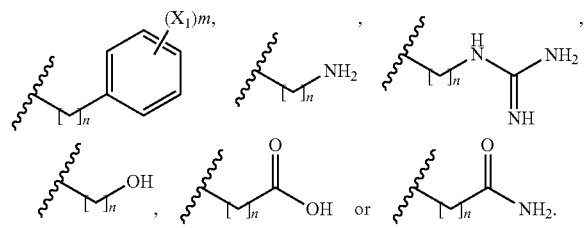

More preferably, $R_4$ is

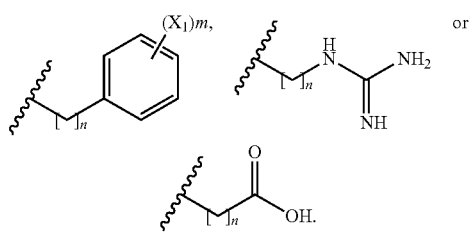

It will be appreciated that in embodiments where $R_4$ is

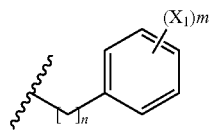

then m may be 0, 1, 2, 3, 4 or 5. Preferably m is 1. Preferably, $X_1$ is in the para position.

Preferably, $R_4$ is

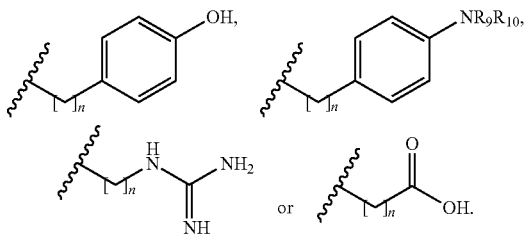

More preferably, $R_4$ is

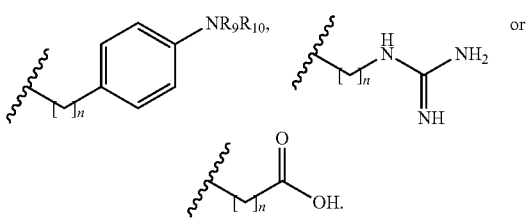

Preferably, in embodiments when $R_4$ is

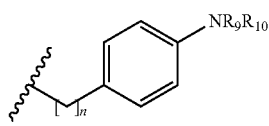

then at least one of $R_9$ or $R_{10}$ is —H, and most preferably both $R_9$ or $R_{10}$ are —H.

Accordingly, $R_4$ is preferably

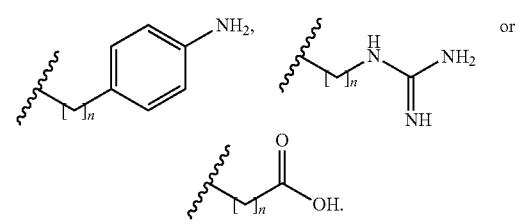

More preferably, $R_4$ is

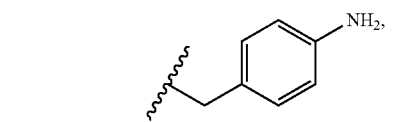

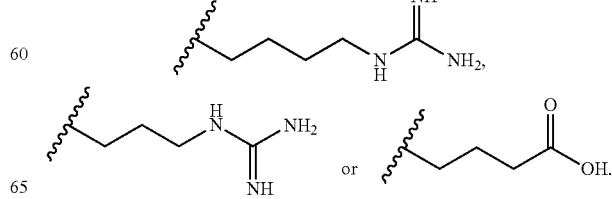

It will be appreciated that R₅ may be a methyl, ethyl, propyl, butyl or pentyl group. Preferably, R₅ is methyl. However, in a more preferred embodiment, R₅ is —H.

In an alternative embodiment, R₄ and R₅ together with the nitrogen and carbon to which they are bonded form a five membered ring substituted by —OH or —NH₂. Accordingly, R₄ and R₅ together with the nitrogen and carbon to which they are bonded may define the following structure:

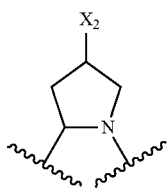

wherein X₂ is —OH or —NH₂.

Preferably, R₄ and R₅ together with the nitrogen and carbon to which they are bonded may define the following structure:

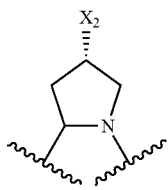

Preferably, R₄ and R₅ together with the nitrogen and carbon to which they are bonded may define the following structure:

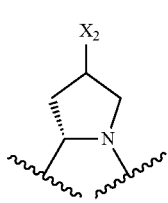

More preferably, R₄ and R₅ together with the nitrogen and carbon to which they are bonded may define the following structure:

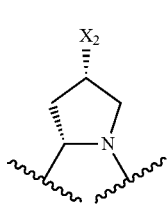

Preferably, X₂ is —NH₂.

Even more preferably, R₄ and R₅ together with the nitrogen and carbon to which they are bonded define the following structure:

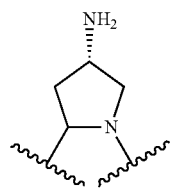 [SMILES: *C1C[C@H](N)CN1*]

Even more preferably, R₄ and R₅ together with the nitrogen and carbon to which they are bonded define the following structure:

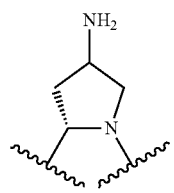

Most preferably, R₄ and R₅ together with the nitrogen and carbon to which they are bonded define the following structure:

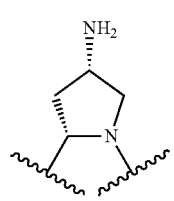 [SMILES: *[C@@H]1C[C@H](N)CN1*]

In embodiments where R₆ is

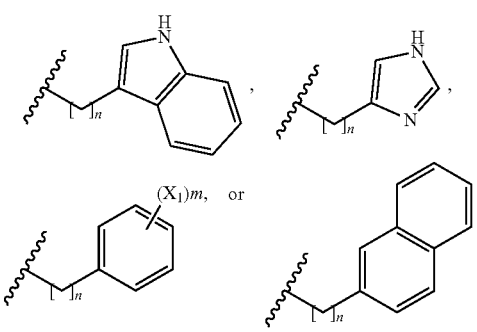

then n is preferably between 1 and 5. Accordingly, n may be 1, 2, 3, 4 or 5, and preferably n is 1.

In embodiments where R₆ is

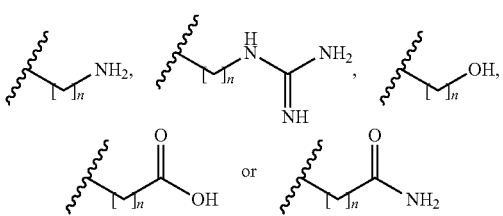

then n is preferably between 1 and 7, and is more preferably between 2 and 6. Accordingly, n may be 2, 3, 4, 5 or 6, preferably n is 3 or 4, and most preferably n is 3.

Preferably, $R_6$ is

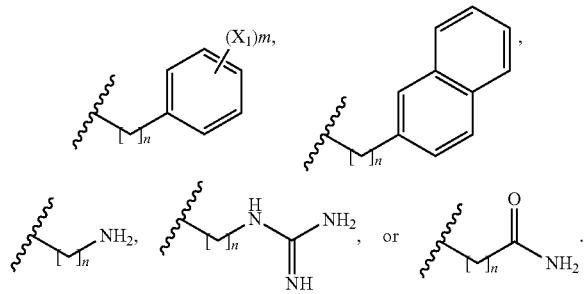

More preferably, $R_6$ is

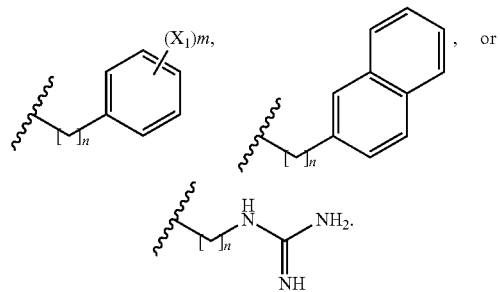

It will be appreciated that in embodiments where $R_6$ is

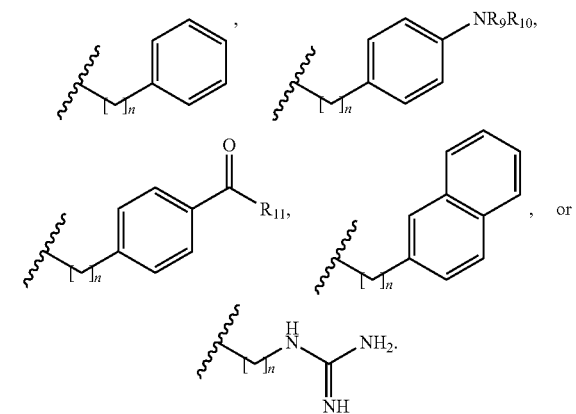

then m may be 0, 1, 2, 3, 4 or 5. Preferably, m is 0. More preferably, m is 1. Preferably, $X_1$ is in the para position.

In a preferred embodiment $R_6$ is

Preferably, in embodiments when $R_6$ is

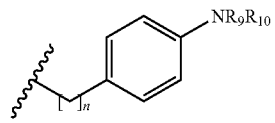

then at least one of $R_9$ or $R_{10}$ is —H, and most preferably both $R_9$ or $R_{10}$ are —H.

Preferably, in embodiments when $R_6$ is

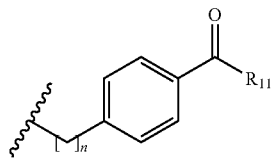

then $R_{11}$ is aryl, and most preferably phenyl.

In a preferred embodiment, $R_6$ is

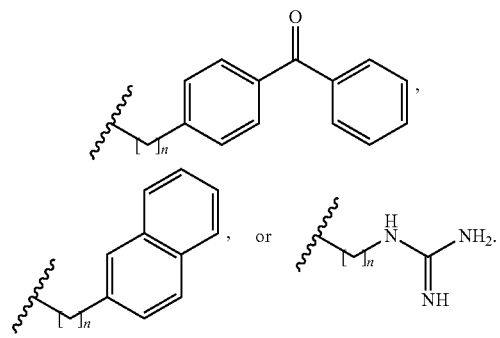

In a most preferred embodiment, $R_6$ is

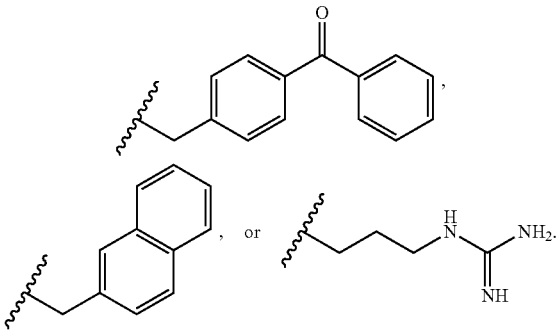

It will be appreciated that $R_7$ may be a methyl, ethyl, propyl, butyl or pentyl group. Preferably, $R_7$ is methyl. However, in a more preferred embodiment, $R_7$ is —H.

In one preferred embodiment $R_8$ is —H. However, in a more preferred embodiment $R_8$ is

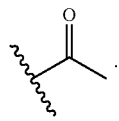

In a preferred embodiment, there is provided a compound of Formula (I), (II), (III), (IV), (V) or (VI), wherein:
$R_2$ is

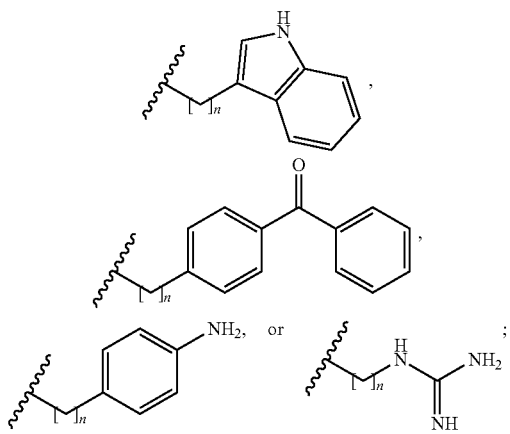

$R_3$ is H or a $C_{1-5}$ straight or branched alkyl or alkenyl;
$R_4$ is

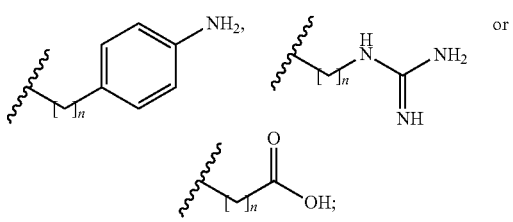

$R_5$ is H or a $C_{1-5}$ straight or branched alkyl or alkenyl; or $R_4$ and $R_5$ together with the nitrogen and carbon to which they are bonded define the following structure:

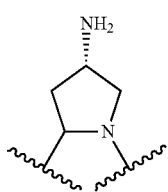 [SMILES: *C1C[C@H](N)CN1*]

$R_6$ is

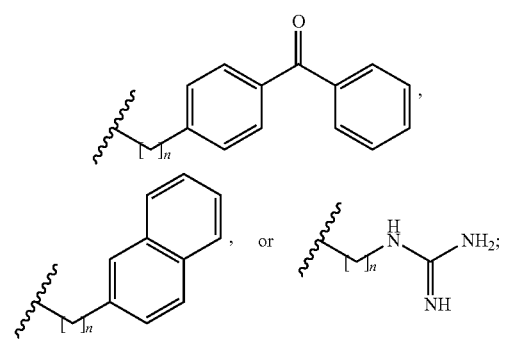

and
$R_7$ is H or a $C_{1-5}$ straight or branched alkyl or alkenyl.

Preferably, $R_3$ is H and $R_7$ is H.

In some embodiments, $R_3$ is H, $R_4$ and $R_5$ together with the nitrogen and carbon to which they are bonded define the following structure:

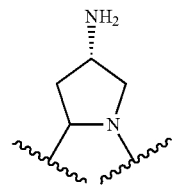

and $R_7$ is H.

In some alternative embodiments, $R_3$ is H, $R_5$ is H and $R_7$ is H.

In a more preferred embodiment, there is provided a compound of Formula (I), (II), (III), (IV), (V) or (VI), wherein:
$R_2$ is

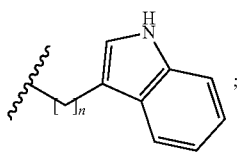

$R_3$ is H or a $C_{1-5}$ straight or branched alkyl or alkenyl;
$R_4$ is

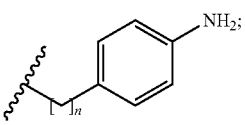

$R_5$ is H or a $C_{1-5}$ straight or branched alkyl or alkenyl; or
$R_6$ is

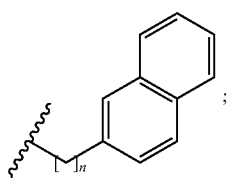

and
$R_7$ is H or a $C_{1-5}$ straight or branched alkyl or alkenyl.

Preferably, the compound is a compound of Formula (Ia), (IIa), (IIIa), (IVa), (Va) or (VIa).

Preferably, the compound is a compound of Formula (I), and more preferably a compound of Formula (Ia).

Preferably, $R_3$ is H, $R_5$ is H and $R_7$ is H.

In an alternative more preferred embodiment, there is provided a compound of Formula (I), (II), (III), (IV), (V) or (VI), wherein:

$R_2$ is

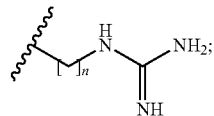

$R_3$ is H or a $C_{1-5}$ straight or branched alkyl or alkenyl;

$R_4$ and $R_5$ together with the nitrogen and carbon to which they are bonded define the following structure:

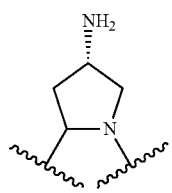 [SMILES: *C1C[C@H](N)CN1*]

$R_6$ is

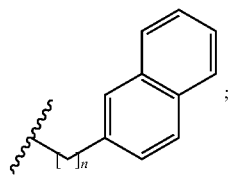

and $R_7$ is H or a $C_{1-5}$ straight or branched alkyl or alkenyl.

Preferably, the compound is a compound of Formula (Ia), (IIa), (IIIa), (IVa), (Va) or (VIa).

Preferably, the compound is a compound of Formula (I), and more preferably a compound of Formula (Ia).

Preferably, $R_3$ is H and $R_7$ is H.

In an alternative more preferred embodiment, there is provided a compound of Formula (I), (II), (III), (IV), (V) or (VI), wherein:

$R_2$ is

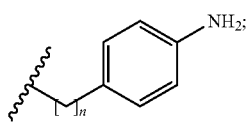

$R_3$ is H or a $C_{1-5}$ straight or branched alkyl or alkenyl;

$R_4$ is

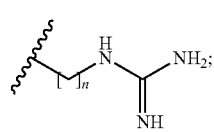

$R_5$ is H or a $C_{1-5}$ straight or branched alkyl or alkenyl; or $R_6$ is

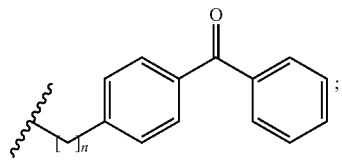

and $R_7$ is H or a $C_{1-5}$ straight or branched alkyl or alkenyl.

Preferably, the compound is a compound of Formula (Ia), (IIa), (IIIa), (IVa), (Va) or (VIa).

Preferably, the compound is a compound of Formula (I), and more preferably a compound of Formula (Ia).

Preferably, $R_3$ is H, $R_5$ is H and $R_7$ is H.

In a further more preferred embodiment, there is provided a compound of Formula (I), (II), (III), (IV), (V) or (VI), wherein:

$R_2$ is

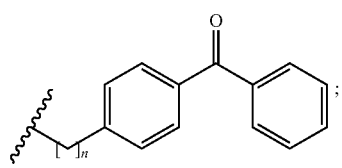

$R_3$ is H or a $C_{1-5}$ straight or branched alkyl or alkenyl;

$R_4$ is

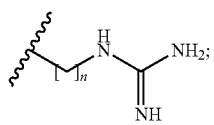

$R_5$ is H or a $C_{1-5}$ straight or branched alkyl or alkenyl; or $R_6$ is

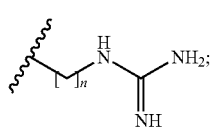

and $R_7$ is H or a $C_{1-5}$ straight or branched alkyl or alkenyl.

Preferably, the compound is a compound of Formula (Ib), (IIb), (IIIb), (IVb), (Vb) or (VIb).

Preferably, the compound is a compound of Formula (I), and more preferably a compound of Formula (Ib).

Preferably, $R_3$ is H, $R_5$ is H and $R_7$ is H.

In a further more preferred embodiment, there is provided a compound of Formula (I), (II), (III), (IV), (V) or (VI), wherein:

$R_2$ is

[structure: benzyl-phenyl ketone with $[\ ]_n$ linker]

;

$R_3$ is H or a $C_{1-5}$ straight or branched alkyl or alkenyl;
$R_4$ is

[structure: $-[\ ]_n-COOH$]

;

$R_5$ is H or a $C_{1-5}$ straight or branched alkyl or alkenyl; or
$R_6$ is

[structure: $-[\ ]_n-NH-C(=NH)-NH_2$ guanidine]

;

and
$R_7$ is H or a $C_{1-5}$ straight or branched alkyl or alkenyl.

Preferably, the compound is a compound of Formula (Ia), (IIa), (IIIa), (IVa), (Va) or (VIa).

Preferably, the compound is a compound of Formula (I), and more preferably a compound of Formula (Ia).

Preferably, $R_3$ is H, $R_5$ is H and $R_7$ is H.

Preferably, $R_1$ is —OH and $R_8$ is H. More preferably, $R_1$ is $NH_2$ and $R_8$ is

[structure: acetyl group]

.

In an even more preferred embodiment, there is provided a compound of Formula (I), (II), (III), (IV), (V) or (VI), wherein:

$R_2$ is

[structure: indolyl-methyl / tryptophan side chain]

,

[structure: benzyl-phenyl ketone]

,

[structure: 4-aminobenzyl group with $NH_2$], or

[structure: butyl-guanidine side chain]

;

$R_3$ is H or a $C_{1-5}$ straight or branched alkyl or alkenyl;
$R_4$ is

[structure: 4-aminobenzyl],

[structure: butyl-guanidine],

[structure: propyl-guanidine] or [structure: $-CH_2CH_2CH_2-COOH$];

$R_5$ is H or a $C_{1-5}$ straight or branched alkyl or alkenyl; or
$R_4$ and $R_5$ together with the nitrogen and carbon to which they are bonded define the following structure:

[structure: 4-aminopyrrolidine]

$R_6$ is

[structure: benzyl-phenyl ketone],

[structure: naphthylmethyl], or [structure: butyl-guanidine]

;

and
$R_7$ is H or a $C_{1-5}$ straight or branched alkyl or alkenyl.

Preferably, $R_3$ is H and $R_7$ is H.

In some embodiments, $R_3$ is H, $R_4$ and $R_5$ together with the nitrogen and carbon to which they are bonded define the following structure:

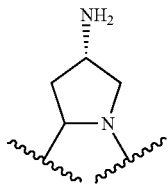 [SMILES: *C1C[C@H](N)CN1*]

and $R_7$ is H.

In some alternative embodiments, $R_3$ is H, $R_5$ is H and $R_7$ is H.

In a more preferred embodiment, there is provided a compound of Formula (I), (II), (III), (IV), (V) or (VI), wherein:

$R_2$ is

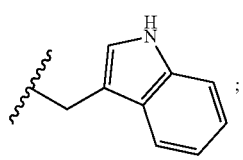 [SMILES: *Cc1c[nH]c2ccccc12]

$R_3$ is H;

$R_4$ is

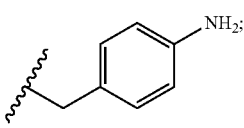 [SMILES: *Cc1ccc(N)cc1]

$R_5$ is H; or $R_6$ is

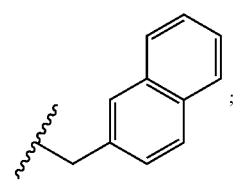 [SMILES: *Cc1ccc2ccccc2c1]

and $R_7$ is H.

Preferably, the compound is a compound of Formula (Ia), (IIa), (IIIa), (IVa), (Va) or (VIa).

Preferably, the compound is a compound of Formula (I), and more preferably a compound of Formula (Ia).

Preferably, $R_3$ is H, $R_5$ is H and $R_7$ is H.

In an alternative more preferred embodiment, there is provided a compound of Formula (I), (II), (III), (IV), (V) or (VI), wherein:

$R_2$ is

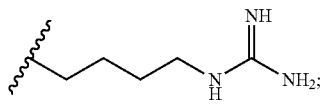 [SMILES: *CCCCNC(=N)N]

$R_3$ is H;

$R_4$ and $R_5$ together with the nitrogen and carbon to which they are bonded define the following structure:

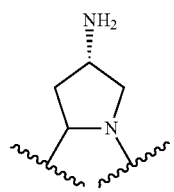 [SMILES: *C1C[C@H](N)CN1*]

$R_6$ is

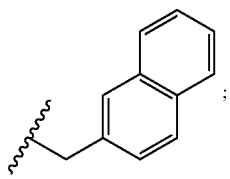 [SMILES: *Cc1ccc2ccccc2c1]

and $R_7$ is H.

Preferably, the compound is a compound of Formula (Ia), (IIa), (IIIa), (IVa), (Va) or (VIa).

Preferably, the compound is a compound of Formula (I), and more preferably a compound of Formula (Ia).

Preferably, $R_3$ is H and $R_7$ is H.

In an alternative more preferred embodiment, there is provided a compound of Formula (I), (II), (III), (IV), (V) or (VI), wherein:

$R_2$ is

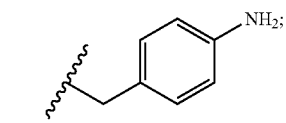 [SMILES: *Cc1ccc(N)cc1]

$R_3$ is H;

$R_4$ is

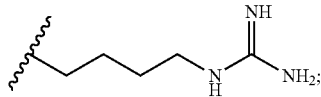 [SMILES: *CCCCNC(=N)N]

$R_5$ is H; or
$R_6$ is

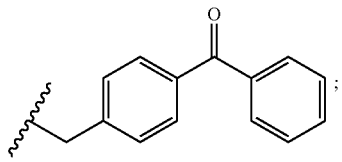 [SMILES: *Cc1ccc(C(=O)c2ccccc2)cc1]

and
$R_7$ is H.

Preferably, the compound is a compound of Formula (Ia), (IIa), (IIIa), (IVa), (Va) or (VIa).

Preferably, the compound is a compound of Formula (I), and more preferably a compound of Formula (Ia).

Preferably, $R_3$ is H, $R_5$ is H and $R_7$ is H.

In a further more preferred embodiment, there is provided a compound of Formula (I), (II), (III), (IV), (V) or (VI), wherein:

$R_2$ is

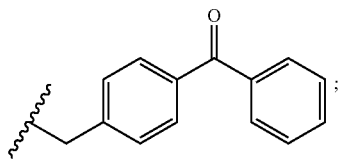 [SMILES: *Cc1ccc(C(=O)c2ccccc2)cc1]

$R_3$ is H;
$R_4$ is

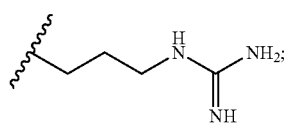

$R_5$ is H; or
$R_6$ is

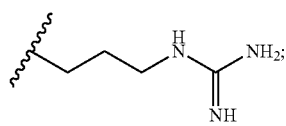 [SMILES: *CCCNC(=N)N]

and
$R_7$ is H.

Preferably, the compound is a compound of Formula (Ib), (IIb), (IIIb), (IVb), (Vb) or (VIb).

Preferably, the compound is a compound of Formula (I), and more preferably a compound of Formula (Ib).

Preferably, $R_3$ is H, $R_5$ is H and $R_7$ is H.

In a further more preferred embodiment, there is provided a compound of Formula (I), (II), (III), (IV), (V) or (VI), wherein:

$R_2$ is

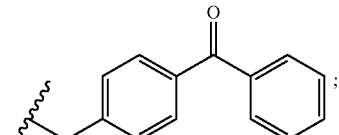

$R_3$ is H;
$R_4$ is

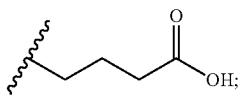 [SMILES: *CCCC(=O)O]

$R_5$ is H; or
$R_6$ is

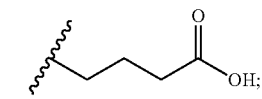

and
$R_7$ is H.

Preferably, the compound is a compound of Formula (Ia), (IIa), (IIIa), (IVa), (Va) or (VIa).

Preferably, the compound is a compound of Formula (I), and more preferably a compound of Formula (Ia).

Preferably, $R_3$ is H, $R_5$ is H and $R_7$ is H.

Preferably, $R_1$ is —OH and $R_8$ is H. More preferably, $R_1$ is $NH_2$ and $R_8$ is

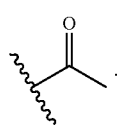 [SMILES: *C(C)=O]

Preferably, the compound is a compound of Formula (101), (102), (103), (104) or (105):

Formula (101)

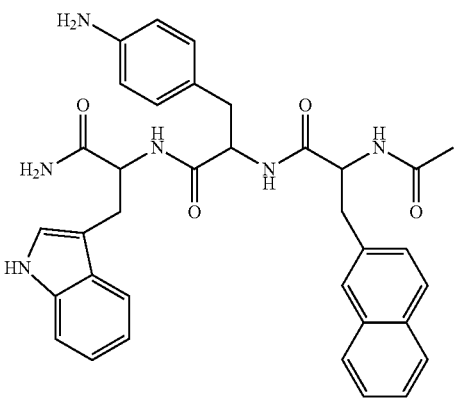

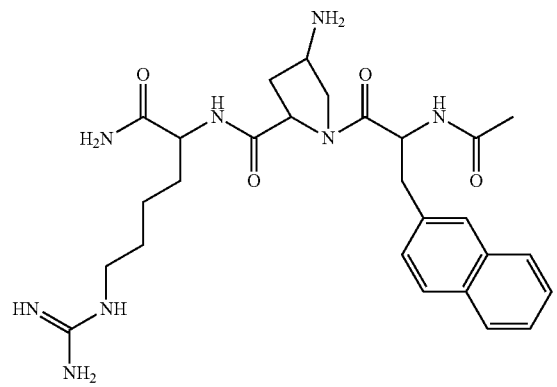
Formula (102)
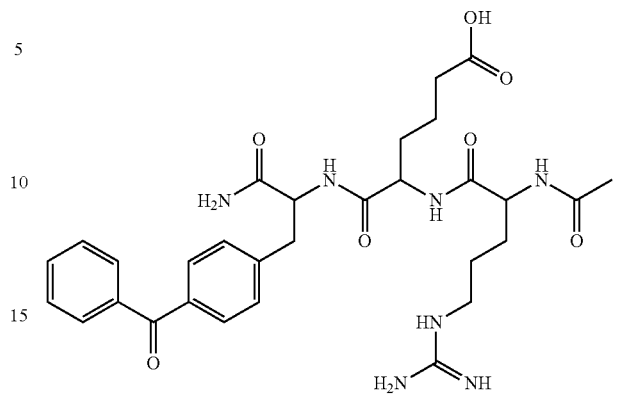
Formula (105)
More preferably, the compound is a compound of Formula (101a), (102a), (103a), (104b) or (105a):
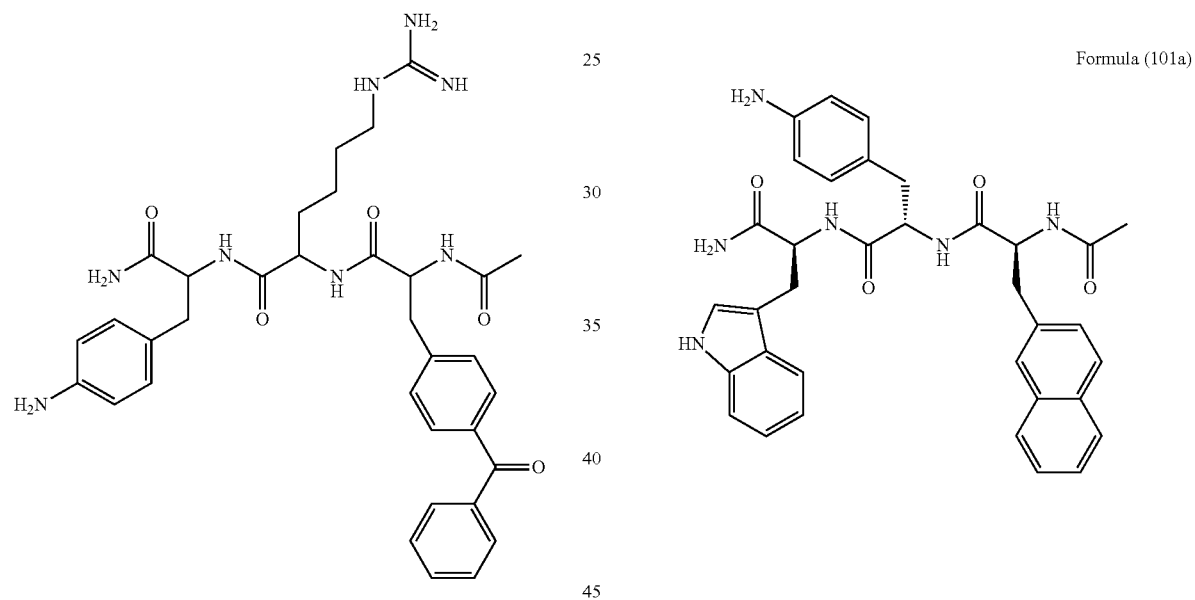
Formula (103)
Formula (101a)
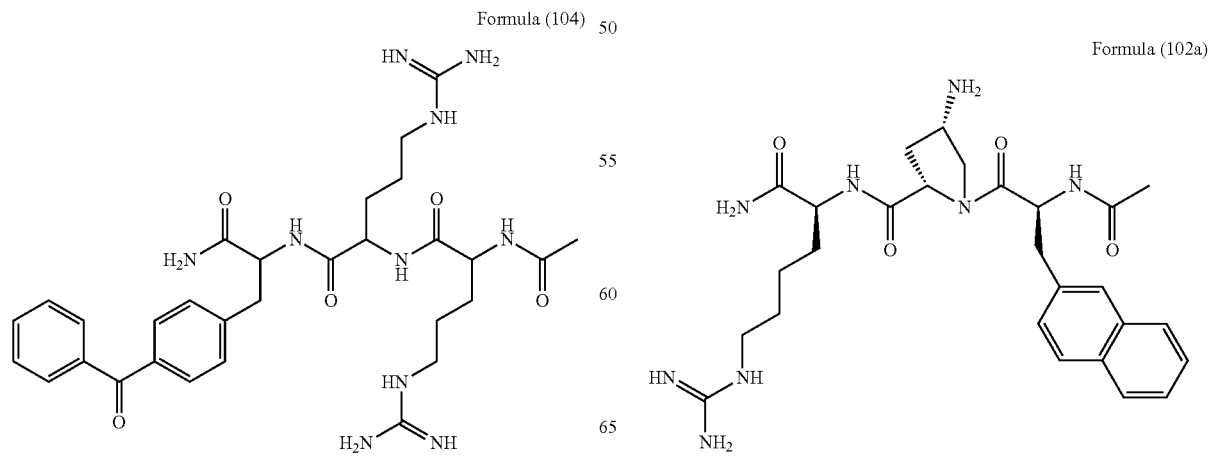
Formula (104)
Formula (102a)

-continued

Formula (103a)

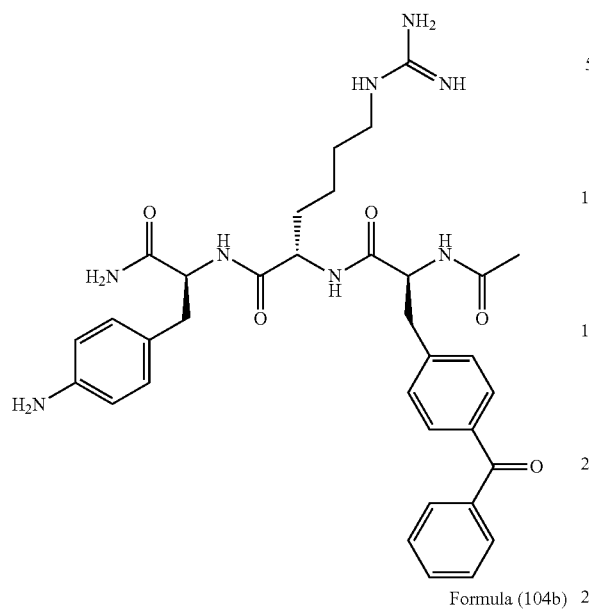

Formula (104b)

Formula (105a)

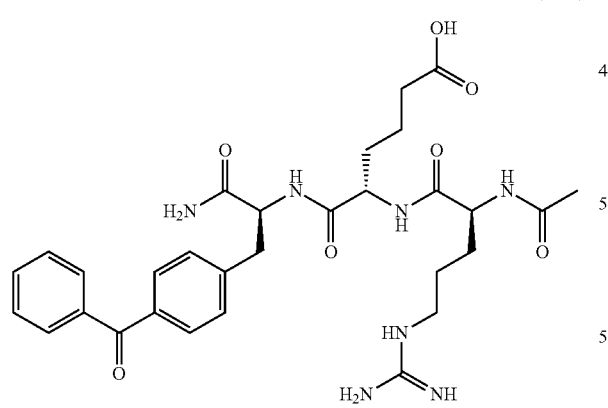

It will be appreciated that compounds of Formula (101a), (102a), (103a), (104b) and (105a) correspond to compounds Tri02-06, respectively, which are discussed in the Examples.

It is believed that the compounds are novel per se.

Accordingly, in accordance with a fourth aspect there is provided a compound of Formula (I), (II), (III), (IV), (V) or (V), wherein:

$R_1$ is —$NR_9R_{10}$ or —OH;

$R_2$ is

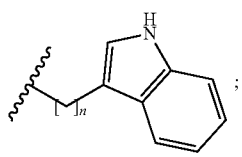

$R_3$ is H or a $C_{1-5}$ straight or branched alkyl or alkenyl;

$R_4$ is

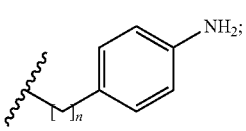

$R_5$ is H or a $C_{1-5}$ straight or branched alkyl or alkenyl;

$R_6$ is

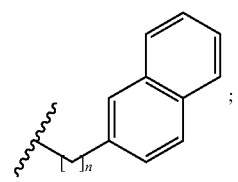

$R_7$ is H or a $C_{1-5}$ straight or branched alkyl or alkenyl;

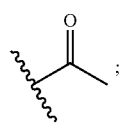

$R_8$ is —H, a $C_{1-5}$ straight or branched alkyl or alkenyl or $R_9$ and $R_{10}$ are independently —H or a $C_{1-5}$ straight or branched alkyl or alkenyl; and each n is independently between 0 and 10;

or a pharmaceutically acceptable salt, solvate, tautomeric form, or polymorphic form thereof.

In accordance with a fifth aspect, there is provided a compound of Formula (I), (II), (III), (IV), (V) or (VI), wherein:

$R_1$ is —$NR_9R_{10}$ or —OH;

$R_2$ is

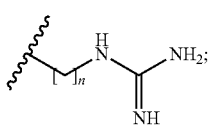

$R_3$ is H or a $C_{1-5}$ straight or branched alkyl or alkenyl;

$R_4$ and $R_5$ together with the nitrogen and carbon to which they are bonded define the following structure:

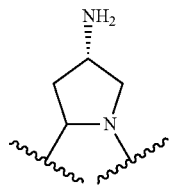

$R_6$ is

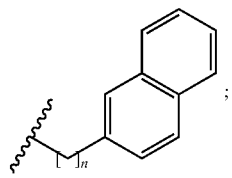

and $R_7$ is H or a $C_{1-5}$ straight or branched alkyl or alkenyl;

$R_8$ is —H, a $C_{1-5}$ straight or branched alkyl or alkenyl or

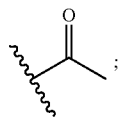 [SMILES: *C(C)=O]

$R_9$ and $R_{10}$ are independently —H or a $C_{1-5}$ straight or branched alkyl or alkenyl; and each n is independently between 0 and 10;

or a pharmaceutically acceptable salt, solvate, tautomeric form, or polymorphic form thereof.

In accordance with a sixth aspect, there is provided a compound of Formula (I), (II), (III), (IV), (V) or (VI), wherein:

$R_1$ is —$NR_9R_{10}$ or —OH;

$R_2$ is

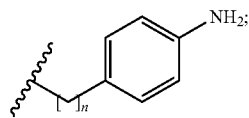

$R_3$ is H or a $C_{1-5}$ straight or branched alkyl or alkenyl;

$R_4$ is

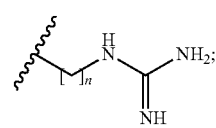

$R_5$ is H or a $C_{1-5}$ straight or branched alkyl or alkenyl;

$R_6$ is

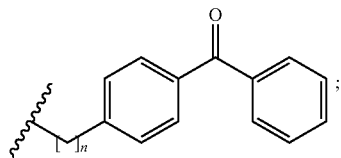

and $R_7$ is H or a $C_{1-5}$ straight or branched alkyl or alkenyl;

$R_8$ is —H, a $C_{1-5}$ straight or branched alkyl or alkenyl or

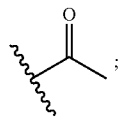

$R_9$ and $R_{10}$ are independently —H or a $C_{1-5}$ straight or branched alkyl or alkenyl; and each n is independently between 0 and 10;

or a pharmaceutically acceptable salt, solvate, tautomeric form, or polymorphic form thereof.

In accordance with a seventh aspect, there is provided a compound of Formula (I), (II), (III), (IV), (V) or (VI), wherein:

$R_1$ is —$NR_9R_{10}$ or —OH;

$R_2$ is

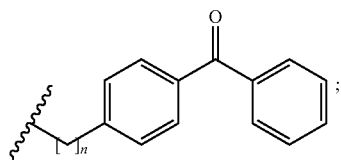

$R_3$ is H or a $C_{1-5}$ straight or branched alkyl or alkenyl;

$R_4$ is

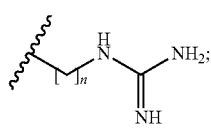

$R_5$ is H or a $C_{1-5}$ straight or branched alkyl or alkenyl;

$R_6$ is

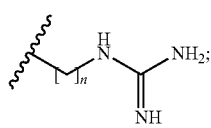

and
R$_7$ is H or a C$_{1-5}$ straight or branched alkyl or alkenyl;
R$_8$ is —H, a C$_{1-5}$ straight or branched alkyl or alkenyl or

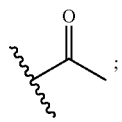 [SMILES: *C(C)=O]

;

R$_9$ and R$_{10}$ are independently —H or a C$_{1-5}$ straight or branched alkyl or alkenyl; and
each n is independently between 0 and 10;
or a pharmaceutically acceptable salt, solvate, tautomeric form, or polymorphic form thereof.

In accordance with an eighth aspect, there is provided a compound of Formula (I), (II), (III), (IV), (V) or (VI), wherein:
R$_1$ is —NR$_9$R$_{10}$ or —OH;
R$_2$ is

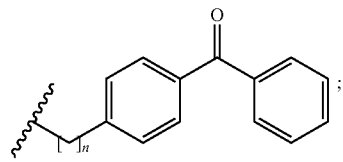

;

R$_3$ is H or a C$_{1-5}$ straight or branched alkyl or alkenyl;
R$_4$ is

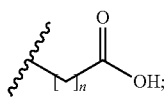

;

R$_5$ is H or a C$_{1-5}$ straight or branched alkyl or alkenyl;
R$_6$ is

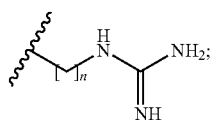

;

and
R$_7$ is H or a C$_{1-5}$ straight or branched alkyl or alkenyl;
R$_8$ is —H, a C$_{1-5}$ straight or branched alkyl or alkenyl or

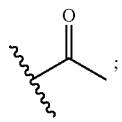 [SMILES: *C(C)=O]

;

R$_9$ and R$_{10}$ are independently —H or a C$_{1-5}$ straight or branched alkyl or alkenyl; and each n is independently between 0 and 10;
or a pharmaceutically acceptable salt, solvate, tautomeric form, or polymorphic form thereof.

It will be appreciated that any of the definitions of the R groups and Formulae of the compounds of the fourth, fifth, sixth, seventh and eighth aspects may be further limited as described above in relation to the first, second and third aspects.

In a further aspect there is provided the compounds according to the fourth, fifth, sixth, seventh and eighth aspects for use in therapy.

In a still further aspect there is provided the compounds according to the fourth, fifth, sixth, seventh and eighth aspects for use in the treating, ameliorating, or preventing a neurodegenerative disorder.

It will be appreciated that compounds according to the invention may be used in a medicament which may be used in a monotherapy (i.e. use of the compound defined by the first aspect), for treating, ameliorating, or preventing neurodegenerative disorder, such as Alzheimer's disease. Alternatively, the compounds according to the invention may be used as an adjunct to, or in combination with, known therapies for treating, ameliorating, or preventing Alzheimer's disease, such as acetylcholinesterase inhibitors.

The compounds according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given, and preferably enables delivery of the peptide across the blood-brain barrier.

It will be appreciated that the efficiency of any treatment for brain disorders depends on the ability of the candidate therapeutic compounds to cross the blood-brain barrier (BBB). However, it is well-known that, during Alzheimer's disease, the blood-brain barrier increases in permeability that could allow the compounds of the invention to reach the central nervous system, indeed ideally only at the sites of degeneration where it is needed, i.e. where the BBB is compromised.

Two main strategies may be applied to cross the BBB with peptides of the invention, including: (1) use of nanoparticles as transporters to specifically target the brain and deliver the active compound. This method has successfully been used to deliver peptides, proteins and anticancer drugs deliver to the brain; and (2) use of cargo peptides. The addition of such a peptide specifically transported across the BBB allows the transfer of the compounds of the invention through a facilitated manner. U.S. Pat. No.

Medicaments comprising compounds according to the invention may be used in a number of ways. For instance, oral administration may be required, in which case the compound may be contained within a composition that may, for example, be ingested orally in the form of a tablet, capsule or liquid. An alternative option for administrating the compounds would be to use a nasal spray, since peptide administration by nasal spray reaches the brain faster and more efficiently than oral or intravenous ways of administration (see memoryzine.com/2010/07/26/nose-sprays-cross-blood-brain-barrier-fa-ster-and-safer/). Hence, compositions comprising compounds of the invention may be administered by inhalation (e.g. intranasally). Compositions may also be formulated for topical use. For instance, creams or ointments may be applied to the skin, for example, adjacent the brain.

Compounds according to the invention may also be incorporated within a slow- or delayed-release device. Such devices may, for example, be inserted on or under the skin, and the medicament may be released over weeks or even months. The device may be located at least adjacent the treatment site, e.g. the head. Such devices may be particularly advantageous when long-term treatment with compounds used according to the invention is required and which would normally require frequent administration (e.g. at least daily injection).

In a preferred embodiment, medicaments according to the invention may be administered to a subject by injection into the blood stream or directly into a site requiring treatment. For example, the medicament may be injected at least adjacent the brain. Injections may be intravenous (bolus or infusion) or subcutaneous (bolus or infusion), or intradermal (bolus or infusion).

It will be appreciated that the amount of the compound that is required is determined by its biological activity and bioavailability, which in turn depends on the mode of administration, the physiochemical properties of the polypeptide and whether it is being used as a monotherapy or in a combined therapy. The frequency of administration will also be influenced by the half-life of the compound within the subject being treated. Optimal dosages to be administered may be determined by those skilled in the art, and will vary with the particular compound in use, the strength of the pharmaceutical composition, the mode of administration, and the advancement of the neurodegenerative disease. Additional factors depending on the particular subject being treated will result in a need to adjust dosages, including subject age, weight, gender, diet, and time of administration.

Generally, a daily dose of between 0.001 μg/kg of body weight and 10 mg/kg of body weight of the compound according to the invention may be used for treating, ameliorating, or preventing neurodegenerative disease, depending upon which polypeptide is used. More preferably, the daily dose is between 0.01 μg/kg of body weight and 1 mg/kg of body weight, and most preferably between approximately 0.1 μg/kg and 10 μg/kg body weight.

The compound may be administered before, during or after onset of neurodegenerative disease. Daily doses may be given as a single administration (e.g. a single daily injection or inhalation of a nasal spray). Alternatively, the compound may require administration twice or more times during a day. As an example, compounds may be administered as two (or more depending upon the severity of the neurodegenerative disease being treated) daily doses of between 0.07 μg and 700 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of compound according to the invention to a patient without the need to administer repeated doses.

Known procedures, such as those conventionally employed by the pharmaceutical industry (e.g. in vivo experimentation, clinical trials, etc.), may be used to form specific formulations of the compound according to the invention and precise therapeutic regimes (such as daily doses of the agents and the frequency of administration). The inventors believe that they are the first to suggest an anti-neurodegenerative disease composition, based on the use of compounds of the invention.

Hence, in a ninth aspect of the invention, there is provided a pharmaceutical composition comprising a compound according to the first aspect, or a pharmaceutically acceptable salt, solvate, tautomeric form or polymorphic form thereof, and a pharmaceutically acceptable vehicle.

The pharmaceutical composition is preferably an anti-neurodegenerative disease composition, i.e. a pharmaceutical formulation used in the therapeutic amelioration, prevention or treatment of a neurodegenerative disorder in a subject, such as Alzheimer's disease.

The invention also provides, in a tenth aspect, a process for making the pharmaceutical composition according to the ninth aspect, the process comprising contacting a therapeutically effective amount of a compound of the first aspect, or a pharmaceutically acceptable salt, solvate, tautomeric form or polymorphic form thereof, and a pharmaceutically acceptable vehicle.

Preferably, the compound is a compound of Formula (101), (102), (103), (104) or (105). More preferably, the compound is a compound of Formula (101a), (102a), (103a), (104b) or (105a).

A "subject" may be a vertebrate, mammal, or domestic animal. Hence, medicaments according to the invention may be used to treat any mammal, for example livestock (e.g. a horse), pets, or may be used in other veterinary applications. Most preferably, however, the subject is a human being.

A "therapeutically effective amount" of compound is any amount which, when administered to a subject, is the amount of active agent that is needed to treat the neurodegenerative disorder condition, or produce the desired effect.

For example, the therapeutically effective amount of compound used may be from about 0.001 mg to about 800 mg, and preferably from about 0.01 mg to about 500 mg. It is preferred that the amount of compound is an amount from about 0.1 mg to about 100 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, coatings, or tablet-disintegrating agents. The vehicle may also be an encapsulating material. In powders, the vehicle is a finely divided solid that is in admixture with the finely divided active agents according to the invention. In tablets, the active agent may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The active agent according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The compound may be prepared as a sterile solid composition that may be dissolved or suspended at the time of administration using sterile water, saline, or other appropriate sterile injectable medium.

The compound and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The compound used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

All features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

FIGS. 1a and 1b show different views of a representation of the four key areas (Areas 1, 2, 3 and 4) in the allosteric binding pocket (i.e. the active site) of the α7 nicotinic-receptor which bind to the cyclic peptide NBP-14, and the respective distances between these four areas depending on whether NBP-14 competes with T30 (in FIG. 1a) or amyloid (in FIG. 1b);

Figure 1B:
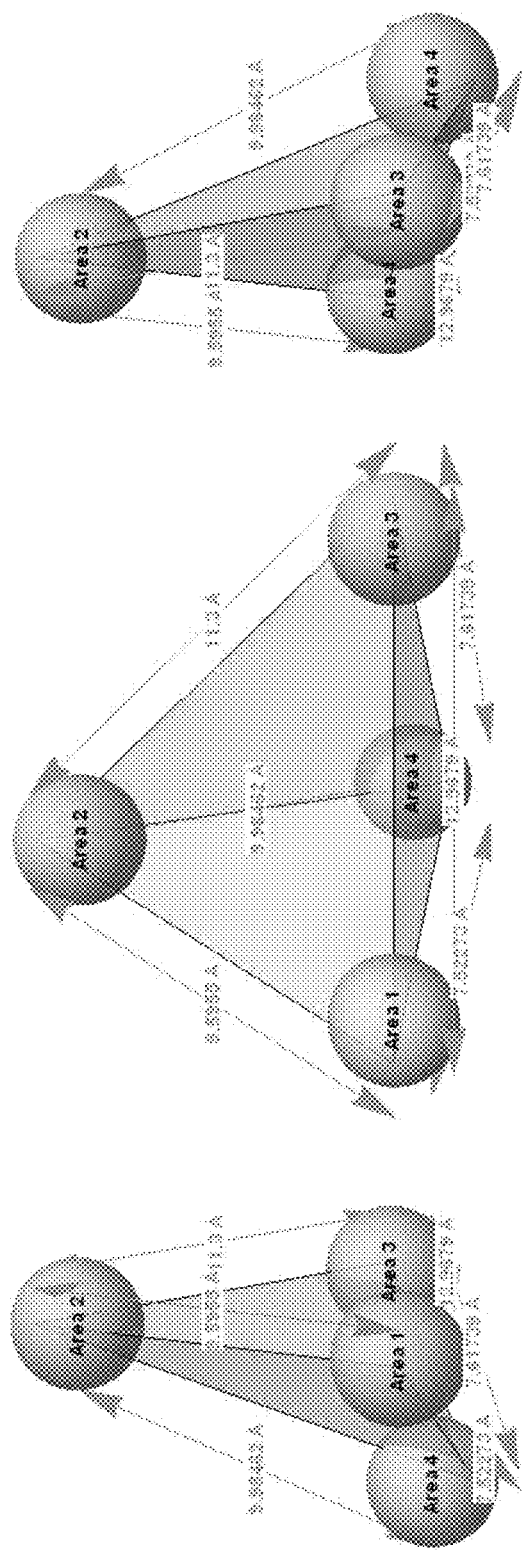
Figure 2:
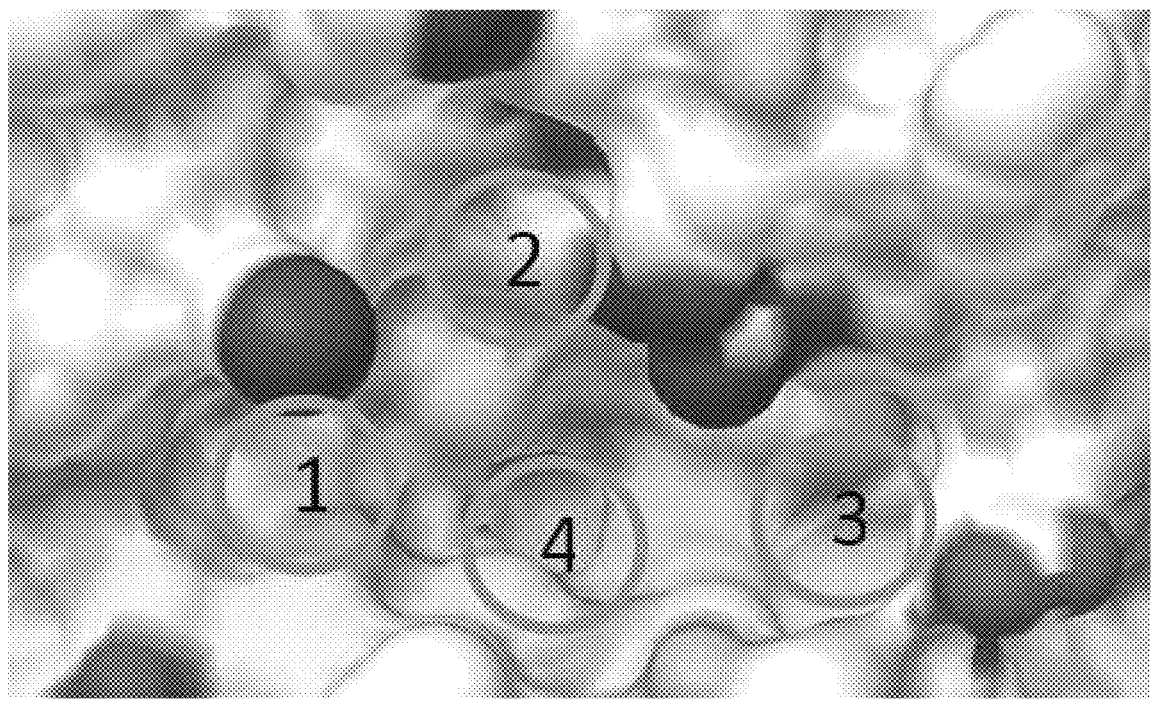
FIG. 2 shows the 3D structure of the α7 nicotinic-receptor binding pocket with a colour coding based on the polarity.
Figure 3:
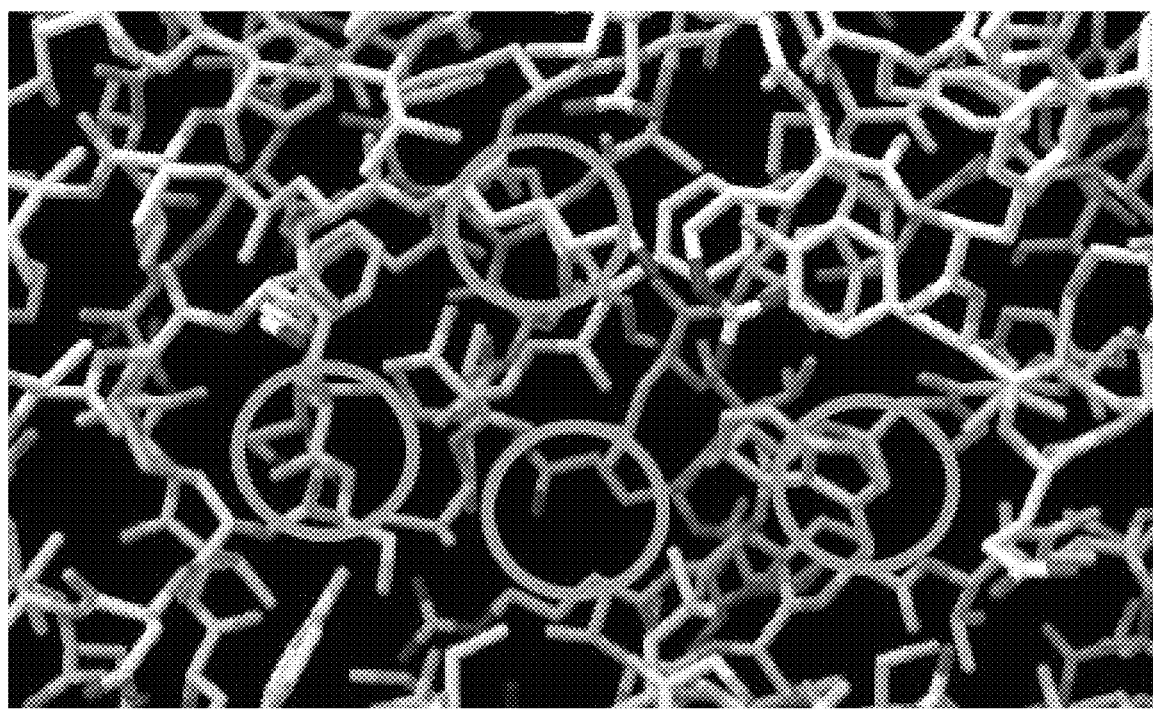
FIG. 3 shows a stick representation of the α7 nicotinic-receptor binding pocket showing Areas 1-4.
Figure 4:
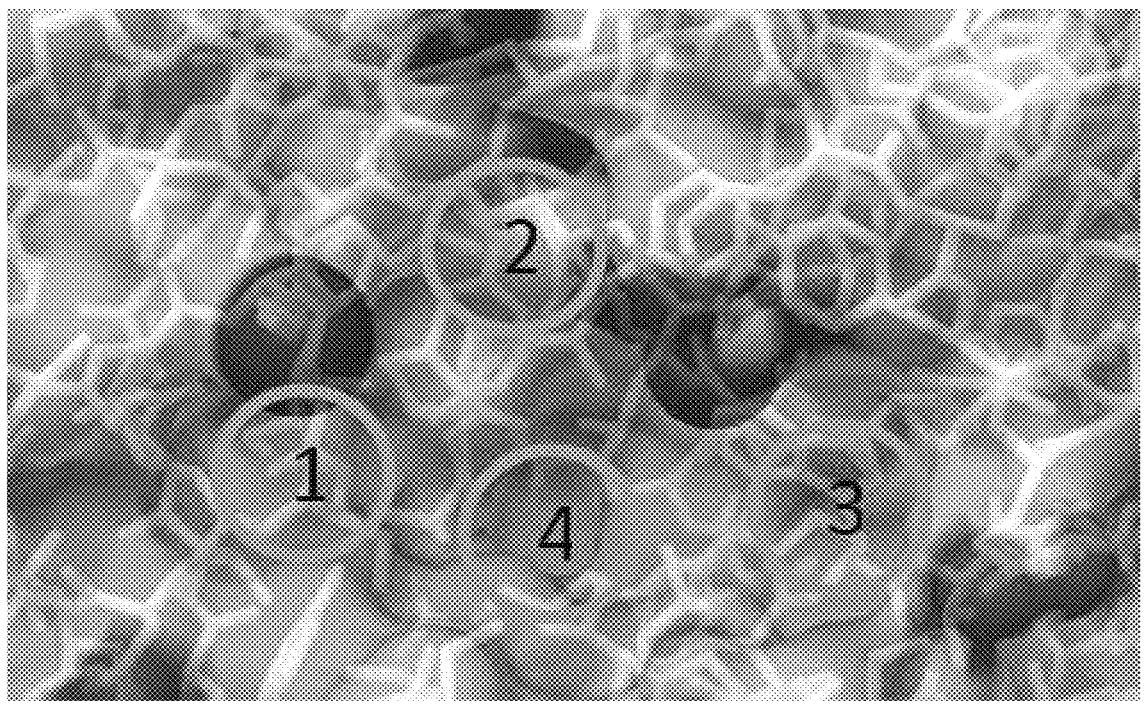
Figure 5:
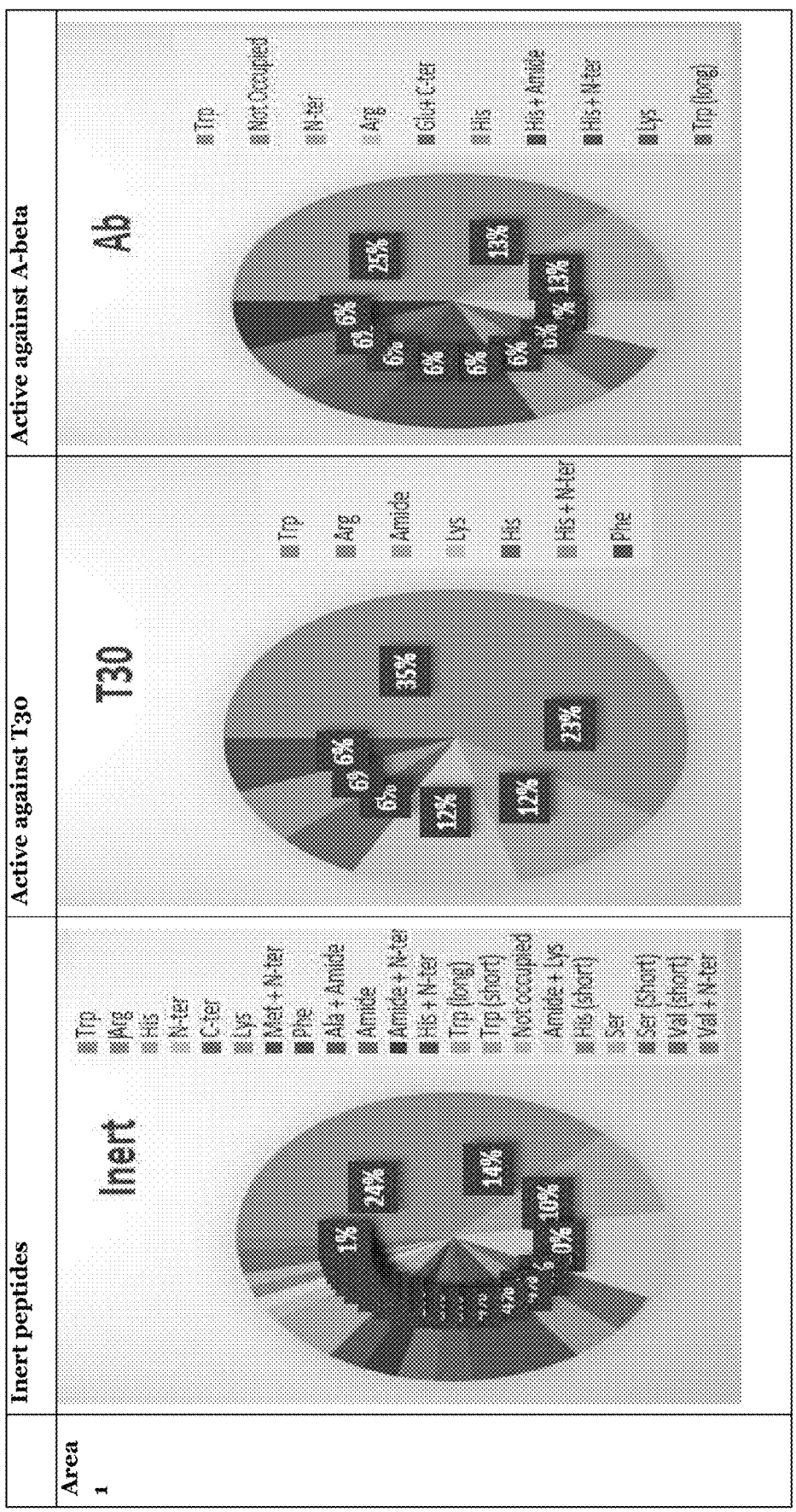
Figure 5:
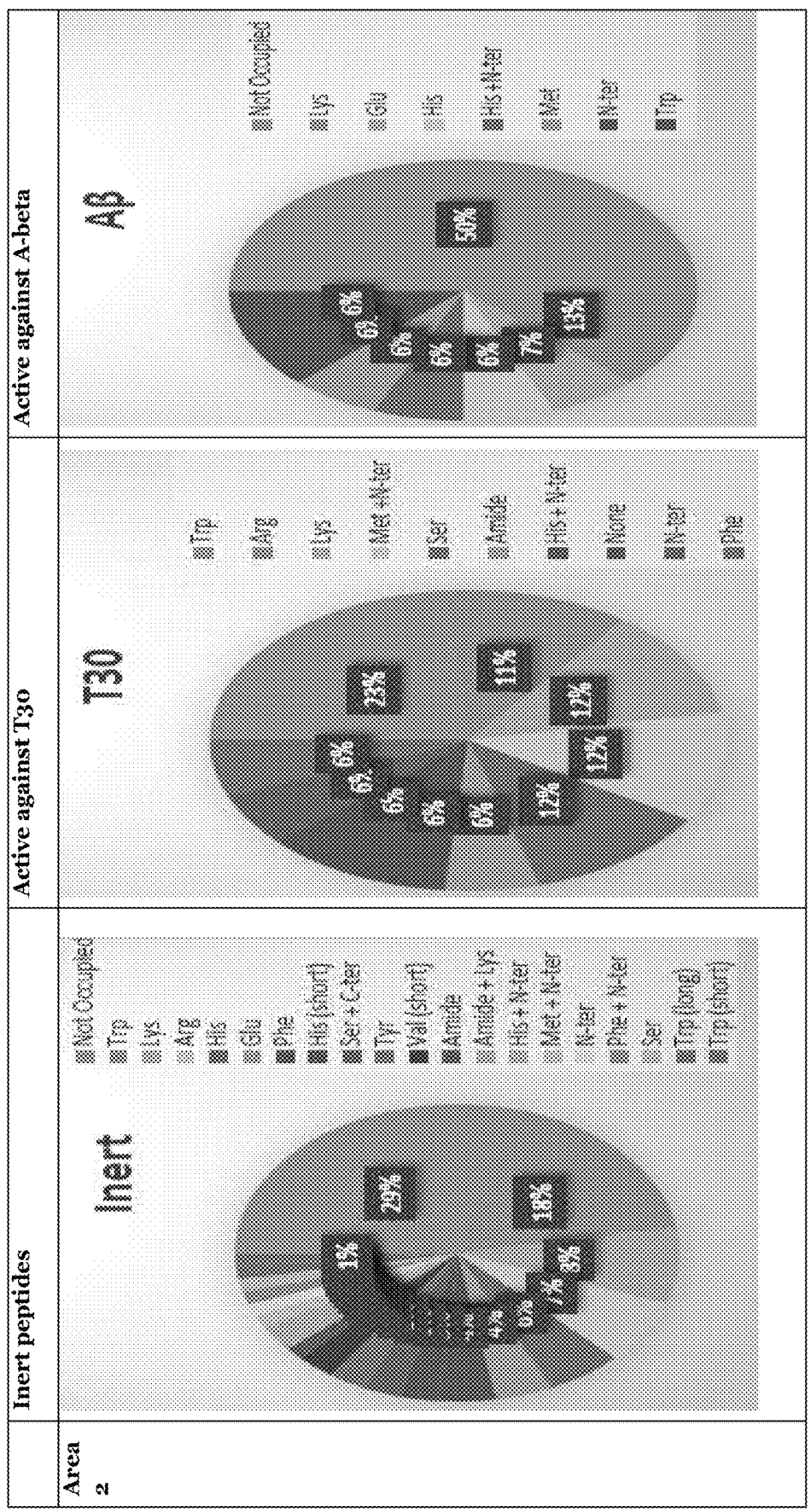
Figure 5:
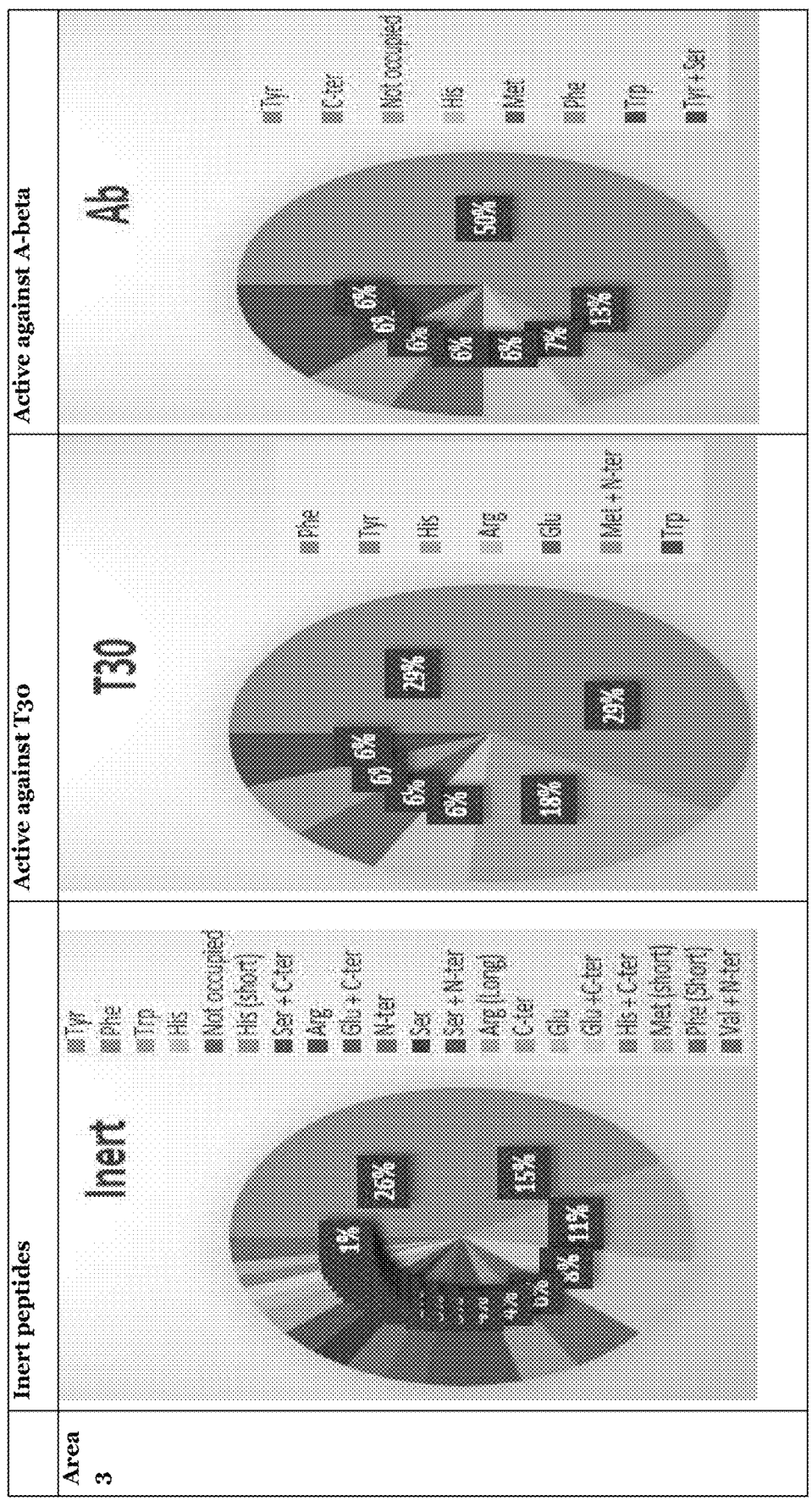
Figure 5:
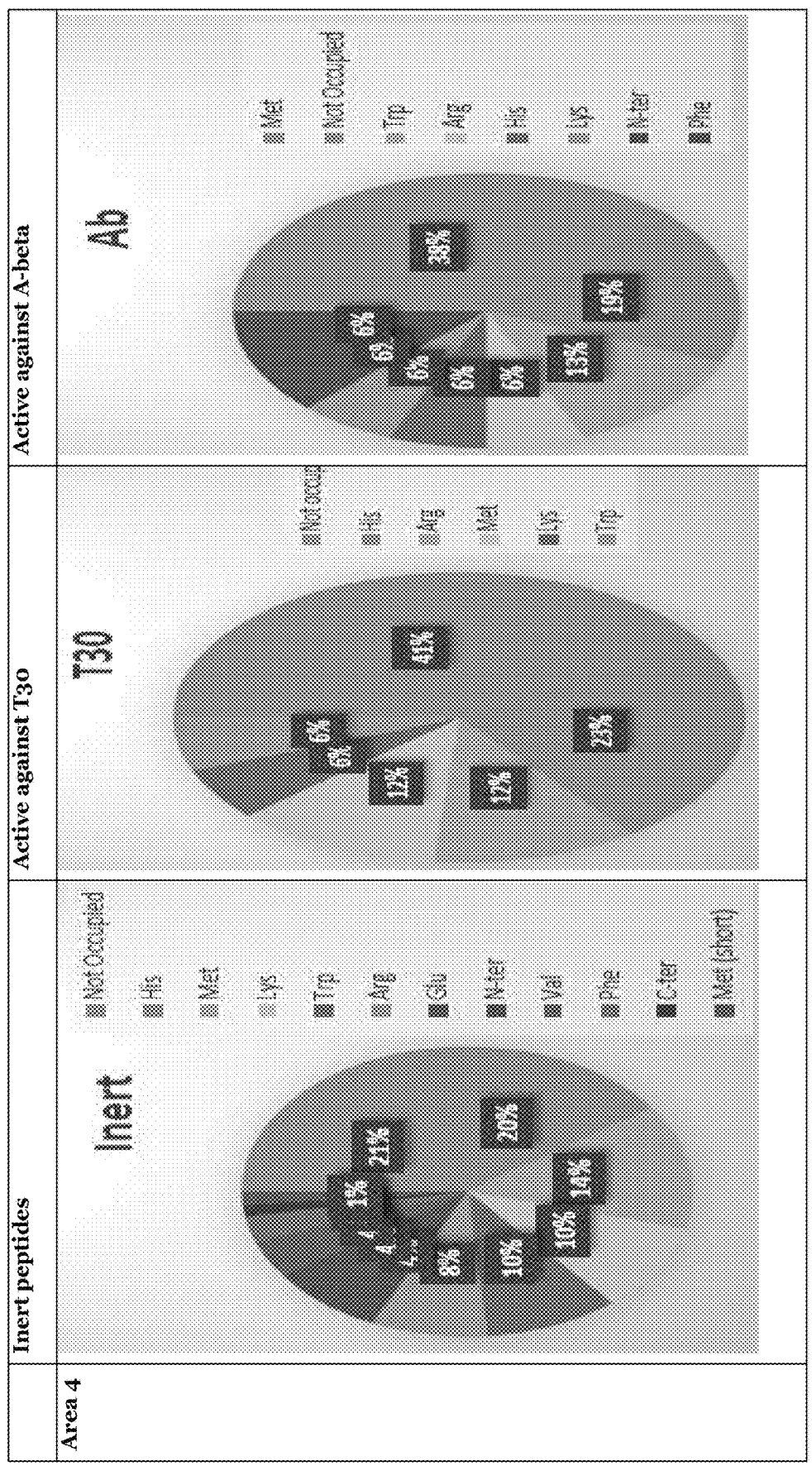
Figure 6A:
Figure 6B:
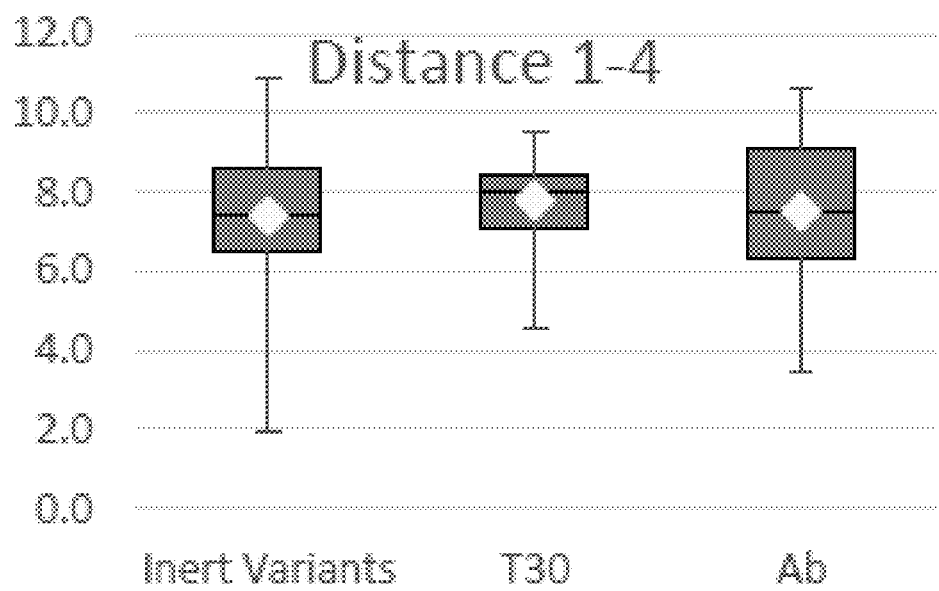
Figure 6C:
Figure 6D:
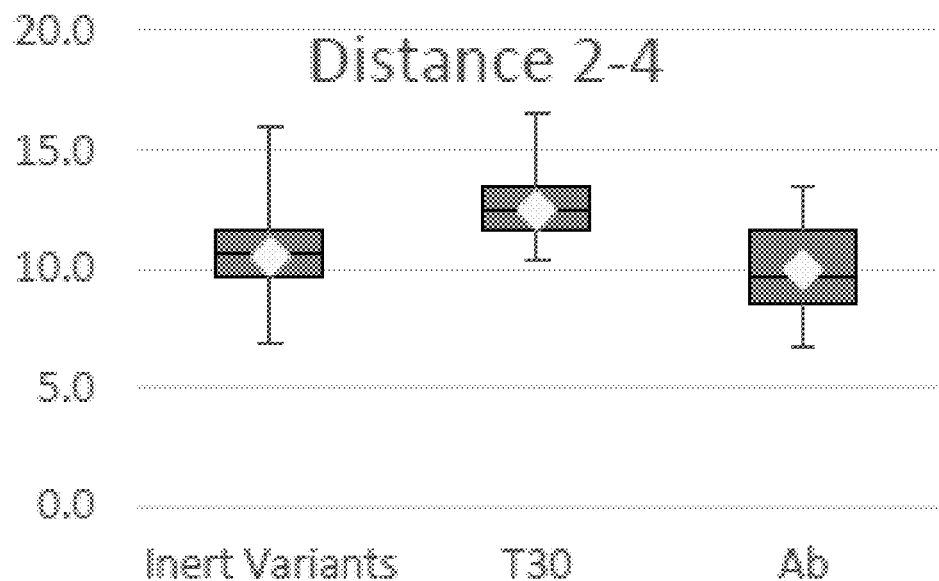
Figure 6E:
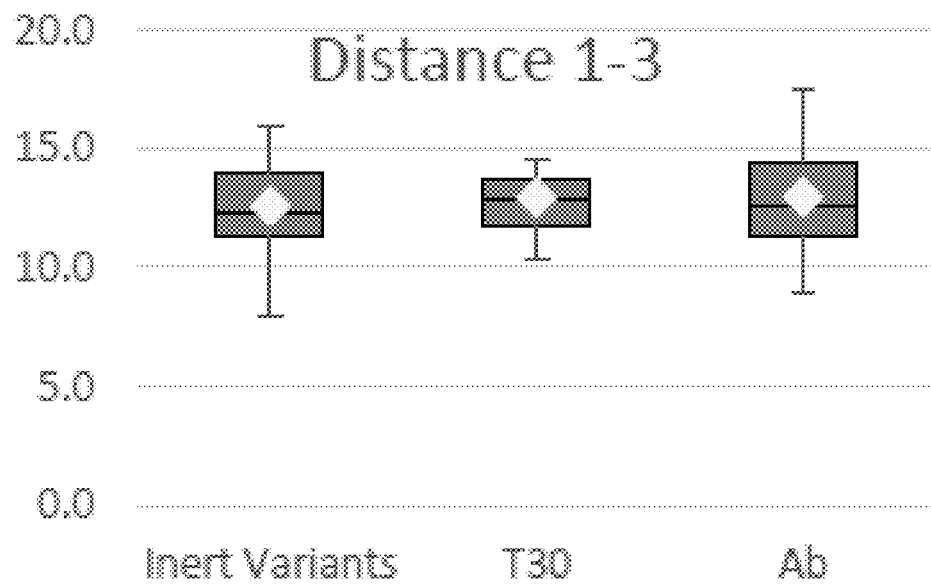
Figure 6F:
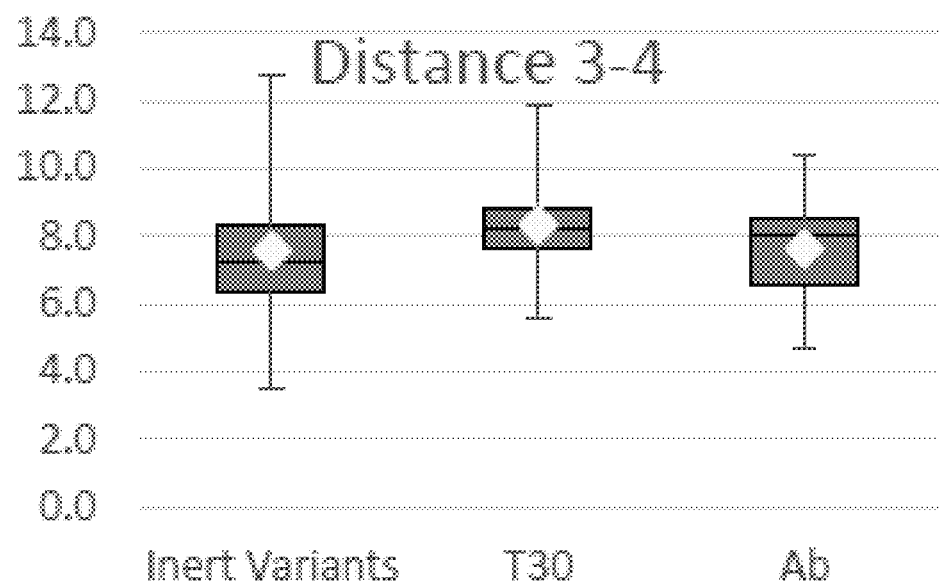
Figure 9:
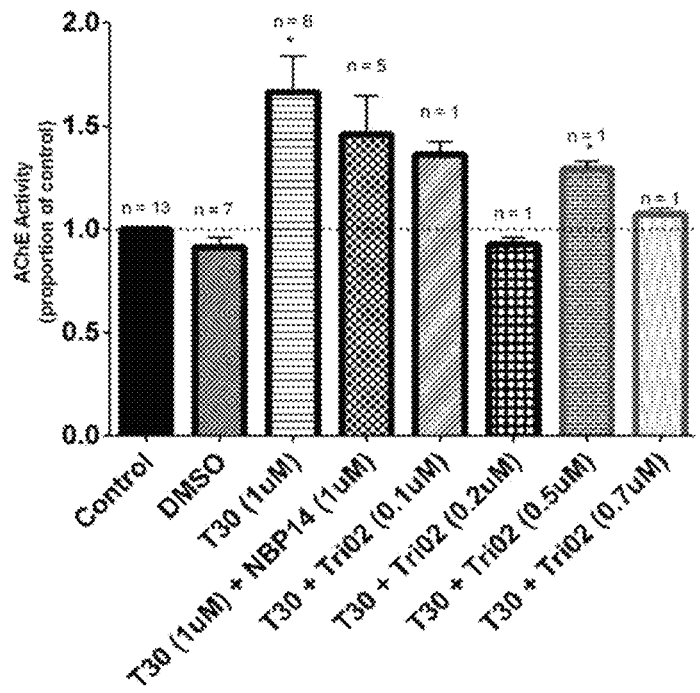
Figure 10:
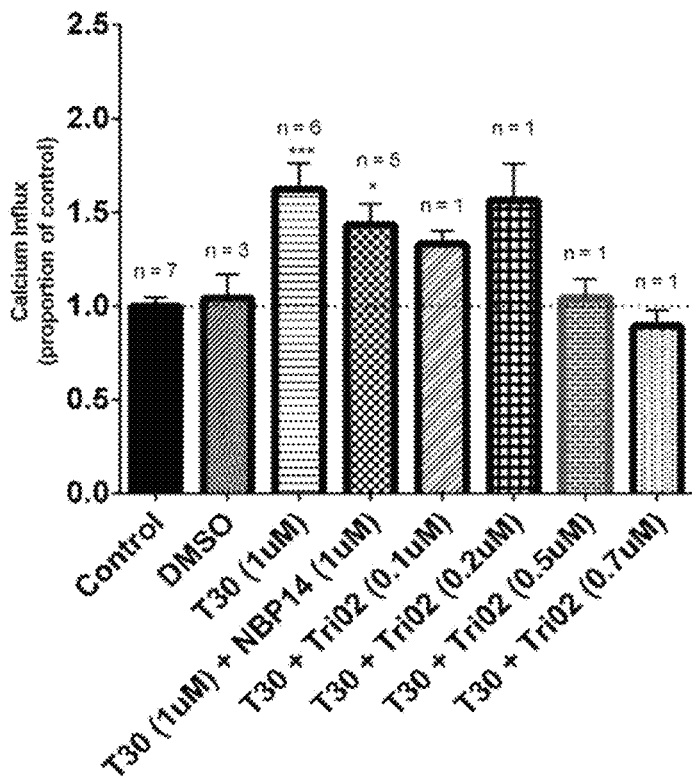
Figure 11:
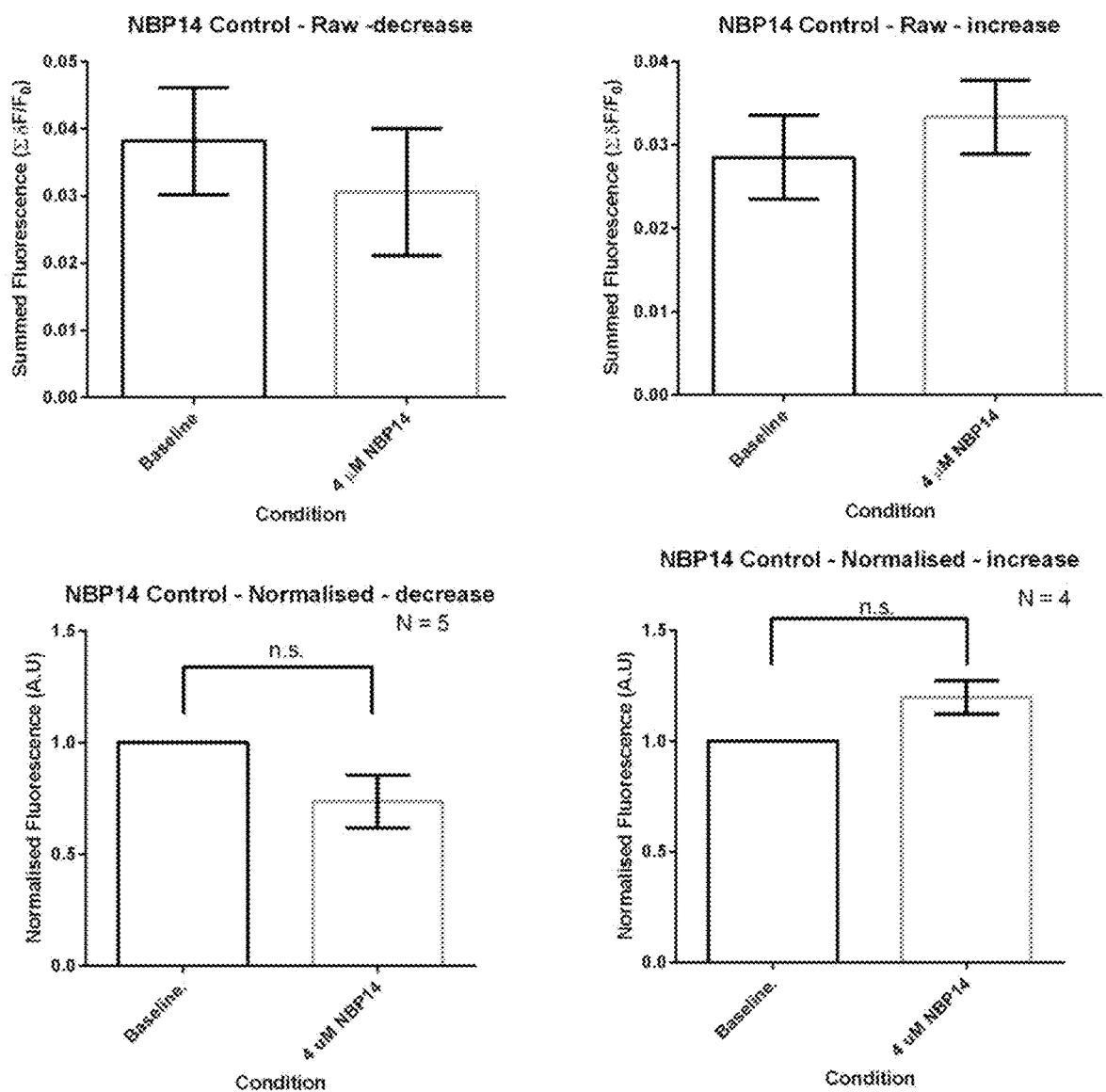
Figure 12:
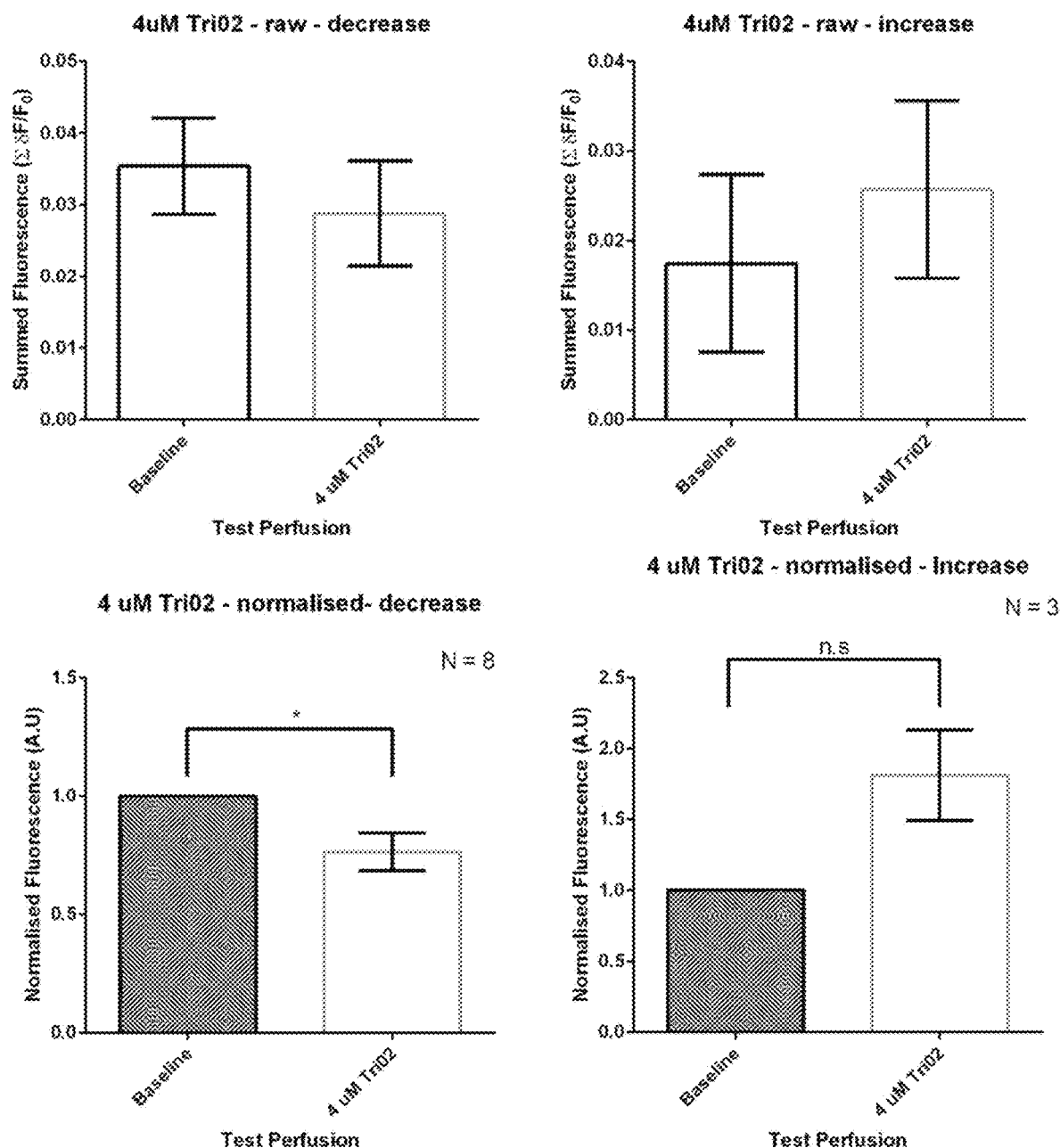
Figure 13:
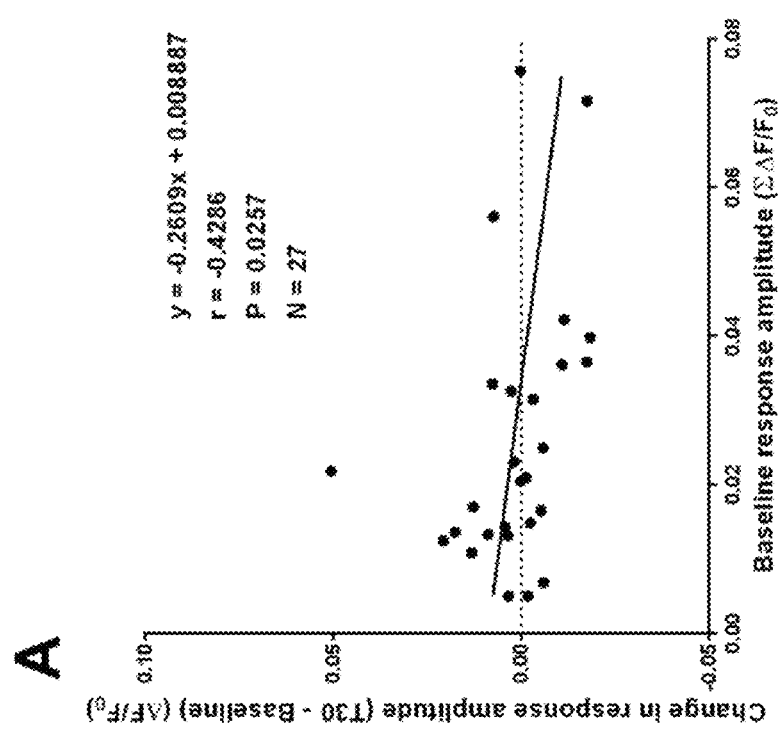
Figure 13:
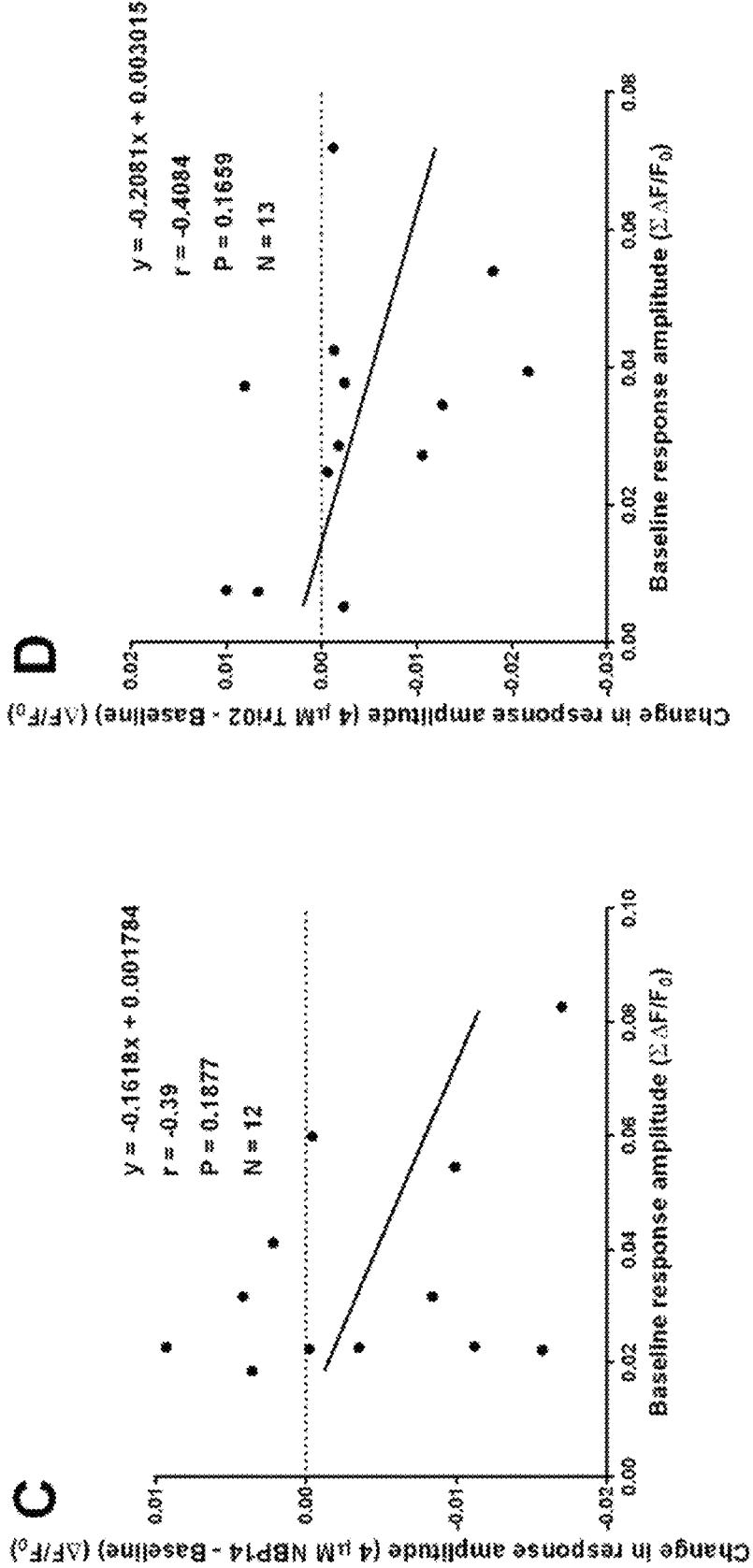
Figure 14:
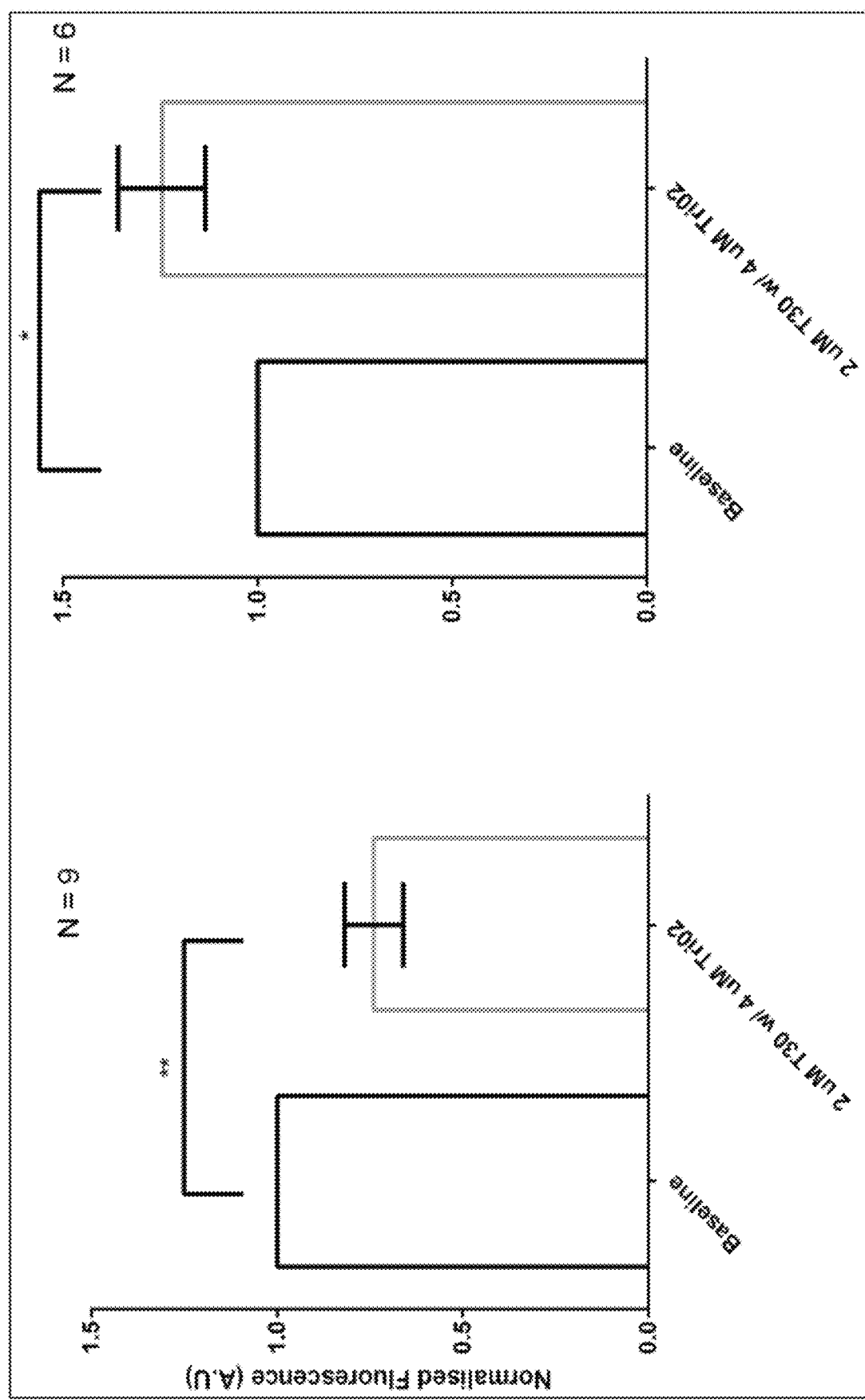
Figure 15:
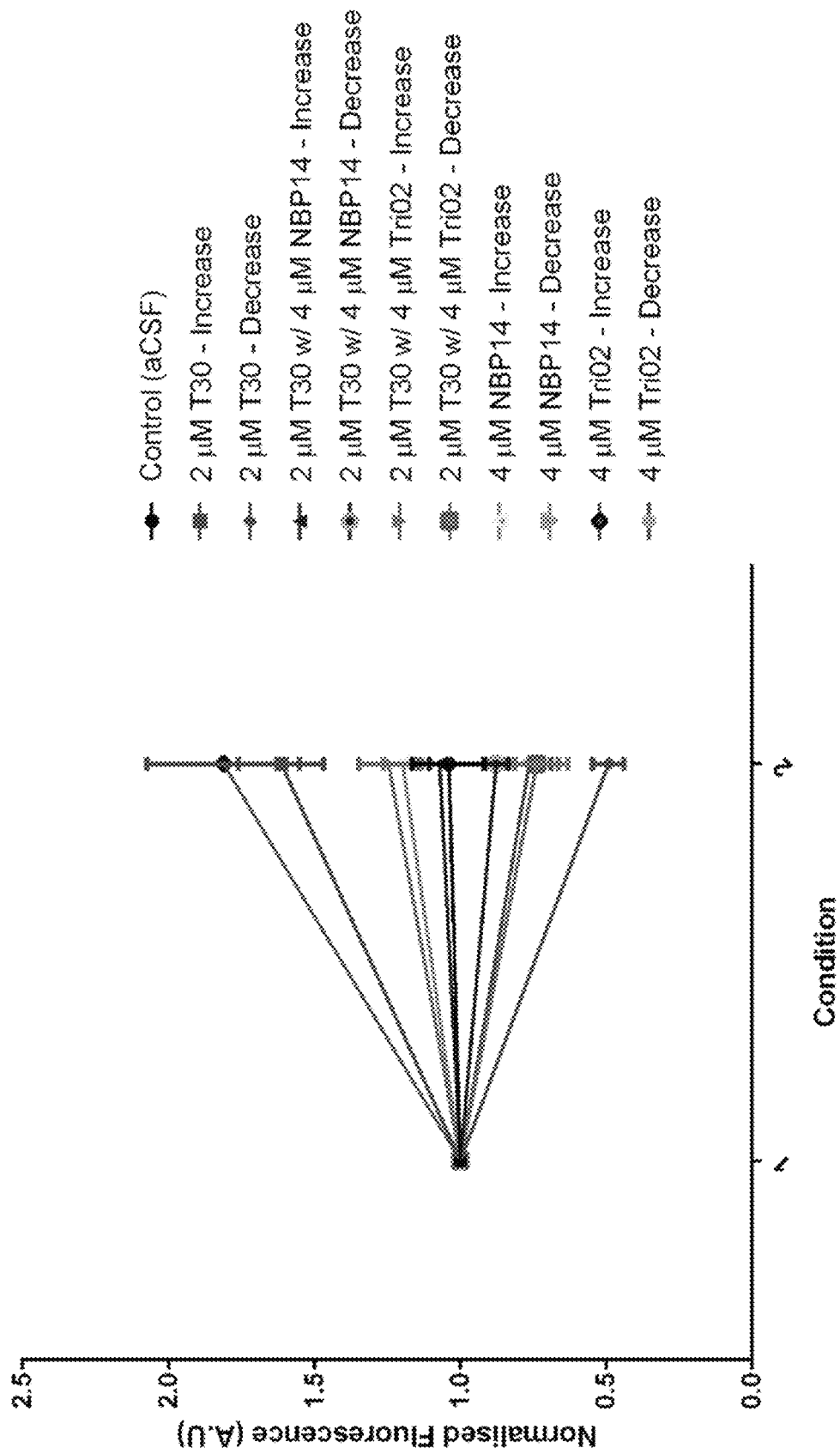
Figure 16:
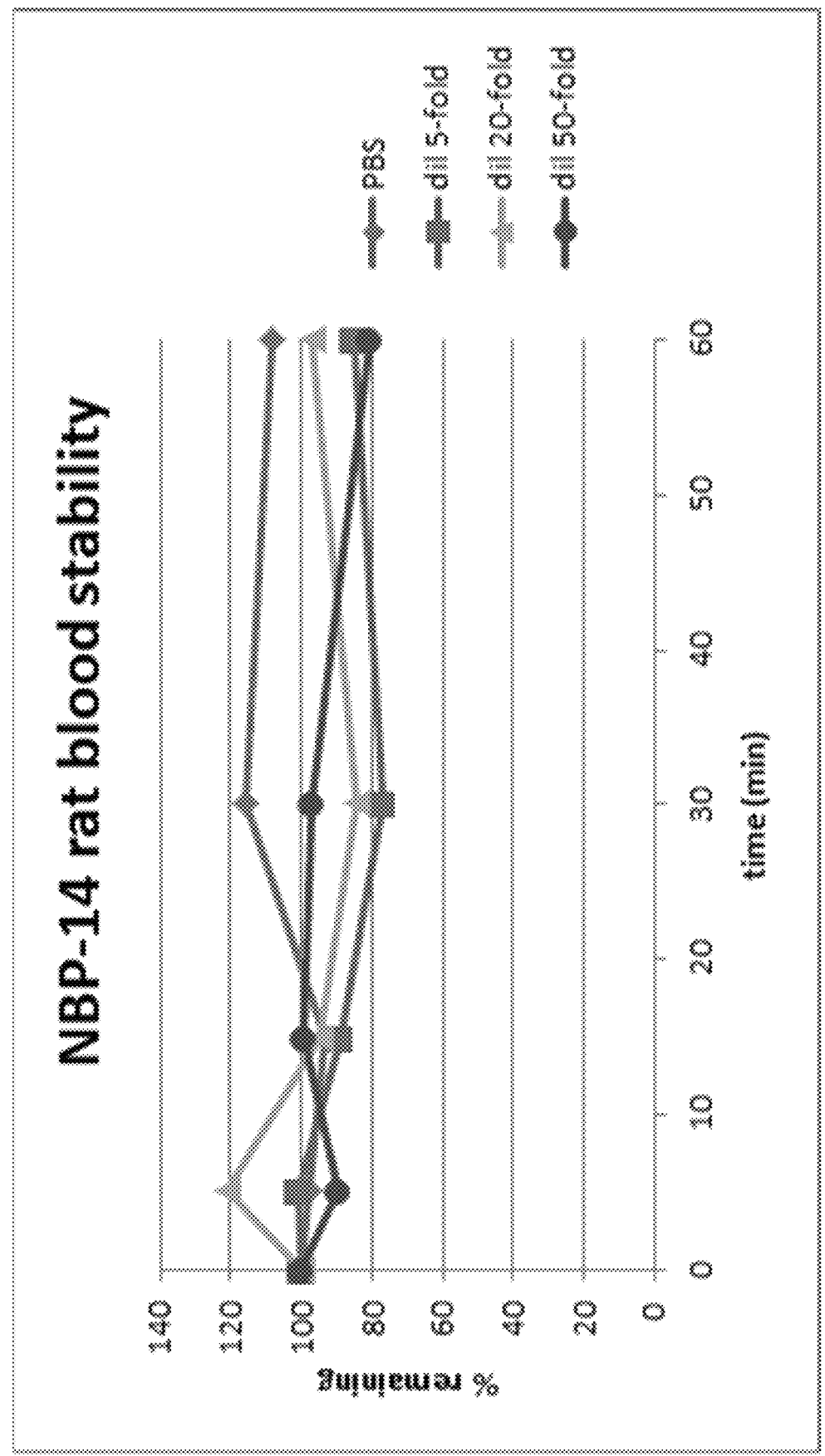
Figure 17:
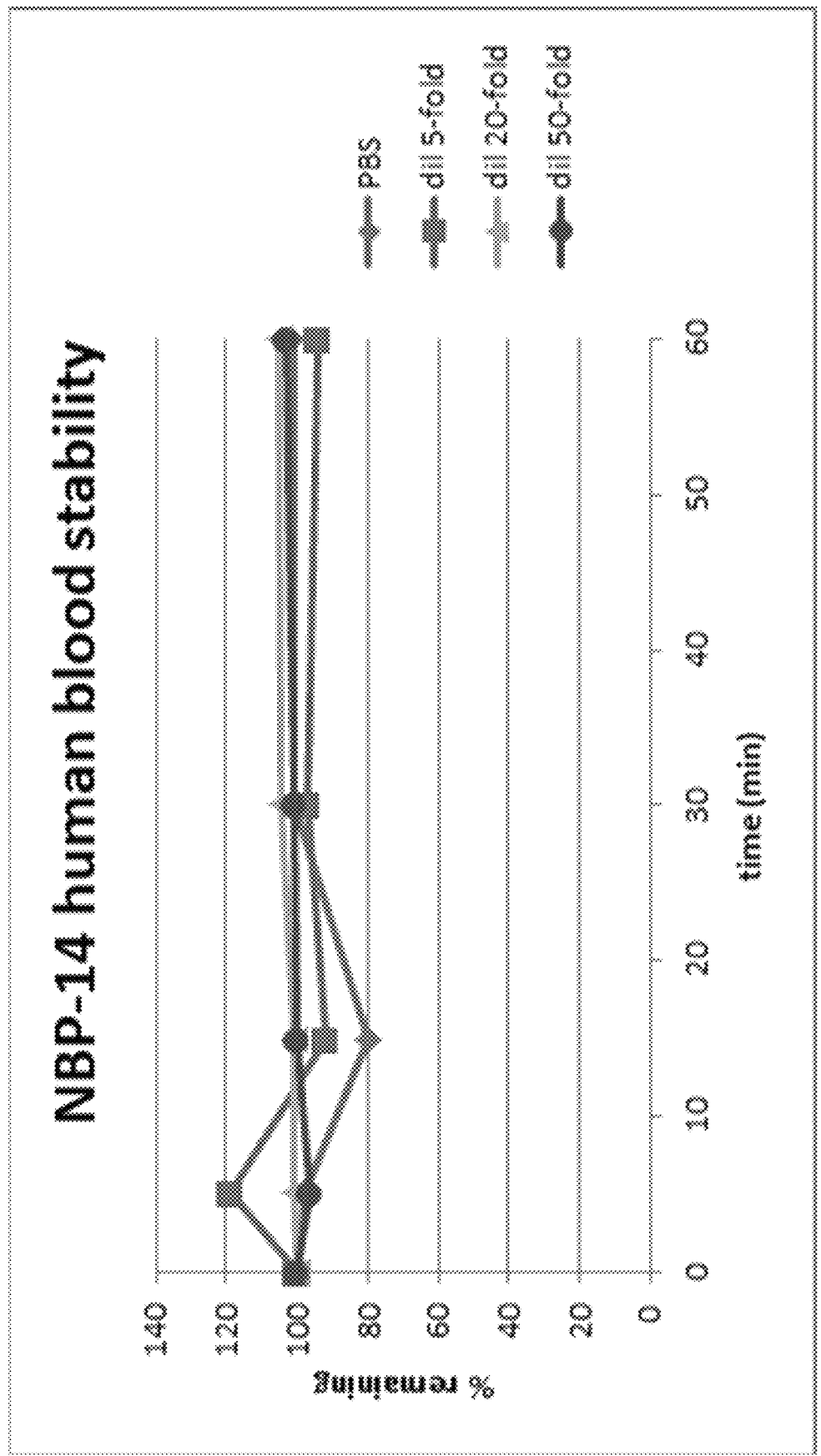
Figure 18:
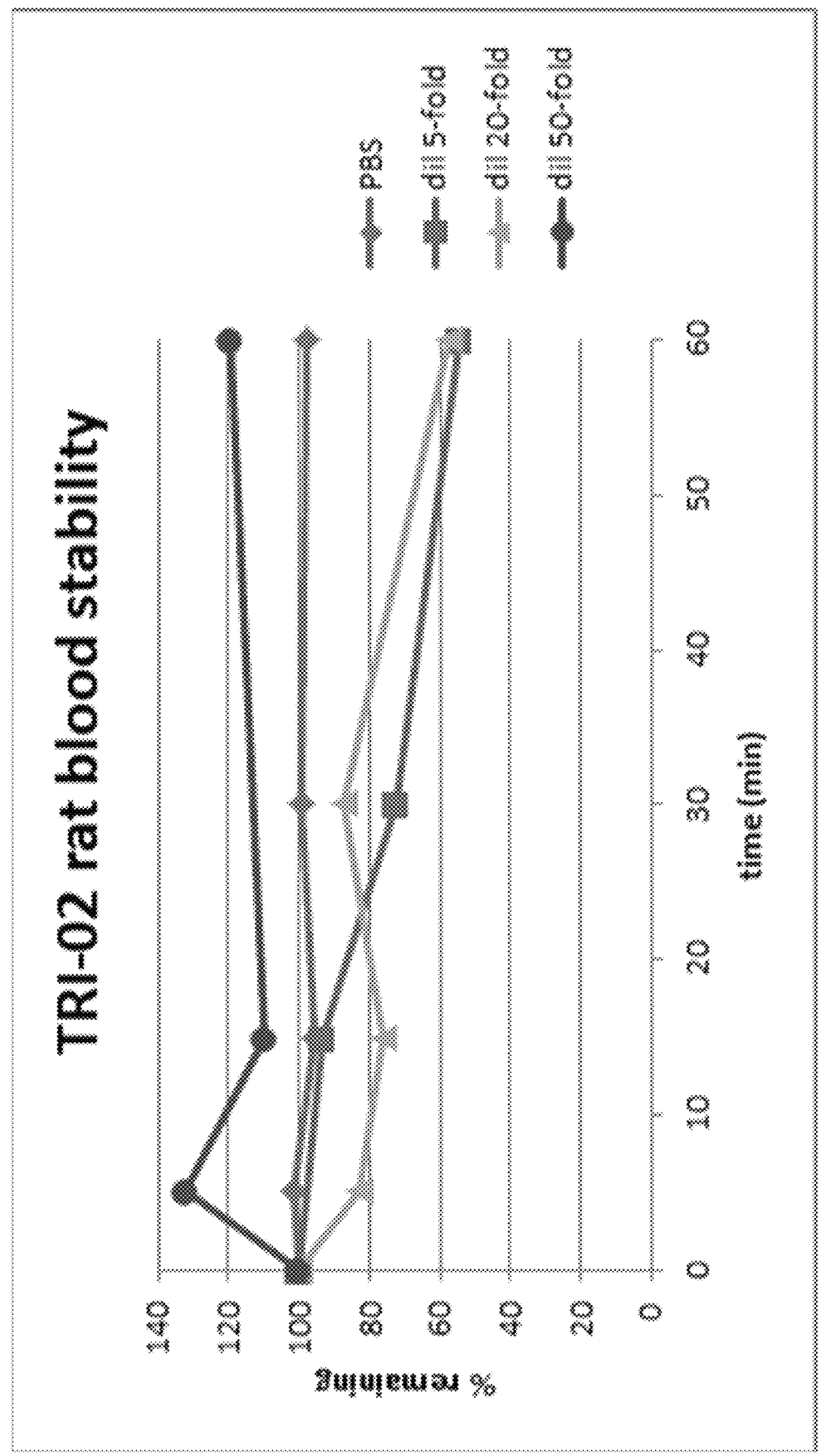
Figure 19:
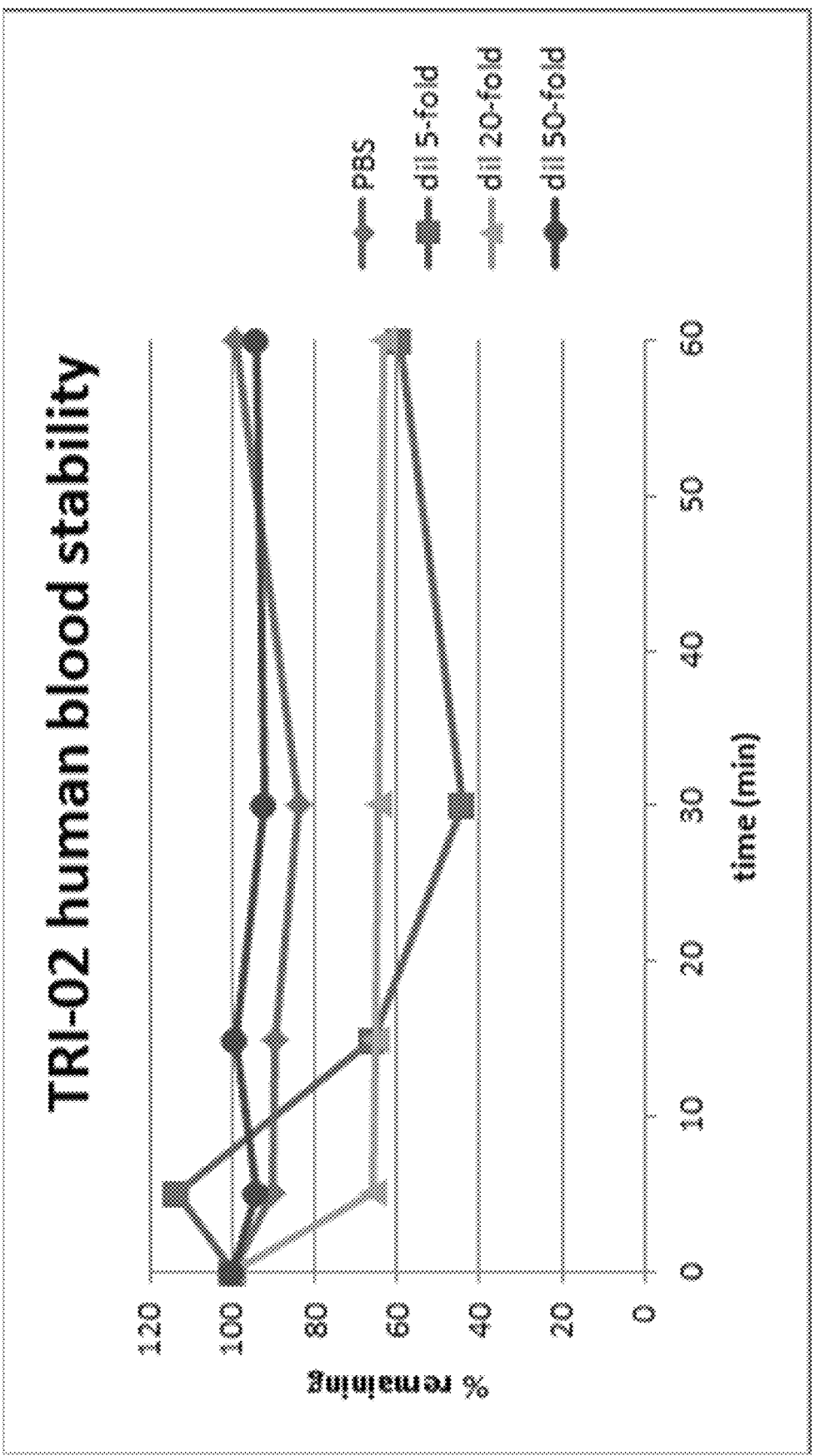
Figure 20:
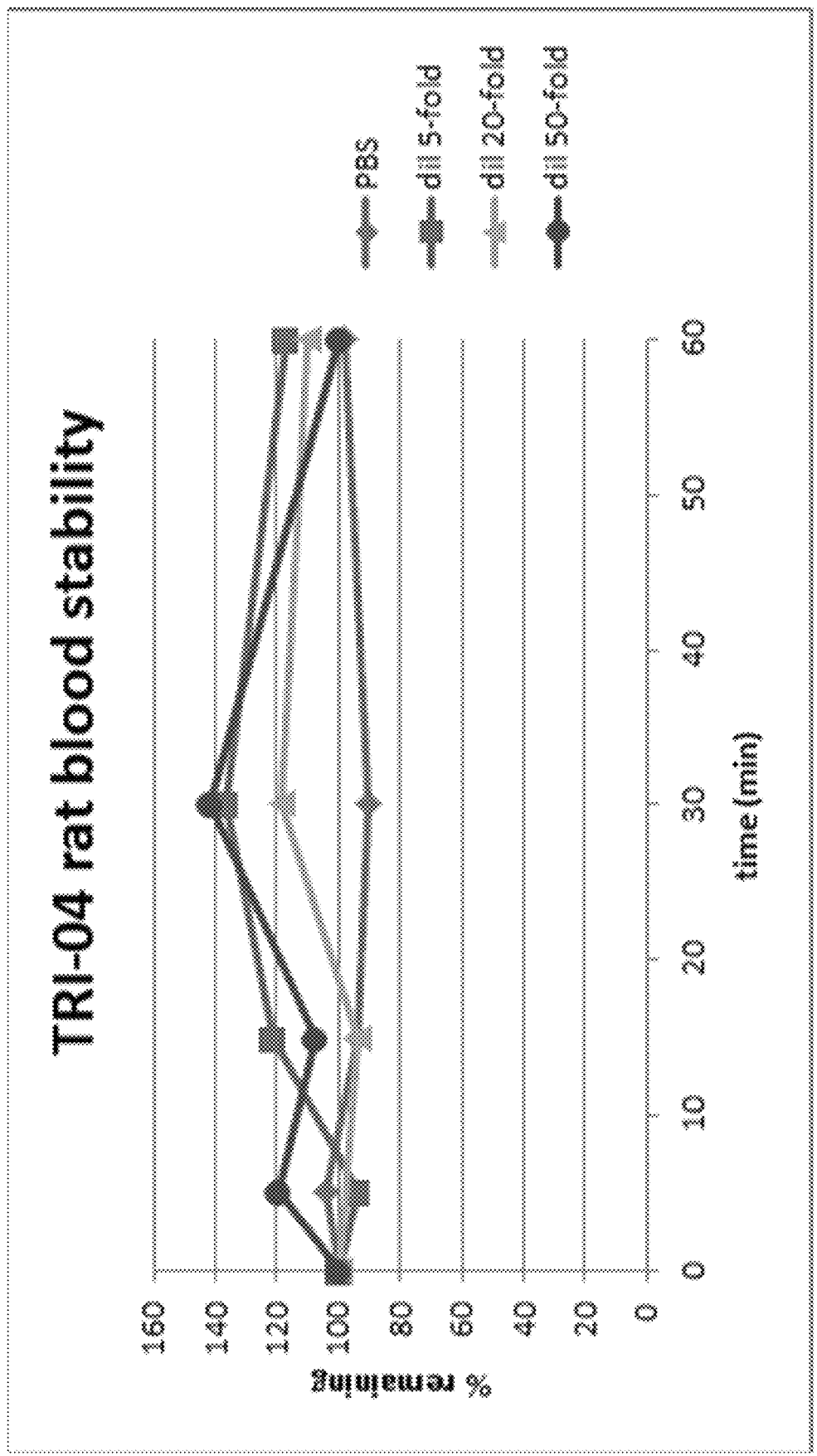
Figure 21:
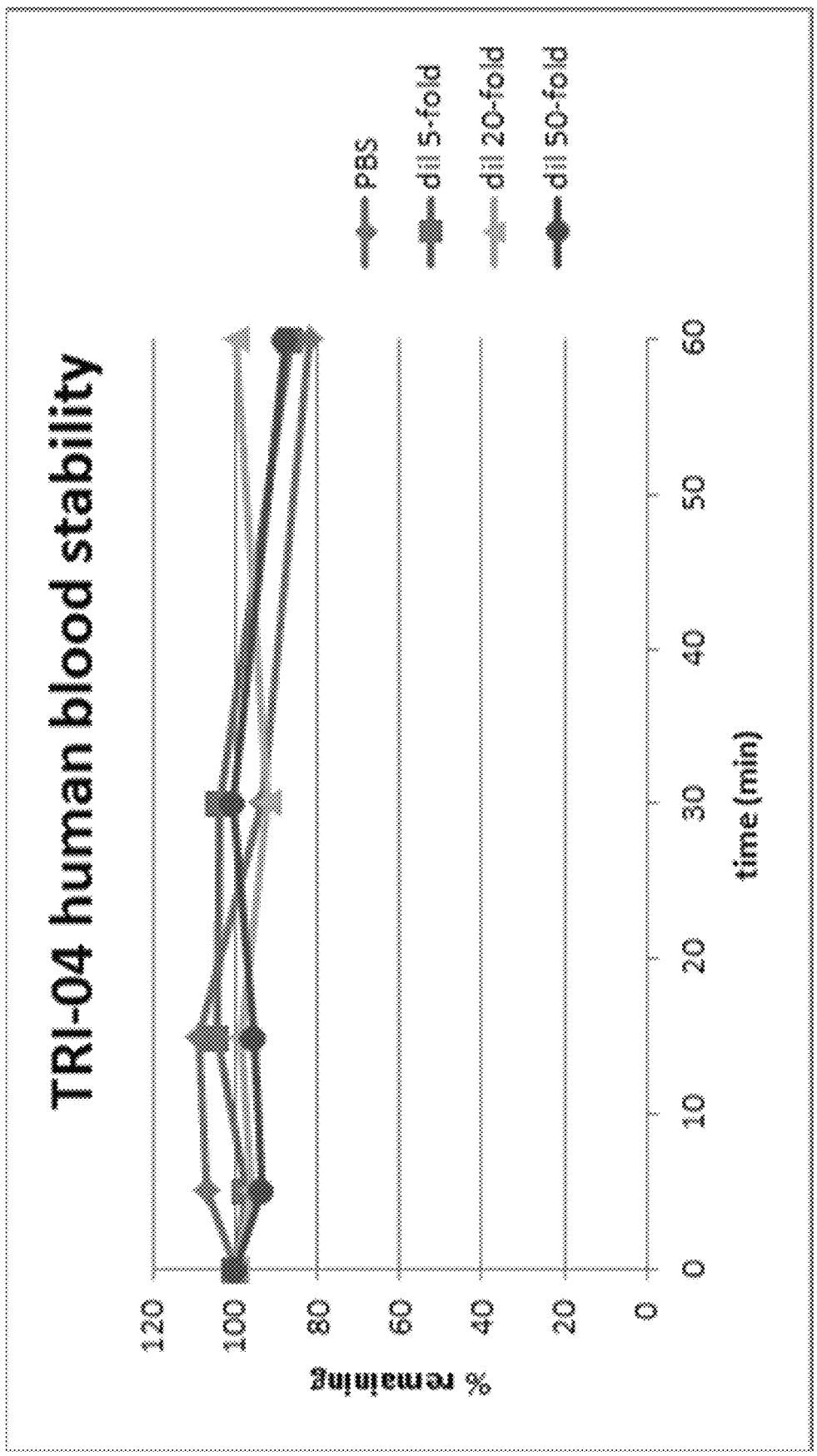
Figure 22:
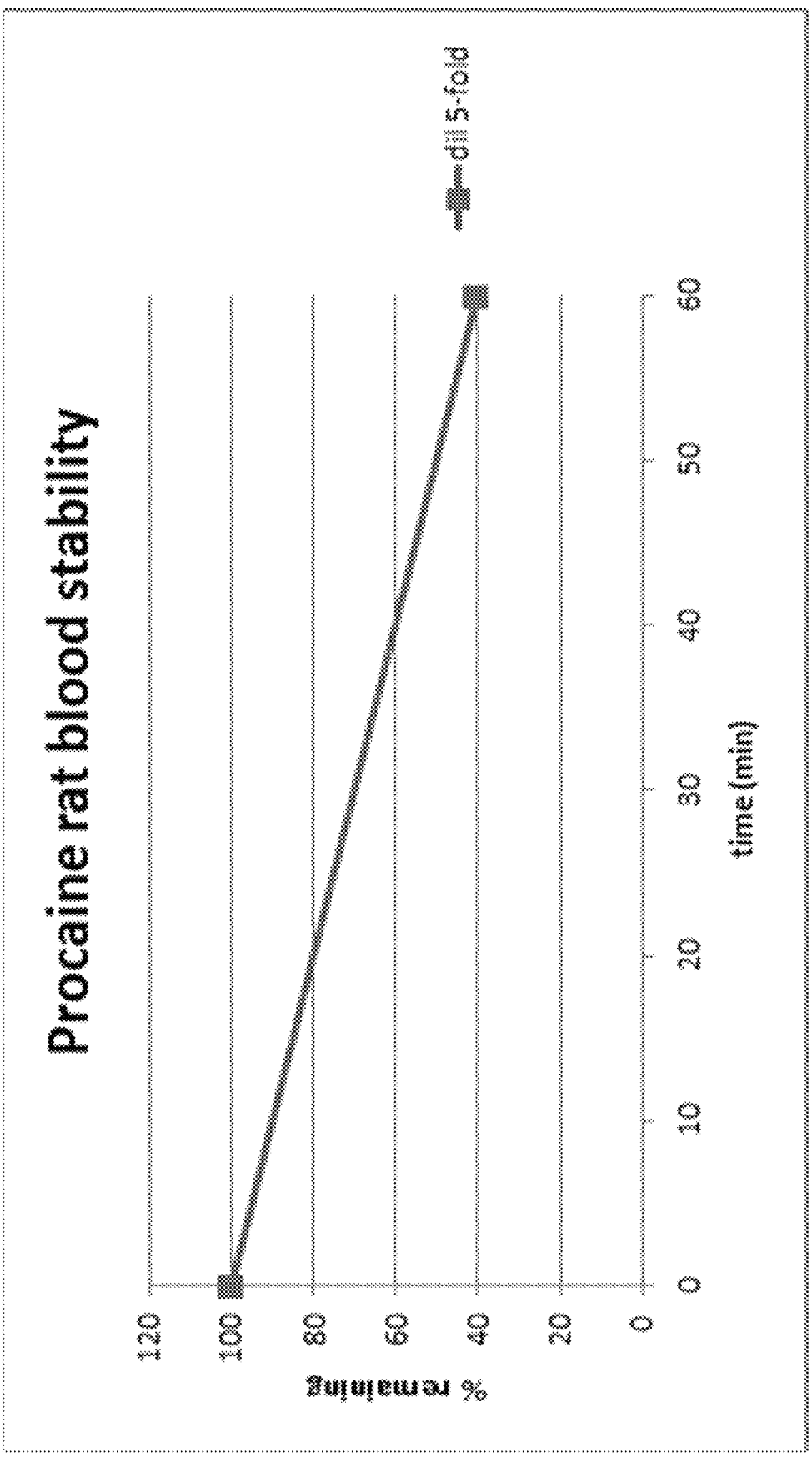
Figure 23:
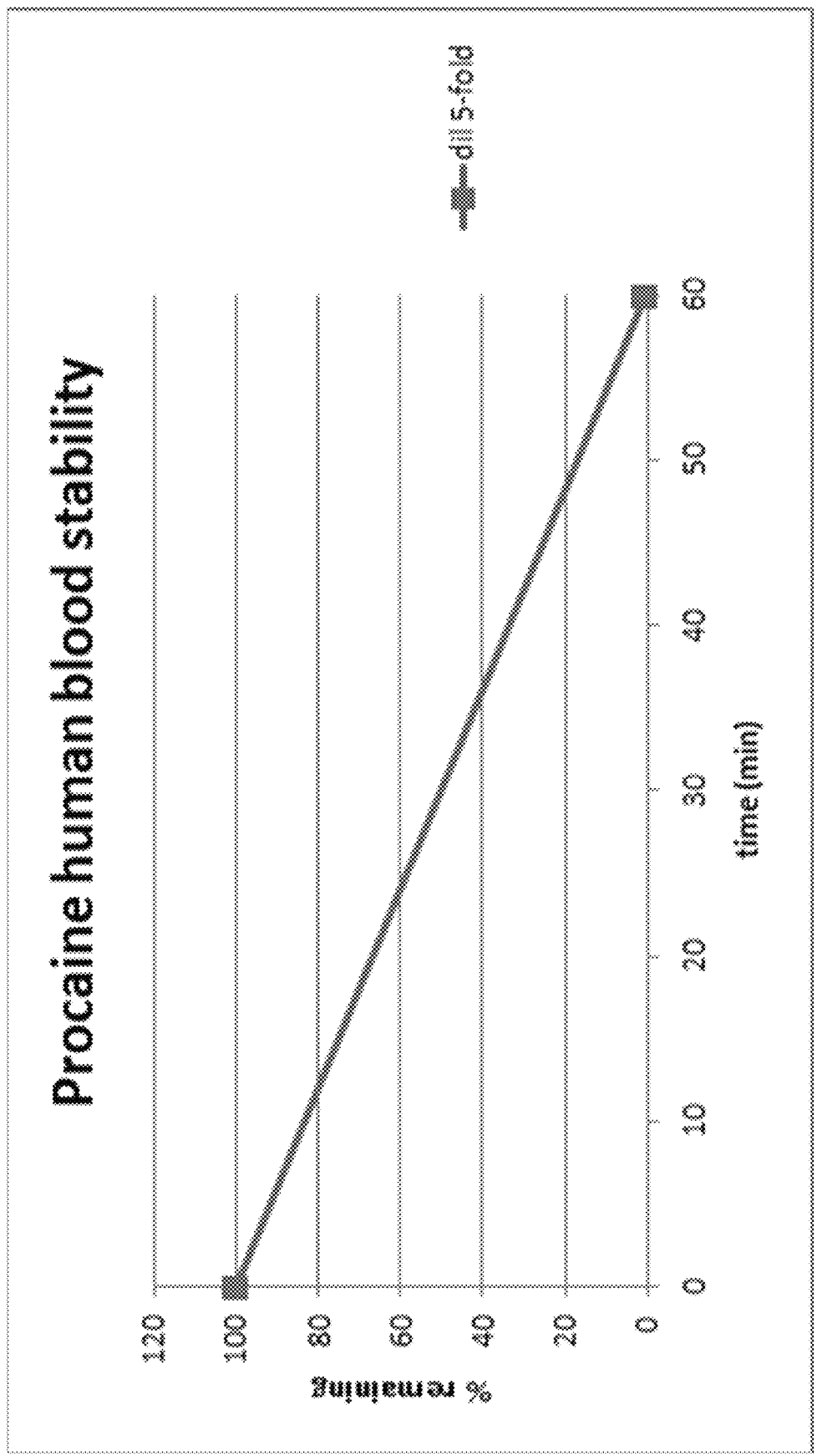
Figure 24:
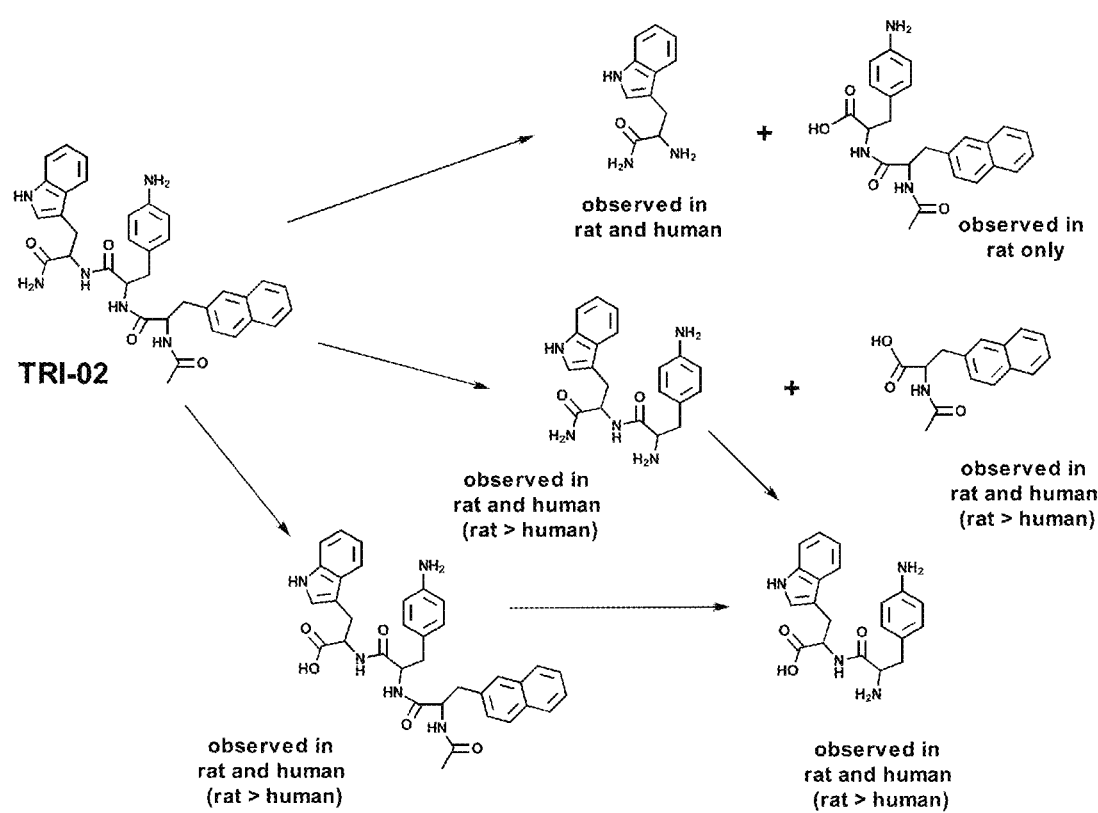
Figure 25:
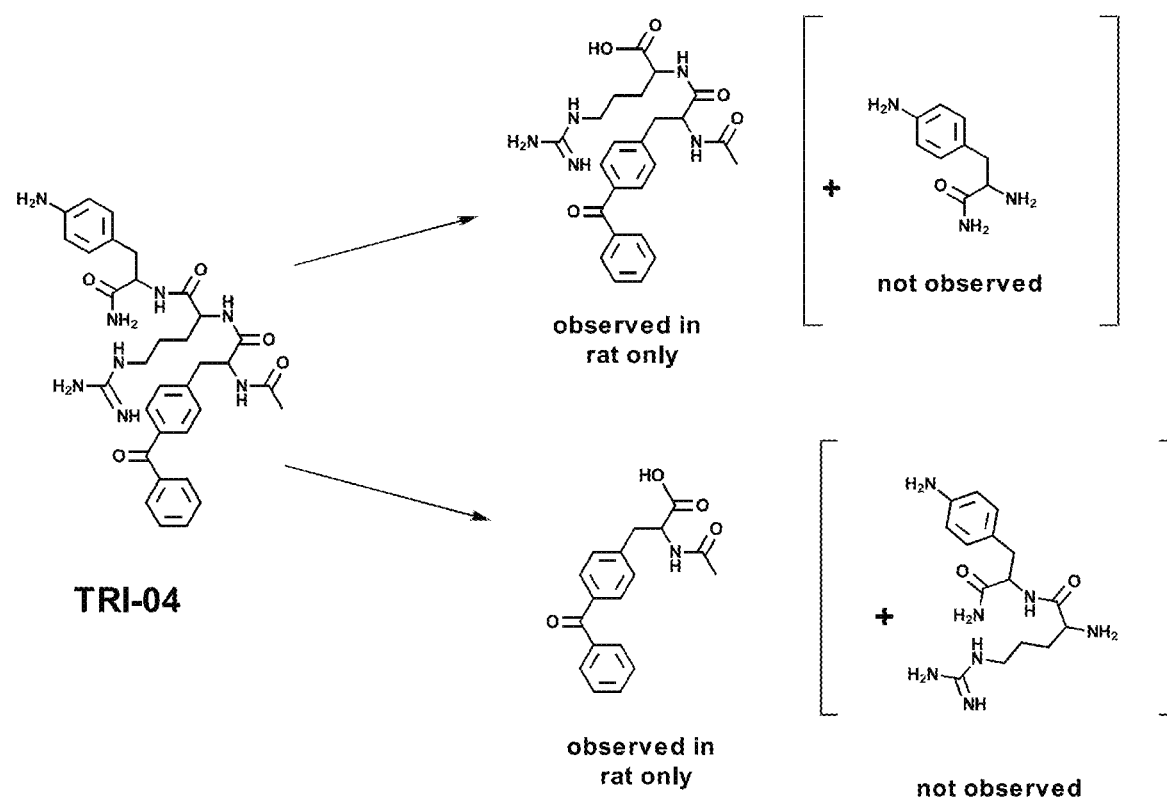
Figure 26:
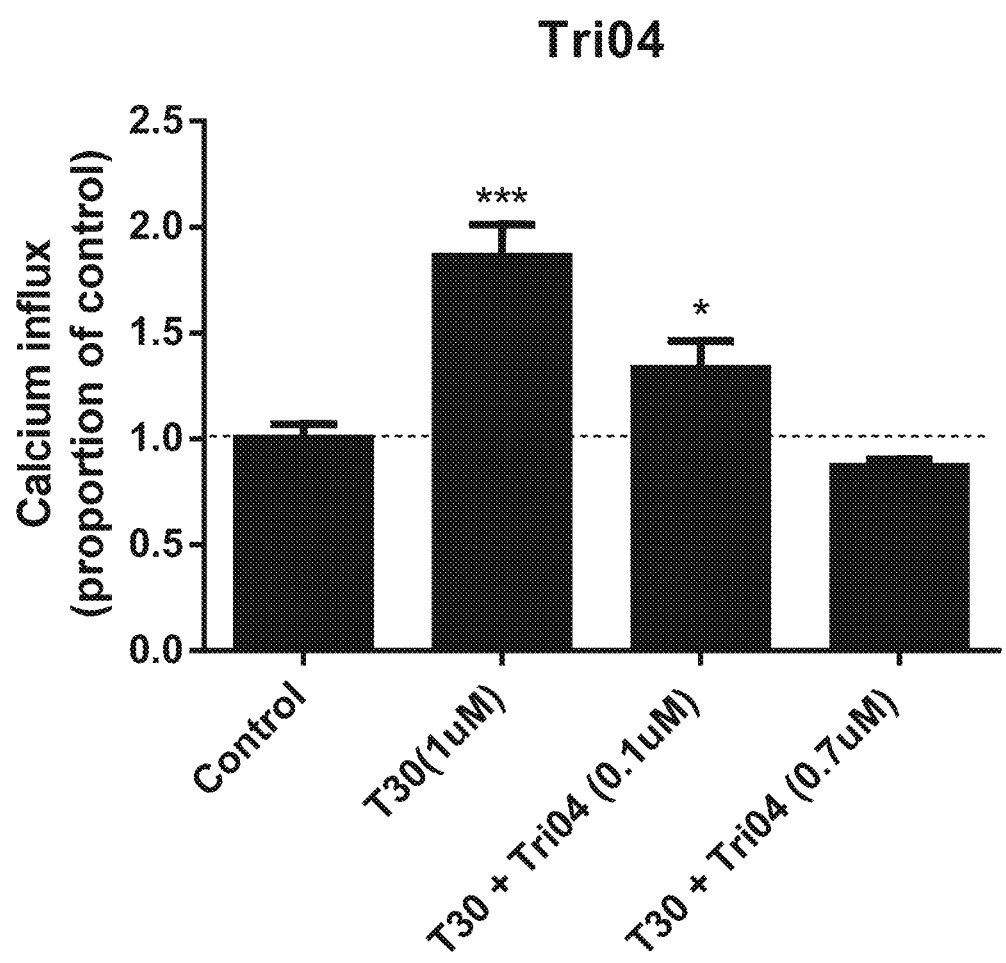
Figure 29:
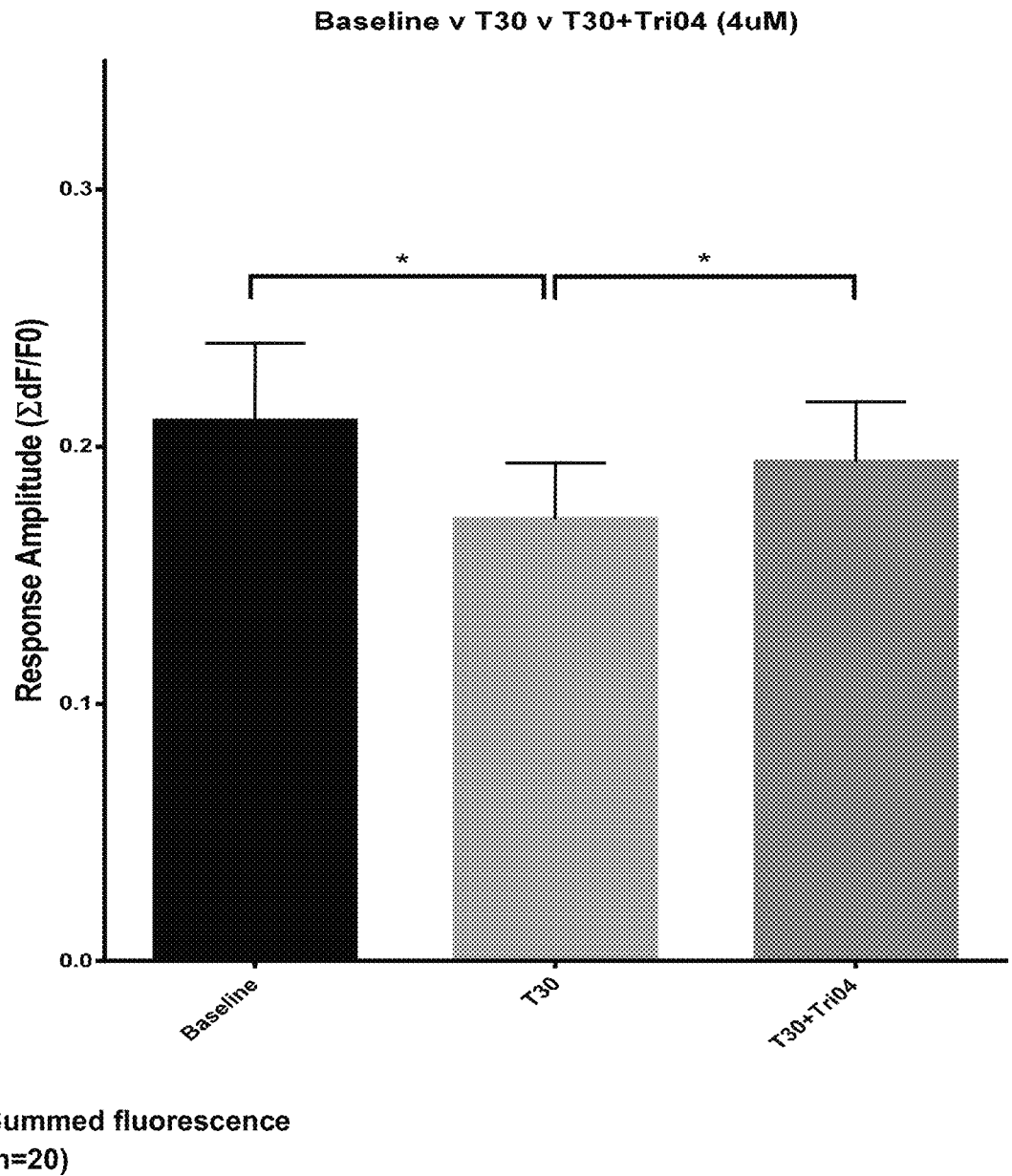

FIG. 4 merges the two views shown in FIGS. 2 and 3;

FIG. 5 shows pie charts of the amino acids or the chemical functions involved in the binding at each binding area (Area 1, 2, 3 or 4) in the α7 nicotinic-receptor, and shows if the residue results in an inert peptide, one which is active against toxic T30 or active against A-beta;

FIG. 6A-6F compares the distance between the amino acids binding in the different areas (Areas 1-4);

FIG. 7 is a list of chemical functionalities for binding to each of Areas 1, 2, 3 and 4 that are of specific relevance in providing protection against T30 toxicity;

FIG. 8 is a list of chemical functionalities for binding to each of Areas 1, 2, 3 and 4 that are of specific relevance in providing protection against beta amyloid production;

FIG. 9 shows cell culture data (i.e. acetylcholinesterase activity) for peptidomimetic compound 1 (i.e. Tri02);

FIG. 10 shows cell culture data (i.e. calcium ion influx) for peptidomimetic compound 1 (i.e. Tri02);

FIG. 11 shows the results of voltage-sensitive dye imaging (VSDI) on brain slices for control cyclic peptide NBP-14;

FIG. 12 shows the results of voltage-sensitive dye imaging (VSDI) on brain slices for peptidomimetic compound 1 (i.e. Tri02);

FIG. 13 shows correlation analysis of changes induced by addition of peptides against respective baseline response amplitude using voltage-sensitive dye imaging (VSDI) on brain slices. Changes in response amplitude induced by T30 were found to be negatively correlated with the amplitude of their respective baselines (A). Therefore, subsequent correlation analyses were carried out for each experiment in which exogenous peptides were perfused: B) T15, C) NBP14, D) Tri02, E) T30 in the presence of NBP14 and F) T30 in the presence of Tri02. Units on y-axis=$\Delta F/Fo$; x-axis=$\Sigma \delta F/Fo$;

FIG. 14 shows quantification of effects mediated by the addition of Tri02 and T30;

FIG. 15 shows a graph comparing the co-application of T30 and NBP14 against that of Tri02 and T30 at blocking the effects of T30 on activity within the basal forebrain. NBP14 co-application was able to totally block the T30-induced effects, whereas T30 w/Tri02 caused a similar but muted modulatory response;

FIG. 16 shows pharmacokinetic data for cyclic NBP-14 in rat blood;

FIG. 17 shows pharmacokinetic data for cyclic NBP-14 in human blood;

FIG. 18 shows pharmacokinetic data for peptidomimetic compound 1 (i.e. Tri02) in rat blood;

FIG. 19 shows pharmacokinetic data for peptidomimetic compound 1 (i.e. Tri02) in human blood;

FIG. 20 shows pharmacokinetic data for peptidomimetic compound 3 (i.e. Tri04) in rat blood;

FIG. 21 shows pharmacokinetic data for peptidomimetic compound 3 (i.e. Tri04) in human blood;

FIG. 22 shows pharmacokinetic data for procaine in rat blood;

FIG. 23 shows pharmacokinetic data for procaine in human blood;

FIG. 24 shows the blood breakdown products from peptidomimetic compound 1 (i.e. Tri02);

FIG. 25 shows the blood breakdown products from peptidomimetic compound 3 (i.e. Tri04);

FIG. 26 shows cell culture data (i.e. calcium ion influx) for peptidomimetic compound 3 (i.e. Tri04);

FIG. 27 shows (A) space-time maps of basal forebrain activity changes induced by addition of peptides (T30 and Tri04) against the baseline response amplitude using voltage-sensitive dye imaging (VSDI) on brain slices. In (B) is shown a graph comparing basal forebrain evoked activity for recordings with T30 and Tri04 (2 uM) with that of T30 alone in the basal forebrain;

FIG. 28 shows the fluorescence fractional change (response time-series, n=29) for recordings made in the presence of T30 alone or after co-application of T30 and its blocker Tri04 in comparison to the baseline condition; and FIG. 29 shows a bar graph of basal forebrain activity using the blocker Tri04 at 4 µM concentration. Tri04 co-application was able to totally block the T30-induced effects in the rat basal forebrain.

EXAMPLES

The inventors conducted an in silico study in order to design novel peptides and peptidomimetics, which would exhibit affinity for the α-7nChR receptor, and which would therefore block binding to its active site by the endogenous toxic T30 peptide (KAEFHRWSSYMVHW-KNQFDHYSKQDRCSDL—SEQ ID 11NO: 1). The in silico study helped to determine the chemical functionalities relevant for the protection against the T30 toxic action and beta-amyloid production by looking at the interaction between the receptor, and cyclic NBP-14 (i.e. AEFHRWSSYMVHWK—SEQ ID N0:2), which is known to provide this protection, as demonstrated in previous work (see WO 2015/004430). The following examples describe the in silico study as well as the structures of the various peptides and peptide mimetics that have been identified and tested in vitro.

Example 1—In-Silico Study to Design Novel Peptides which Inhibit α-7nChR Receptor By using computational analysis of the affinity of NBP-14 for the drug target receptor, and by structure-based studies, the inventors identified a range of smaller linear peptides with similar in-vitro properties to NBP-14 (SEQ ID NO:2). The theoretical interaction between 598 of these smaller linear peptides and the target α-7nChR receptor has been investigated. NBP-14 and the 168 linear peptides derived from the aforementioned computational analysis were chemically synthesised. NBP-14 and all of the 168 peptides were screened in vitro in PC12 cells, which are routinely used as a model system for neuronal differentiation and neurosecretion studies. Screening has been conducted in vitro for toxicity and neurodegenerative bioactivity, the latter via monitoring acetylcholinesterase activity and intracellular calcium levels. From this, a second generation of a range of new molecules with neurodegenerative protective properties against T30 have been identified using in silico analysis of the peptides that have been in vitro tested on PC12 cells to determine the main chemical functionality involved in binding to the receptor.

The docking of these compounds has been performed on the allosteric site of the α-7nChR receptor. The binding pocket in the receptor contains four areas (denoted Areas 1, 2, 3 and 4) that could be represented as shown in the FIGS. 1-4.

The in silico analysis comprised a comparison between the peptides to determine and differentiate the chemical features/functionalities that are specific to the protection against T30 toxicity and beta-amyloid production from the chemical features that are inert. FIGS. 2-4 summarizes the 3D structure of the binding pocket of α-7nChR with a colour coding based on the polarity.

The steps that were followed, as well as their outcomes, are summarised below:

Step 1: Comparison of the Amino Acids Binding in Each Specific Area of the Receptor In this analysis, each area was considered separately, only the amino acids that were binding to the area were considered. As shown in FIG. 5, presenting the pie charts of the amino acids or the chemical functions involved in the binding, this step did not reveal amino acids specifically binding in the different areas.

Step 2: Comparison of the Distance Between the Amino Acids Binding in the Different Areas In this analysis, the distance between the amino acids is measured taking into consideration the chemical functionality involved in the binding. These data, presented in FIG. 6 reveal no significant changes of distances between the inert variants and the variants with an activity against T30 toxicity and beta amyloid activity.

Step 3: Comparison of the Combination of Amino Acids Involved in the Binding

This step requires the analysis of the amino acids involved in the binding as a combination of amino acids necessary for the protection against T30 toxicity and beta amyloid production.

The results shown in the Tables 1 and 2 below indicate that 18 amino acid combinations appear to be necessary for the protection against T30 toxicity and 31 amino acid combinations appear to be necessary for the protection against beta amyloid production.

TABLE 1

Amino acid combinations that are protection against T30 toxicity

| Combination | Area 1 | Area 2 | Area 3 | Area 4 |
|---|---|---|---|---|
| 1 | His | Lys | Phe | Trp |
| 2 | Amide | Phe | His | — |
| 3 | His | Met | Trp | — |
| 4 | Amide | Arg | Glu | — |
| 5 | Trp | His | Tyr | Met |
| 6 | Arg | Trp | Tyr | Met |
| 7 | Phe | N-ter | Arg | His |
| 8 | Trp | Met | Phe | Lys |
| 9 | Arg | Amide | Tyr | — |
| 10 | Arg | Met | Tyr | — |
| 11 | Lys | Trp | Tyr | — |
| 12 | Trp | Lys | Met | His |
| 13 | Lys | His | Tyr | — |
| 14 | Trp | Lys | N-ter | — |
| 15 | Trp | Serer | Phe | Arg |
| 16 | N-ter | Tyr | His | Yrp |
| 17 | Amide | — | Glu | — |
| 18 | His | — | Ser | — |

TABLE 2

Amino acid combinations that are protection against beta amyloid production

| Combination | Area 1 | Area 2 | Area 3 | Area 4 |
|---|---|---|---|---|
| 1 | Lys | Glu | C-ter | Phe |
| 2 | Arg | — | Tyr | Trp |
| 3 | Trp | — | Tyr | Met |
| 4 | — | — | Tyr | Met |
| 5 | Tyr | — | Hi | N-ter |
| 6 | Trp | His | Tyr | Arg |
| 7 | Trp | — | Tyr | Met |
| 8 | Glu | — | Trp | Lys |
| 9 | His | Trp | Tyr | Met |
| 10 | Trp | — | Tyr | Met |

TABLE 2-continued

| Amino acid combinations that are protection against beta amyloid production | | | | |
|---|---|---|---|---|
| Combination | Area 1 | Area 2 | Area 3 | Area 4 |
| 11 | N-ter | Met | — | — |
| 12 | His | Lys | Phe | Trp |
| 13 | His | — | Tyr | Met |
| 14 | N-ter | His | Tyr | — |
| 15 | Trp | Lys | Met | His |
| 16 | — | N-ter | C-ter | — |
| 17 | Tyr | — | N-ter | Lys |
| 18 | Lys | Trp | Phe | — |
| 19 | N-ter | Lys | Phe | Trp |
| 20 | His | Phe | Amide | Glu |
| 21 | Trp | Arg | Phe | His |
| 22 | Tyr | Lys | His | — |
| 23 | Trp | His | Tyr | — |
| 24 | N-ter | Trp | His | Val |
| 25 | Trp | Ser | His | Arg |
| 26 | Ala | His | Tyr | — |
| 27 | His | Phe | Trp | Arg |
| 28 | Amide | Trp | Val | His |
| 29 | N-ter | — | Arg | His |
| 30 | His | — | Ser | — |
| 31 | His | Amide | — | — |

In view of these results, the inventors were then able to determine the ranking of the amino acid residues involved in the binding within each area (Areas 1-4) of the receptor, and thus the chemical functionalities that are of specific relevance in providing protection against both T30 toxicity and beta amyloid production, see FIGS. 7 and 8, respectively.

The inventors were able to conclude that each area requires specific chemical functionalities that are summarised in the Table 3.

TABLE 3

| The type of interaction occurring in each area of the allosteric site of the α-7nChR receptor | |
|---|---|
| Area | Type of interaction |
| 1 | Hydrogen bond |
| 2 proximal | Hydrogen bond |
| 2 distal (optional) | Hydrophobic |
| 3 proximal | Hydrophobic |
| 3 distal | Hydrogen bond |
| 4 distal (optional) | Hydrogen bond |

Accordingly, in view of these findings, the inventors have demonstrated that a suitable peptide which would block the toxic effects of endogenous T30 by preferentially blocking the active site of the nicotinic receptor.

Example 2—Design and Production of Peptidomimetics

An alternative approach was then used to design and isolate novel peptidomimetic compounds which could (as with the peptides described in Example 2) outcompete T30 for the allosteric active site of the nicotinic receptor. Thus, a further in silico study was carried out in which computation solvent mapping was conducted over the starting initial X-ray structure of the allosteric site of the α-7nChR receptor. This analysis was aimed to elucidate the preferential solvent interaction at the binding site as well as to locate the presence of hot spots (hydrophobic, aromatic, polar or charged). This method identified the expected chemical features required by the ligand in order to become active.

The IPRO solvent analysis unraveled the high hydrophobic nature of the binding site. Perfect overlapping between IPRO solvent mapping prediction and T14 peptide docking was observed.

Based on the solvent mapping analysis, the T14 structure was used to generate linear libraries of tripeptides and tetrapeptides. In this step more than 500,000 peptidomimetics were generated for a further evaluation. The peptidomimetics were then evaluated by AutoDock Vina docking engine. The theoretical affinities as well as ligand promiscuity (i.e, tendency to bind in multiple binding sites or different binding modes, denoted by a low intra-RMSD) were taken into account for the analysis. This analysis resulted in five candidate peptidomimetic compounds which are shown below, in which the higher the score is (an absolute value), the better the affinity and the higher the probability the compound is active.

Compound 1—Tri02 (Score: −10.2)

4-((S)-2((S)-2-acetamido-3-(naphthalene-2-yl)propanamido)-3-(((S)-1-amino-3-(1H-indol-3-yl)-1-oxopropan-2-yl)amino)-3-oxopropyl)benzenaminium Compound 2—Tri03 (Score: −9.8)

(3S,5S)-1_(((S)-2-acetamido-3-(naphthalene-2-yl)propanoyl)-5-(((S)-1-amino-6-((amino(iminio)methyl)amino)-1-oxohexan-2-yl)carbamoyl)pyrrolidin-3-aminium Compound 3—Tri04 (Score: −9.4)

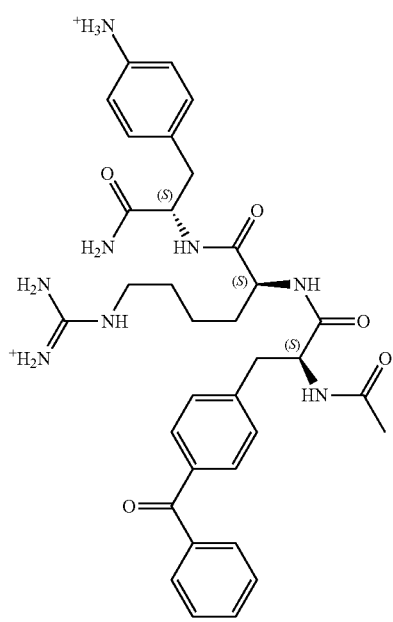

4-((S)-2-((S)-2-((S)-2-acetamido-3-(4-benzoylphenyl)propanamido)-6-((amino(iminio)methyl)amino)hexanamido)-3-amino-3-oxopropyl)benzenaminium Compound 4—Tri05 (Score: −9.6)

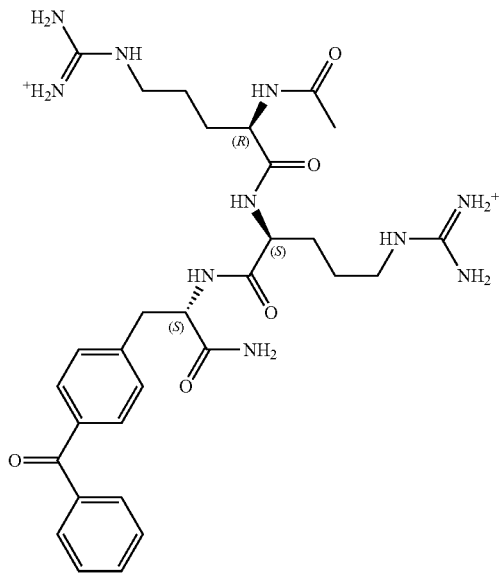

(((R)-4-acetamido-5-(((S)-5-((amino(iminio)methyl)amino)-1-(((S)-1-amino-3-(4-benzoylphenyl)-1-oxopropan-2-yl)amino)-1-oxopentan-2-yl)amino)-5-oxopentyl)amino)(amino)methaniminium Compound 5—Tri06 (Score: −8.9)

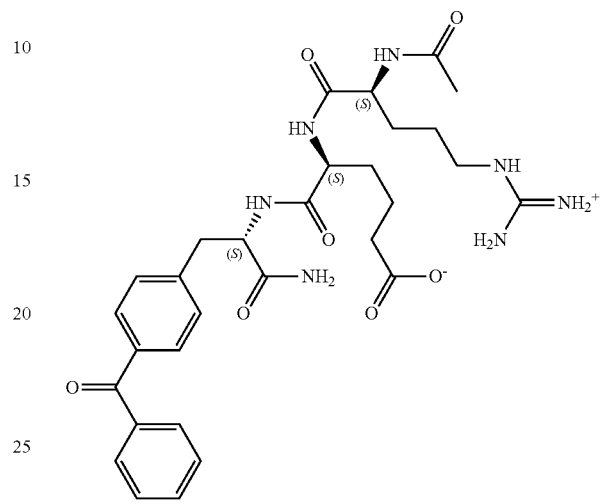

(S)-5-(((S)-2-acetamido-5-((amino(iminio)methyl)amino)pentanamido)-6-(((S)-1-amino-3-(4-benzoylphenyl)-1-oxopropan-2-yl)amino)-6-oxohexanoate Example 3—Synthesis of Identified Compounds Materials and Methods Compounds 1 and 3 from Example 2 were synthesised by Genosphere Biotechnologies and analysed for purity using RP-HPLC (>$_{99}$% pure), and mass by mass spectroscopy (average MS 604.79 for Triol and 628.83 for Tri04).

Brief Stepwise Description of Synthesis of TRI02—Sequence: [acetyl]-[2Nal][4nh2-F]-Trp-[amide]

1) Boc-Trp-OH+ClooEt+NH$_3$.H2O-Boc-Trp-NH2, reaction in THF, extracted by acetic ether.

2) Boc-Trp-NH2,4NHcl, removed Boc−, obtained H-Trp-NH2.Hcl, precipitation reaction by diethyl ether.

3) (2-Naphtyl)-Ala+Acetic Anhydride-Ac-(2-Naphtyl)-Ala-OH, reaction THF/H2O, extracted by acetic ether.

4) Boc-(4-NH2)-Phe-OH+H-Trp-NH2.Hcl-Boc-(4-NH2)-Phe-Trp-NH2, reaction in DMF, extracted by acetic ether.

5) Boc-(4-NH2)-Phe-Trp-NH2,4NHcl, removed Boc−, obtained H-(4-NH2)-Phe-Trp-NH2.Hcl, precipitation reaction by diethyl ether.

6) Ac-(2-Naphtyl)-Ala-OH+H-(4-NH2)-Phe-Trp-NH2.Hcl-Ac-(2-Naphtyl)-Ala-(4-NH2)-Phe-Trp-NH2 reaction in DMF, extracted by acetic ether.

7) Purification

Brief Stepwise Description of Synthesis of TRI04—Sequence: [acetyl]-[bpa]R[4NH2-F]-[amide]

1) Rink Amide MBHA.Resin Soak in DCM for 30 mins, pumped dry, washed by DMF for 3 times, pumped dry.

2) Add Fmoc-(4-NH2)Phe-OH,DIEA,HBTU,DMF,N2, reaction for 30 mins, pumped dry, washed by DMF for 6 times, pumped dry.

3) Add piperidine/DMF to remove Fmoc−, reaction for 20 mins, pumped dry, washed by DMF for 3 times, pumped dry.

4) Add Fmoc-Arg(Pbf)-OH,DIEA,HBTU,DMF,N2, reaction for 30 mins, pumped dry, washed by DMF for 6 times, pumped dry.

5) Repeat step 3.

6) Add Fmoc-Bpa-OH,DIEA,HBTU,DMF,N2, reaction for 30 mins, pumped dry, washed by DMF for 6 times, pumped dry.

7) Repeat step 3.

8) Add Acetic Anhydride/DMF,N2, reaction for 30 mins, pumped dry, washed by DMF for 3 times, pumped dry, washed by DCM for 3 times, pumped dry, washed by MeOH for 3 times, pumped dry.

9) Peptide cleaved from resin, pumped dry, precipitation reaction by diethyl ether, obtain the crude peptide, centrifugal drying.

10) Purification

Example 4—Evaluation of Compound 1 (Tri02) and Compound 3 (Tri04) in Cell Cultures The inventors tested T30, NBP-14, and Tri02 in cell culture studies to determine their effects on acetylcholinesterase activity and calcium influx, and the effects of Tri04 on calcium influx.

Materials and Methods

1. AChE Activity Assay

AChE activity was measured using the Ellman reagent that measures the presence of thiol groups as a result of AChE activity. In the case of the G4 experiment, AChE (G4) activity was tested alone and also together with either NBP14 or Tri peptides. PC12 cells were plated the day before the experiment as for the cell viability assay. Cells were treated with T30 (1 µM) alone or combined with NBP14 or Tri peptide (0.5 µM). After treatment, supernatant (perfusate) of each treatment was collected and 25 µL from each condition were added to a new flat bottomed 96 well plate followed by the addition of 175 µl of Ellman reagent (Solution A: $KH_2PO_4$ 139 mM and $K_2HPO_4$ 79.66 mM, pH 7.0; solution B (substrate): Acetylthiocholine Iodide 11.5 mM; Solution C (Reagent): 5,5'-dithiobis(2-nitrobenzoic acid) 8 mM and $NaHCO_3$ 15 mM). The Ellman reagent was prepared as a mixture of the 3 solutions in a ratio 33(A):3(B):4(C). Absorbance measurements were taken for an interval of 60 minutes across experiments at 405 nm in a Vmax plate reader (Molecular devices, Wokingham, UK).

2. Calcium Fluorometry

PC12 cells were plated in 200 µl of Dulbecco's Modified Eagle's medium (DMEM) plus 2 mM of L-glutamine medium the day before the experiment in 96 well plates. On the day of the experiment, the Fluo-8 solution (Abcam) was prepared as described by the provider by adding 20 µl of Fluo-8 in the assay buffer that contains 9 ml of Hank's Balanced Salt Solution (HBSS) and 1 ml of pluronic F127 Plus. Subsequently, 100 µl of growth medium was removed and 100 µl of Fluo-8 solution were added. Treatments with T30 in conjunction with NBP14 or Tri peptides were added and incubated for 30 minutes in the incubator and 30 minutes room temperature. After 1 h, the plate was placed in the fluorescence plate reader (Fluostar, Optima, BMG Labtech, Ortenberg, Germany). Before reading the fluorescence, PNU282987 1 µM, an alpha7 specific agonist of the nicotinic receptors, was prepared and placed in the Fluostar injector. For each well, the reading was formed by a basal fluorescence reading followed by PNU282987 injection that induced an increase of calcium via nicotinic receptors.

3. Data Analysis

In each of the different cell techniques, the statistics analysis was performed with the average of the percentage values of 3 or more experiments. Comparisons between multiple treatment groups and the same control were performed by one-way analysis of variance (ANOVA) and Tukey's post-hoc tests using GraphPAD Instat (GraphPAD software, San Diego, California). Statistical significance was taken at a p value<0.05.

Results

The results for Triol are shown in FIGS. 9 and 10, in which n values shown on the subsequent graphs refer to number of repeated experiments. As can be seen, 1 µM T30 increases calcium influx and AChE activity, and, as shown in previous work (see WO 2015/004430), 1 µM NBP14 protects against these toxic effects.

In addition, as can be seen in the Figures, Triol also clearly protects against the toxic effects of T30 by reducing both calcium influx and AChE activity. As such, the inventors are convinced that Triol is neuroprotective, and, due to its smaller size than NBP-14, will have a much greater chance of passing through the blood-brain barrier.

The results for Tri04 are shown in FIG. 26. As can be seen, Tri04 also protects the toxic effects of T30 by reducing calcium influx.

Example 5—Evaluation of Compound 1 in Brain Slices

The inventors tested NBP-14 and Triol in brain slice studies using voltage-sensitive dye imaging (VSDI).

Materials and Methods

1. Brain Slice Preparation

Male Wistar rats (14 days old) were anaesthetised using isoflurane (~15 ml, 100% w/w). Isoflurane was applied to the cotton bed at the bottom of an anaesthetic chamber (glass box 20×15×15 cm) where rats were then placed for approximately 45 s until complete anaesthesia was reached. The hind paw of each anaesthetised rat was pinched to check for the appropriate depth of anaesthesia. Upon confirmation of anaesthesia, rats were quickly decapitated, with the brain being quickly removed and immersed in ice cold oxygenated 'slicing' artificial cerebrospinal fluid (aCSF in mmol: 120 NaCl, 5 KCL, 20 $NaHCO_3$, 2.4 $CaCl_2$ 2 $MgSO_4$, 1.2 $KH_2PO_4$, 10 glucose, 6.7 HEPES salt and 3.3 HEPES acid; pH=7.1). Coronal slices (400 µm thick) were then taken from a block of brain containing the basal forebrain, namely the MS-dBB complex (between +9.20 and +9.48 mm Interaural and +0.48 and +0.2 mm Bregma, FIG. 4A) and the somatosensory barrel field cortex (SiBF, between +8.08 and +7.20 mm Interaural and −0.92 mm and −1.80 mm Bregma) (Paxinos and Watson, 1998) using a Vibratome (Leica VTi000S).

Slices were then transferred to a bubbler pot containing oxygenated aCSF at room temperature (recording aCSF in mmol: 124 NaCl, 5 KCL, 20 $NaHCO_3$, 2.4 $CaCl_2$ 2 $MgSO_4$, 1.3 $KH_2PO_4$, 10 glucose; pH=7.4) which was identical to that used in VSDI (voltage sensitive dye imaging) recording. Slices were then left for approximately 1-1.5 hours before preparing them for VSD staining.

2. VSD Setup

Slices were placed in a dark, high humidity chamber filled with aCSF bubbled with 95% $O_2$, 5% $CO_2$. Once there, the dye solution (4% 0.2 mM styryl dye pyridinium 4-[2-[6-(dibutylamino)-2-napthalenyl]-ethenyl]-1-(3-sulfopropyl) hydroxide (Di-4-NEPPS), Invitrogen, Paisley, UK in 48% aCSF, 48% foetal bovine serum, 3.5% DMSO and 0.4% cremophore EL) (Tominaga et al., 2000) was applied to the slices for 20-25 minutes before being transferred back to a bubbler pot containing oxygenated aCSF kept at room temperature for 30 minutes.

When starting the VSDI recordings, slices were placed in the recording bath on a small piece of filter paper to allow the flow of oxygenated aCSF on the underside of the slice and in order to keep it alive. The slice was then weighed down by a home-made plastic grid that was placed on top of the slice. The perfusing bath solution was heated to 30±1° C. by a stage heater. A concentric bipolar stimulating electrode (FHC, Maine, USA) was placed in the ventral diagonal band of the basal forebrain with stimulation being set to 30V. For the acquisition of VSD data, 2 dimensional images, equivalent to 88×60 pixels, were recorded using the MiCamo2 High Resolution camera (Brain Vision, Japan) with BV_Analyze imaging software. Acquisition of images was coupled to Spike2 V4.23 software (CED Ltd, Cambridge, UK) in order to align the image capture with the stimulation protocol (every 28 s with 30 repeats) via the Micro 1401 MkII. (CED Ltd, Cambridge, UK). Light was generated using an Osram halogen xenophot 64634 HLX EFR Display/Optic lamp and was filtered to emit green (530±10 nm) light using a MHF-G150LR (Moritex Corporation) coupled to the MiCamo2 High resolution imaging system and filtered the emitted fluorescence through a >590 nm high pass filter.

3. Drug Preparation and Application

Acetylcholinesterase (AChE)C-terminus 30 amino acid peptide (T30; sequence: 'N'—KAEFHRWSSYMVHWKNQFDHYSKQDRCSDL—SEQ ID NO:1), the cyclic version of the active 14 amino acid region of T30 (NBP14; sequence: c[AEFHRWSSYMVHWK]—SEQ ID NO:2; c[ ]=cyclic, N-terminal to C-terminal) and the inert 15 amino acid peptide contained within the T30 sequence (T15; sequence: 'N'—NQFDHYSKQDRCSDL—SEQ ID NO:3) were custom synthesised and purchased from Genosphere Biotechnologies (Paris, France) at >99% purity. The linear peptidomimetic, Triol was designed in silico by Iproteos (Barcelona, Spain) and synthesised and purchased from Genosphere Biotechnologies at >99% purity. All drug and peptide stocks were prepared in frozen aliquots prior to experiments. For the production of perfusion solutions, stock solutions were thawed and added to recording aCSF as appropriate and bath applied at a constant rate of 1.5 ml/min perfusion using the Minipulse 3 peristaltic pump (Gilson Scientific Ltd., Bedfordshire, UK). Each experimental trial lasted 52 minutes, with 20 minutes to establish a baseline recording (perfusion with recording aCSF only), 12 minutes to allow the drug solution to perfuse into the bath as well as to let the dye molecules reseat themselves in the cell membranes and finally, a 20 minute recording period measuring the response in the presence of the drug solution.

4. Data Analysis and Statistics

From the 2 dimensional images generated with each drug condition, the critical data such as the time-course of activation, intensity and spread of the overall fluorescent signal were extracted. These data were processed using a custom script to convert them into usable MatLab (Mathworks Inc. Massachusetts, US) files and then analysed using a Matlab toolbox specifically made for VSDI data analysis (Bourgeois et al., 2014). This toolbox allows for the selection of a fixed region of interest (ROI) geometry that can be applied to every slice, in order to extract and collate the data from an identical ROI across all slices used in each experiment. For the basal forebrain slices, the ROI that will be used is the MSdBB complex, chosen as it encompasses the MS (medial septal nuclei), VDB (ventral diagonal band) and HDB (horizontal diagonal band). More crucially, this ROI was chosen in order to include the entirety of the evoked response. This response can be plotted as a single averaged time series or over space and time in a 'space-time map' so as to provide a qualitative description of the data. However, in order to produce quantifiable values, the area underneath the time series was calculated (summed fluorescence fractional change) between the moment of stimulation (t=0) and 156 ms after that. Due to the variability of responses seen between each individual slice, the raw data generated from each experiment was normalised with respect its own baseline to give normalised fluorescence values. This method of quantification was chosen in order to account for the multiple components of the signal generated by VSDI (Chemla and Chavane, 2010) namely the immediate peak and the long latency response (Badin et al., 2016). Statistics were carried out in Prism Graphpad 6.

5. Analysis of Modulatory Peptides

Throughout the experiments in which T30 was used, an increase or a decrease in signal was observed. Thus upon averaging these results together, no change was detected. However, given the past observed modulatory effects of this peptide in various preparations (Bon and Greenfield, 2003, Day and Greenfield, 2004, Greenfield et al., 2004, Badin et al., 2013) and the fact that the changes induced by application of T30 in this type of preparation are moderately negatively correlated (r=−0.4286, p=0.0257, Spearman's rank correlation, n=27, FIG. 13A) with baseline response amplitude, it was decided that these results should be dichotomised by whether an increase or a decrease was seen.

Subsequently, a similar correlation analysis was performed for each experiment in which an exogenous compound was added (FIG. 13). Upon determination of a significant correlation, data was then categorised based on whether and increase or a decrease was seen.

Results

Referring to FIGS. 2, 11 and 12, addition of 4 μM Tri02 recapitulates results seen with application of 4 μM NBP14.

Referring to FIG. 11, addition of NBP14 (4 uM) to the perfusate induced small, non-significant alterations to the magnitude (summed fluorescence) of evoked responses. Though insignificant, these small induced changes were found to be inversely correlated with magnitude of baseline response; as a result, data were split into trials which caused slight decreases (left histograms) and those which caused increase (right histograms), both in real (top) and normalised (bottom) data format. If considered together, the dataset would show no change from baseline (as increases and decreases would cancel each other out), yet it was crucial to check that no significant effects were induced by NBP14 even when the fluorescence changes were considered separately.

As shown in FIG. 12, addition of Tri02 (4 uM) to the perfusate induced small alterations to the magnitude (summed fluorescence) of evoked responses, with induced decreases (n=8 of ii total) showing a significant deviation from normalised baseline level (bottom left histogram, p<0.05). These changes were also found to be inversely correlated with magnitude of baseline response; as a result, data were split into trials which caused decreases (left histograms) and those which caused increases (right histograms), both in real (top) and normalised (bottom) data format. If considered together, the dataset would show no change from baseline (as increases and decreases would cancel each other out), yet it was crucial to check that no significant effects were induced by NBP14 even when the fluorescence changes were considered separately.

Analysis of Modulatory Peptidomimetics

Referring to FIG. 13, there is shown correlation analysis for Tri02 (4 uM) and T30 (2 uM) data (n=15) showing that their co-perfusion induces some changes to the magnitude of evoked responses, with some slices featuring slight increases in activity (n=6) whilst most showed slight decreases (n=9). This correlation was found to be significant (p=0.0405; $r^2$=−0.534), providing justification to split the data into those that showed increases and decreases in evoked activity as a result of Tri02 and T30 application, just as was done for the addition of NBP14 and Tri02 (FIGS. 11 & 12, respectively).

Referring to FIG. 14, there is shown quantification of effects mediated by the addition of Tri02 and T30: Both in the case of induced increases and decreases, Tri02 was not found to protect against T30-induced deviations from baseline, with significant decreases (left panel, $p<0.01$, n=9) and increases (right panel, $p<0.05$, n=6) reported in overall effects.

As shown in FIG. 15, overall line graph of normalised effects respective to baseline for experiments testing the effects of normal aCSF (black line), 2 uM T30 (red lines), T30 (2 uM) and 4 uM NBP14 (blue lines), T30 (2 uM) and 4 uM Tri02, control NBP14 (4 uM) experiments (FIG. 11, orange lines), control Tri02 (4 uM) experiments (FIG. 12, purple lines). This graph shows the normalised decreases relative to baseline and each other, with T30 alone inducing the greatest deviation, and Tri02 showing some efficacy in blocking those T30-induced deviation, yet with significant changes still taking place in their co-perfusion (green lines).

Example 6—Pharmacokinetics

The inventors investigated the degradation products of NBP-14, Tri-02 and Tri-04 in rat and human blood.

Procedure

Test compounds were spiked at 10 μg/ml into either PBS or blood (Male Wistar rat or Human) diluted with PBS, and a series of samples taken according to the following scheme:

| | Time (min) | | | | |
|---|---|---|---|---|---|
| Matrix | 0 | 5 | 15 | 30 | 60 |
| PBS control | A1 | A2 | A3 | A4 | A5 |
| Blood dil 5-fold | B1 | B2 | B3 | B4 | B5 |
| Blood dil 20-fold | C1 | C2 | C3 | C4 | C5 |
| Blood dil 50-fold | D1 | D2 | D3 | D4 | D5 |

Procaine, a compound known to be unstable in blood, was included as a positive control (ran with 5-fold diluted blood only). The sampling procedure was to add an aliquot to ice-cold acetonitrile, centrifuge, and store the supernatant on dry ice until analysis. Analysis by UHPLC-TOF mass spectrometry using electrospray ionisation was performed on the same day as the incubations were performed.

Results

Procaine showed 60% and 100% turnover in 5-fold diluted rat and human blood, respectively, indicating acceptable metabolic competence for the blood used, as shown in FIGS. 22 and 23.

Stability data for NBP-14, Tri-02 and Tri-04 in rat and human blood is plotted in FIGS. 16-21. NBP-14 exhibited good stability, and no degradants were detected. Tri-02 exhibited some instability in both 5-fold and 20-fold diluted rat and human blood, and a variety of degradants were detected as indicated in FIG. 24. Tri-04 exhibited better stability than TRI-02, but nevertheless some degradants were still detected in 5-fold diluted rat blood, as indicated in FIG. 25. Accordingly, Tri-02 and Tri-04 are stable and so are good drug candidates.

Example 7—Evaluation of Compound 3 in Brain Slices

The inventors tested Tri04 in brain slice studies using voltage-sensitive dye imaging (VSDI).

Materials and Methods

1. Brain Slice Preparation

Brain slices were prepared as in Example 5.

2. VSD Setup

Slices were placed in a dark, high humidity chamber filled with aCSF bubbling with 95% O2e5% CO2. Once there, the dye solution (4% 0.2 mM styryl dye pyridinium 4-[2-[6-(dibutylamino)-2-aphthalenyl]-ethenyl]-1-(3-sulfopropyl) hydroxide (Di-4-ANEPPS, Invitrogen, Paisley, UK) (Tominaga et al., 2000) in aCSF 48%, fetal bovine serum 48%, DMSO 3.5% and cremophore EL 0.4%) was applied to the slices for 20-25 min before being transferred to an aCSF bubbler pot (room temperature, 22 C+/−1.5 C) for 1 h to wash off excess dye and recover.

When starting VSD recordings, slices were placed in the recording bath on a small piece of filter paper to keep slice alive and was weighed down appropriately using a homemade plastic grid placed atop the slice. The perfusing bath solution was heated to 30+/−1 C by a stage heater. A concentric bipolar stimulating electrode (FHC, Maine, US) was placed in the ventral diagonal band of the basal forebrain with stimulation being set at 30 V. For acquiring of VSD data, 16-bit images were recorded with 1 ms resolution with a digital camera (Brain Vision MiCAM Ultima R3-V20 Master) with Ultima 2004/08 imaging software (Brain Vision) coupled to Spike 2 V6.0 (CED Ltd, Cambridge, UK) which was used to trigger stimulations with respect to appropriate ISI. Light was generated using an Osram halogen xenophot 64634 HLX EFR Display/Optic lamp and was filtered to emit green (530+/−10 nm) light using a MHF-G150LR (Moritex Corporation) coupled to MiCAM Ultima ultra-fast imaging system and filtered the emitted fluorescence through a >590 nm high-pass filter.

3. Drug Preparation and Application

The linear peptidomimetic, Tri04, was designed in silico by Iproteos (Barcelona, Spain) and synthesised and purchased from Genosphere Biotechnologies at >99% purity. All drug and peptide stocks were prepared in frozen aliquots prior to experiments. For the production of perfusion solutions, stock solutions were thawed and added to recording aCSF as appropriate and bath applied at a constant rate of 1.5 ml/min perfusion using the Minipulse 3 peristaltic pump (Gilson Scientific Ltd., Bedfordshire, UK). Each experimental trial lasted 52 minutes, with 20 minutes to establish a baseline recording (perfusion with recording aCSF only), 12 minutes to allow the drug solution to perfuse into the bath as well as to let the dye molecules reseat themselves in the cell membranes and finally, a 15 minute recording period measuring the response in the presence of the drug solution.

5. Analysis of Modulatory Peptides

Throughout the majority of experiments in which T30 was used, a decrease in signal was observed. T30 induced a net inhibition (n=21) in recorded VSDI signal in the basal forebrain of p14 rats, this value actually includes a minority of instances where negligible or marginally positive effects were seen during T30 perfusion (Badin et al., 2016).

Results and Discussion

Referring to FIGS. 27, 28 and 29, addition of 4 μM Tri04 recapitulates results previously seen with the application of 4 μM NBP14, while 2 μM Tri04 in the perfusion solution determines a significant effect on basal forebrain population activity.

Analysis of Modulatory Peptidomimetics

Referring to FIG. 27A, there is shown that space-time maps exhibit a recovery in basal forebrain activity due to the presence of 2 μM Tri04 in the perfusate containing 2 μM of T30 (n=29). More specifically, 2 μM Tri04 determines a reversal of the inhibitory effect of T30 over activity measured by direct stimulation of the rat basal forebrain.

Referring to FIG. 27B, bar graphs relative to the 3 recording epochs show changes in the evoked response after Tri04 application, confirming that 2 μM Tri04 co-perfusion induces an increase in network activity (n=29, p=0.06, two-tailed paired t-test) caused by a inhibition of T30-induces effects.

Referring to FIG. 28, there is shown that response time-series across the three recording conditions (baseline, T30 application to the artificial cerebro-spinal fluid (aCSF) and co-application of T30 and Tri04 to the aCSF show a similar activation profile for T30 recordings and T30+Tri04 for the first 100 msec, while a higher activity in recordings made in presence of Tri04 is detectable afterwards, confirming a protective role of Tri04 over T30.

Referring to FIG. 29, there is shown bar graphs relative to three recording conditions. The co-perfusion of 4 μM Tri04 in the artificial cerebro-spinal fluid (aCSF) containing 2 UM T30 determines a significant effect reversing T30 activity. In particular, Tri04 has been found to be protective against T30-induced deviations from the baseline with a significant increase (n=20, p<0.05, two-tailed paired t-test) in basal forebrain activity in comparison to recordings in the presence of T30 alone. Therefore, Tri04 shows some efficacy blocking T30 toxic effects on meso-scale network activity.

The invention claimed is:

1. A method of treating or ameliorating Alzheimer's disease, the method comprising administering, to a subject in need of such treatment, a therapeutically effective amount of a compound of Formula (I):

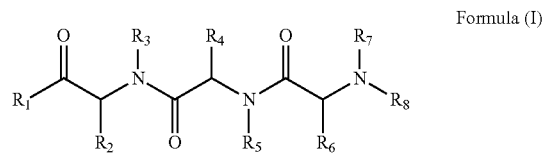

Formula (I)

wherein:
R₁ is —NR₉R₁₀ or —OH, either:

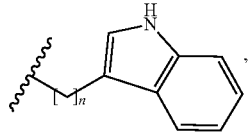

R₄ is

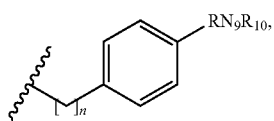

and R₆ is

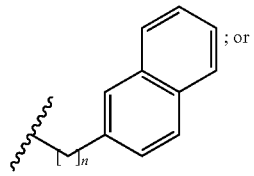

(ii) R₂ is

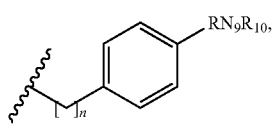

R₄ is

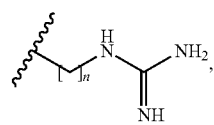

and R₆ is

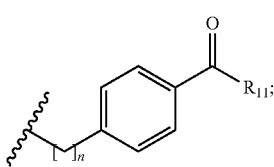

R₃, R₅, and R₇ are —H; R₈ is

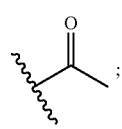

R₉ and R₁₀ are —H;
R₁₁ is an aryl group;
and
each n is 0, 1, 2, 3, or 4.

2. The method according to claim 1, wherein the compound has Formula (Ia):

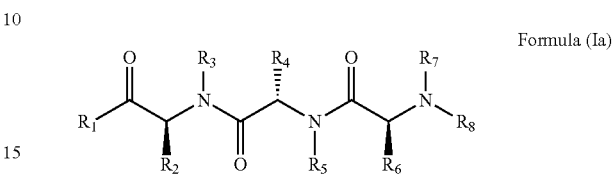

Formula (Ia)

3. The method according to claim 1, wherein R₁ is —NH₂.

4. The method according to claim 1, wherein R₂ is

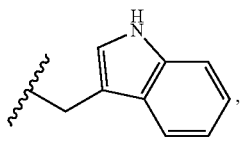 [SMILES: *Cc1c[nH]c2ccccc12]

R₄ is

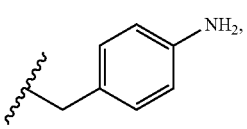 [SMILES: *Cc1ccc(N)cc1]

and R₆ is

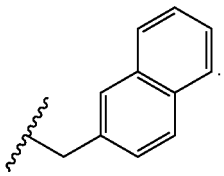 [SMILES: *Cc1ccc2ccccc2c1]

5. The method according to claim 1, wherein R₂ is

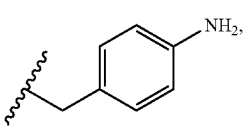 [SMILES: *Cc1ccc(N)cc1]

R₄ is

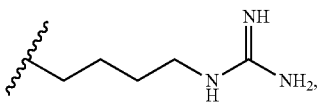

and R₆ is
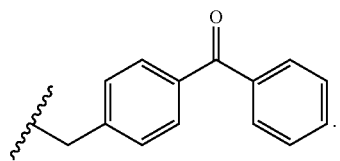 [SMILES: *Cc1ccc(C(=O)c2ccccc2)cc1]
6. The method according to claim 1, wherein the compound is a compound of Formula (101) or (103)
Formula (101)
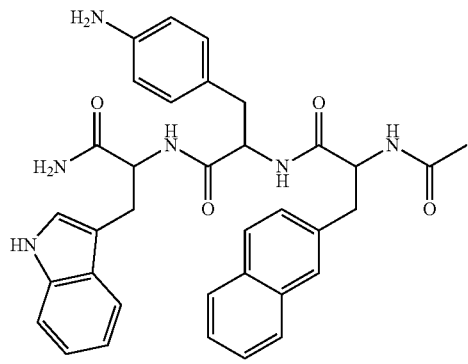
Formula (103)
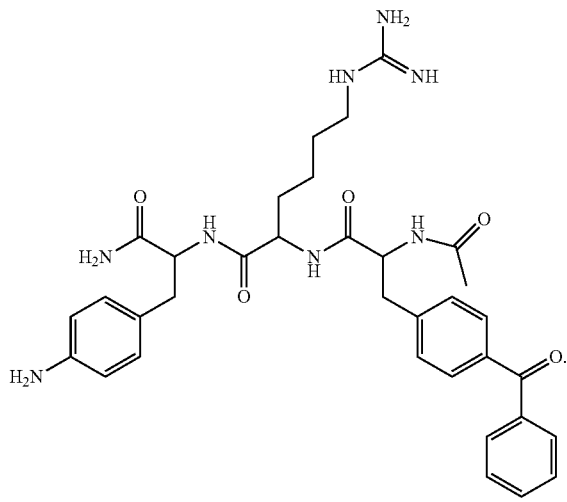
7. The method according to claim 6, wherein the compound is a compound of Formula (101a), or (103a):
Formula (101a)
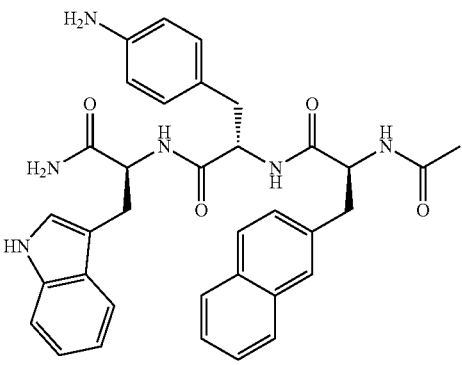
Formula (103a)
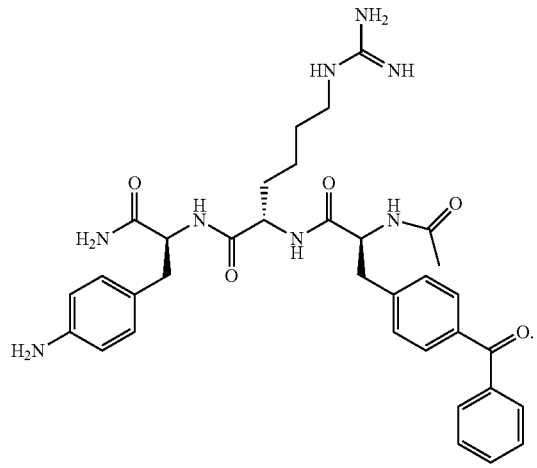
\* \* \* \* \*

SEQUENCE LISTING

```
<160> NUMBER OF SEQ ID NOS: 3

<210> SEQ ID NO 1
<211> LENGTH: 30
<212> TYPE: PRT
<213> ORGANISM: Artificial Sequence
<220> FEATURE:
<223> OTHER INFORMATION: synthetic peptide

<400> SEQUENCE: 1

Lys Ala Glu Phe His Arg Trp Ser Ser Tyr Met Val His Trp Lys Asn
1               5                   10                  15

Gln Phe Asp His Tyr Ser Lys Gln Asp Arg Cys Ser Asp Leu
            20                  25                  30

<210> SEQ ID NO 2
<211> LENGTH: 14
<212> TYPE: PRT
<213> ORGANISM: Artificial Sequence
<220> FEATURE:
<223> OTHER INFORMATION: synthetic peptide

<400> SEQUENCE: 2

Ala Glu Phe His Arg Trp Ser Ser Tyr Met Val His Trp Lys
1               5                   10

<210> SEQ ID NO 3
<211> LENGTH: 15
<212> TYPE: PRT
<213> ORGANISM: Artificial Sequence
<220> FEATURE:
<223> OTHER INFORMATION: synthetic peptide

<400> SEQUENCE: 3

Asn Gln Phe Asp His Tyr Ser Lys Gln Asp Arg Cys Ser Asp Leu
1               5                   10                  15
```